US011338046B2

(12) United States Patent
Roca Lecha et al.

(10) Patent No.: US 11,338,046 B2
(45) Date of Patent: May 24, 2022

(54) ADENOASSOCIATED VIRUS VECTORS FOR THE TREATMENT OF MUCOPOLYSACCHARIDOSES

(71) Applicants: ESTEVE PHARMACEUTICALS, S.A., Barcelona (ES); UNIVERSITAT AUTÓNOMA DE BARCELONA, Cerdanyola del Valles (ES)

(72) Inventors: Carles Roca Lecha, Badalona (ES); Virginia A. Haurigot-Mendonça, Barcelona (ES); Fàtima Bosch Tubert, Cerdanyola del Valles (ES)

(73) Assignees: ESTEVE PHARMACEUTICALS, S.A., Barcelona (ES); UNIVERSITAT AUTÓNOMA DE BARCELONA, Cerdanyola del Valles (ES)

( * ) Notice: Subject to any disclaimer, the term of this patent is extended or adjusted under 35 U.S.C. 154(b) by 472 days.

(21) Appl. No.: 16/337,953

(22) PCT Filed: Sep. 22, 2017

(86) PCT No.: PCT/EP2017/074081
§ 371 (c)(1),
(2) Date: Mar. 29, 2019

(87) PCT Pub. No.: WO2018/060097
PCT Pub. Date: Apr. 5, 2018

(65) Prior Publication Data

US 2019/0231900 A1 Aug. 1, 2019

(30) Foreign Application Priority Data

Sep. 30, 2016 (EP) .................................... 16382450

(51) Int. Cl.

| | |
|---|---|
| ***A61K 48/00*** | (2006.01) |
| ***A61K 38/46*** | (2006.01) |
| ***A61P 3/00*** | (2006.01) |
| ***C12N 15/86*** | (2006.01) |
| ***C12N 9/16*** | (2006.01) |

(52) U.S. Cl.
CPC ........ *A61K 48/0066* (2013.01); *A61K 38/465* (2013.01); *A61P 3/00* (2018.01); *C12N 9/16* (2013.01); *C12N 15/86* (2013.01); *C12Y 301/06014* (2013.01); *A01K 2217/075* (2013.01); *A01K 2227/105* (2013.01); *A01K 2267/0362* (2013.01); *C12N 2750/14143* (2013.01); *C12N 2830/15* (2013.01); *C12N 2830/90* (2013.01)

(58) Field of Classification Search
None
See application file for complete search history.

(56) References Cited

U.S. PATENT DOCUMENTS 7,232,670 B2 * 6/2007 D'Azzo ......... C12Y 304/16005 435/183
7,241,442 B2 * 7/2007 D'Azzo ......... C12Y 304/16005 424/94.1
11,065,309 B2 * 7/2021 Cao ........................ A61K 38/47

FOREIGN PATENT DOCUMENTS

| | | |
|---|---|---|
| WO | WO2015060722 | 4/2015 |
| WO | WO2015173308 | 11/2015 |
| WO | WO2016130591 | 8/2016 |

OTHER PUBLICATIONS

Alexopoulou, Annika, N., et al., "The CMV early enhancer/chicken β actin (CAG) promoter can be used to drive transgene expression during the differentiation of murine embryonic stem cells into vascular progenitors", BMC Cell Biology, 9:2, 2008.
Altschul, "BLAST Command Line Applications User Manual", Bethesda (MD): National Center for Biotechnology Information (US); 2008, pp. 1-60.
Altschul, Stephen, F., et al., "Basic local alignment search tool", J. Mol. Biol. 215, 1990, pp. 403-410.
Altschul, Stephen, F., et al., "Gapped BLAST and PSI-BLAST: a new generation of protein database search programs", Nucleic Acids Research, vol. 25, No. 17, 1997, pp. 3389-3402.
Ayuso.E., et al., "High AAV vector purity results in serotype- and tissue-independent enhancement of transduction efficiency", Gene Therapy, 17, 2010, pp. 503-510.
Baxter, Melissa, A., et al., "Retrovirally mediated correction of bone marrow-derived mesenchymal stem cells from patients with mucopolysaccharidosis type I", Blood, vol. 99, No. 5, Mar. 2002, pp. 1857-1859.
EESR for EP16382450.1; dated Jan. 5, 2017.
Fedele, Anthony, O., "Sanfilippo syndrome: causes, consequences, and treatments", The Application of Clinical Genetics, 8, 2015, pp. 269-281.
Gilkes, J.A., et al., "Preferred transduction with AAV8 and AAV9 via thalamic administration in the MPS IIIB model: A comparison of four rAAV serotypes". Molecular Genetics and Metabolism Reports, 6, 2016, pp. 48-54.
Haurigot, Virginia, et al., "Whole body correction of mucopolysaccharidosis IIIA by intracerebrospinal fluid gene therapy", The Journal of Clinical Investigation, vol. 123, No. 8, Aug. 2013, pp. 3254-3271.
International Search Report for PCT/EP2017/074081 dated Nov. 3, 2017.
Jakobkiewicz-Banecka, Joanna, et al., "Glycosaminoglycans and mucopolysaccharidosis type III". Frontiers in Bioscience, Landmark, 21, Jun. 2016, pp. 1393-1409.

(Continued)

*Primary Examiner* — Robert M Kelly
(74) *Attorney, Agent, or Firm* — Hueschen and Sage

(57) ABSTRACT

The present invention provides new adeno-associated virus-derived vectors and pharmaceutical compositions containing the same for the treatment of lysosomal storage disorders and specially, for the treatment of mucopolysaccharidoses Type IIID.

14 Claims, 26 Drawing Sheets

Specification includes a Sequence Listing.

(56) References Cited

OTHER PUBLICATIONS

Karpova, E.A., et al., "A fluorimetric enzyme assay for the diagnosis of Sanfilippo disease type A (MPS IIIA)", J. Inher. Metab. Dis., 19, 1996, pp. 278-285.

Ruzo, Albert, et al., "Correction of pathological accumulation of glycosaminoglycans in central nervous system and peripheral tissues of MPSIIIA mice through systemic AAV9 gene transfer", Human Gene Therapy, 23, Dec. 2012, pp. 1237-1246.

* cited by examiner

A

B

A

B

A

B

A

B

In vitro human GNS expression and activity

Intra-CSF - optimized murine GNS
(Males)
4 months post-administration

Intra-CSF - optimized murine GNS
(Males)
4 months post-administration

Intra-CSF - optimized murine GNS
(Males)
4 months post-administration

Intra-CSF - optimized murine GNS
(Males)
4 months post-administration

Intra-CSF - optimized murine GNS
(Males)
20 months post-administration

SEQUENCE LISTING

```
<160> NUMBER OF SEQ ID NOS: 28

<210> SEQ ID NO 1
<211> LENGTH: 1659
<212> TYPE: DNA
<213> ORGANISM: Homo sapiens

<400> SEQUENCE: 1

atgcggctcc tgcctctagc cccaggtcgg ctccggcggg gcagcccccg ccacctgccc      60

tcctgcagcc cagcgctgct actgctggtg ctgggcggct gcctgggggt cttcggggtg     120

gctgcgggaa cccggaggcc caacgtggtg ctgctcctca cggacgacca ggacgaagtg     180

ctcggcggca tgacaccgct aaagaaaacc aaagctctca tcggagagat ggggatgact     240

ttttccagtg cttatgtgcc aagtgctctc tgctgcccca gcagagccag tatcctgaca     300

ggaaagtacc cacataatca tcacgttgtg aacaacactc tggaggggaa ctgcagtagt     360

aagtcctggc agaagatcca agaaccaaat actttcccag caattctcag atcaatgtgt     420

ggttatcaga cctttttttgc agggaaatat ttaaatgagt acggagcccc agatgcaggt     480

ggactagaac acgttcctct gggttggagt tactggtatg ccttggaaaa gaattctaag     540

tattataatt acaccctgtc tatcaatggg aaggcacgga agcatggtga aaactatagt     600

gtggactacc tgacagatgt tttggctaat gtctccttgg actttctgga ctacaagtcc     660

aactttgagc ccttcttcat gatgatcgcc actccagcgc ctcattcgcc ttggacagct     720

gcacctcagt accagaaggc tttccagaat gtctttgcac caagaaacaa gaacttcaac     780

atccatggaa cgaacaagca ctggttaatt aggcaagcca agactccaat gactaattct     840

tcaatacagt ttttagataa tgcatttagg aaaaggtggc aaactctcct ctcagttgat     900

gaccttgtgg agaaactggt caagaggctg gagttcactg gggagctcaa caacacttac     960

atcttctata cctcagacaa tggctatcac acaggacagt tttccttgcc aatagacaag    1020

agacagctgt atgagtttga tatcaaagtt ccactgttgg ttcgaggacc tgggatcaaa    1080

ccaaatcaga caagcaagat gctggttgcc aacattgact tgggtcctac tattttggac    1140

attgctggct acgacctaaa taagacacag atggatggga tgtccttatt gcccattttg    1200

agaggtgcca gtaacttgac ctggcgatca gatgtcctgg tggaatacca aggagaaggc    1260

cgtaacgtca ctgacccaac atgccctcc ctgagtcctg gcgtatctca atgcttccca    1320

gactgtgtat gtgaagatgc ttataacaat acctatgcct gtgtgaggac aatgtcagca    1380

ttgtggaatt tgcagtattg cgagtttgat gaccaggagg tgtttgtaga agtctataat    1440

ctgactgcag acccagacca gatcactaac attgctaaaa ccatagaccc agagctttta    1500

ggaaagatga actatcggtt aatgatgtta cagtcctgtt ctgggccaac ctgtcgcact    1560
```

ccaggggttt ttgaccccgg atacaggttt gaccccccgtc tcatgttcag caatcgcggc 1620
agtgtcagga ctcgaagatt ttccaaacat cttctgtag 1659

<210> SEQ ID NO 2
<211> LENGTH: 1659
<212> TYPE: DNA
<213> ORGANISM: Artificial Sequence
<220> FEATURE:
<223> OTHER INFORMATION: ohGNS-version1

<400> SEQUENCE: 2
atgagactgc tgcctctggc tcctggccgg ctgagaagag gcagccctag acatctgccc 60
agctgctctc cagccctgct gctgctggtg ctgggaggat gcctgggagt gtttggagtg 120
gccgctggca ccagacggcc caatgtggtg ctgctgctga ccgacgacca ggacgaagtg 180
ctgggcggca tgaccccct gaaaaagacc aaggccctga tcggcgagat gggcatgacc 240
ttcagcagcg cctatgtgcc cagcgccctg tgctgtccta gcagagccag catcctgacc 300
ggcaagtacc cccacaacca ccatgtcgtg aacaacaccc tggaaggcaa ctgcagcagc 360
aagagctggc agaagatcca ggaacccaac accttccccg ccatcctgag atccatgtgc 420
ggctaccaga ccttcttcgc cggaaagtac ctgaacgagt acggcgctcc tgacgctggc 480
ggactggaac atgtgcctct gggctggtcc tattggtacg ccctggaaaa gaacagcaag 540
tactacaact acaccctgag catcaacggc aaggcccgga agcacggcga gaactacagc 600
gtggactacc tgaccgatgt gctggccaac gtgtccctgg acttcctgga ctacaagagc 660
aacttcgagc ccttcttcat gatgatcgcc acccctgccc cccacagccc ttggacagct 720
gctcctcagt accagaaagc cttccagaac gtgttcgccc ccagaaacaa gaacttcaac 780
atccacggca ccaacaagca ctggctgatc cggcaggcca agacccccat gaccaacagc 840
agcatccagt ttctggacaa cgccttcaga aagcggtggc agaccctgct gtccgtggac 900
gacctggtgg aaaagctcgt gaagcggctg gagttcaccg gcgagctgaa caatacctac 960
atcttctaca ccagcgacaa cggctaccac accggccagt tcagcctgcc catcgacaag 1020
cggcagctgt acgagttcga catcaaggtg cccctgctcg tgcggggacc tggcatcaag 1080
cctaaccaga cctccaagat gctggtggcc aacatcgacc tgggccccac catcctggat 1140
atcgccggct acgacctgaa caagacccag atggacggca tgtccctgct gcctatcctg 1200
agaggcgcca gcaatctgac atggcggagc gacgtgctgg tggaatatca gggcgagggc 1260
cggaacgtga ccgaccctac atgtcctagc ctgagccctg gcgtgtccca gtgcttccct 1320
gattgcgtgt gcgaggacgc ctacaacaac acctacgcct gcgtgcggac catgtccgcc 1380
ctgtggaacc tgcagtattg cgagttcgat gaccaggaag tgttcgtgga agtgtacaac 1440
ctgaccgccg accccgacca gatcaccaat atcgccaaga ccatcgaccc cgagctgctg 1500
ggaaagatga actaccggct gatgatgctg cagagctgca gcggccctac ctgcagaaca 1560
ccaggcgtgt tcgaccccgg ctacagattc gaccccagac tgatgttcag caaccggggc 1620
tccgtgcgca ccagaagatt cagcaaacat ctgctctga 1659

<210> SEQ ID NO 3
<211> LENGTH: 1659
<212> TYPE: DNA
<213> ORGANISM: Artificial Sequence
<220> FEATURE:
<223> OTHER INFORMATION: ohGNS-version2

<400> SEQUENCE: 3
atgaggctgc tgcccctggc ccccggaagg ttgcggcggg gttcgcctag acacctccct 60
tcatgctctc ccgccctgtt gctgctcgtg ctcggcggat gcctcggggt gttcggggtg 120
gccgcgggca cccggcgccc gaacgtcgtg ctgctgctga ccgacgacca agacgaggtg 180
ctcggtggca tgaccccgct gaagaaaacc aaggcgctga tcggtgaaat gggcatgacc 240
ttctcctccg catacgtgcc ctcggccctt tgctgtccgt cccgcgcgtc catcctgacc 300
gggaagtacc cgcataatca ccacgtcgtg aacaacactc tcgaggggaa ctgcagctcc 360
aagtcctggc agaagatcca agagcccaat accttccctg ctatcctgcg gtcgatgtgc 420
ggataccaga ccttctttgc cggaaagtat ctgaacgaat acggagcacc agatgccggt 480
ggactggaac atgtgccgct gggatggagc tattggtacg cactggagaa gaactccaag 540
tactacaatt acaccctgtc catcaacggg aaggcccgca agcacggcga aaactattcc 600
gtggactacc tcaccgacgt gctggccaac gtgtcgctgg atttccttga ctacaagtcc 660
aactttgagc ccttcttcat gatgatcgcc actccggcgc cccatagccc ctggaccgcc 720
gcgcctcagt accaaaaggc tttccagaac gtgttcgccc caagaaacaa gaacttcaat 780
attcacggaa ctaacaagca ctggctgatc agacaggcca aaactccaat gaccaactcg 840
agcatccagt tcctggacaa cgccttccgg aagcgctggc agaccctgct ctccgtggat 900
gacctggtgg aaaagctggt caagcggctg gagttcactg ggagttgaa caacacctat 960 atcttctaca cctccgacaa tggttaccac accggacagt tctcgctgcc aattgacaag 1020
cggcagctgt acgagttcga tattaaggtc ccacttcttg tgcgcgggcc gggaatcaag 1080
cccaaccaaa cttccaagat gctggtcgcc aacattgacc tgggtccgac tattctcgat 1140
atcgccggct acgacctgaa caagactcag atggacggca tgagcttgct gccgatcctg 1200
cgcggagcgt ccaacctgac ttggaggtcc gacgtcttgg tggaatacca gggcgaaggg 1260
cgcaacgtca ccgacccaac ttgcccttca ctgtcacccg gagtgtccca gtgcttcccc 1320
gactgcgtgt gtgaagatgc ctacaacaat acctacgcct gcgtgcgcac catgtccgct 1380
ctctggaacc tccagtactg cgaatttgac gaccaggagg tgttcgtgga agtgtacaac 1440
ctgacagccg atcctgacca aatcaccaac attgcaaaga ccatcgaccc tgagctgctg 1500
ggaaagatga actacaggct gatgatgctc cagagctgct ccggcccgac gtgccggacg 1560
ccgggagtgt ttgaccctgg ataccggttc gacccgagac tgatgttctc aaaccggggc 1620
tcggtccgga cccgaagatt cagcaaacac ctcctctga 1659

<210> SEQ ID NO 4
<211> LENGTH: 1659
<212> TYPE: DNA
<213> ORGANISM: Artificial Sequence
<220> FEATURE:
<223> OTHER INFORMATION: ohGNS-version3

<400> SEQUENCE: 4
atgcgactgc tgccactggc tcctggaaga ctgagacgag ggtcaccaag acatctgcct 60
agttgttcac ctgctctgct gctgctggtg ctgggcggct gcctgggcgt gttcggagtg 120
gcagcaggaa cccggcggcc caacgtggtg ctgctgctga cagacgatca ggacgaggtg 180
ctgggaggaa tgaccccccct gaagaagaca aaggccctga tcggcgagat gggcatgacc 240
tttagctccg cctacgtgcc tagcgccctg tgctgtccaa gccgggcctc tatcctgacc 300
ggcaagtatc cacacaatca ccacgtggtg aacaatacac tggagggcaa ctgctctagc 360

```
aagtcttggc agaagatcca ggagcctaat accttcccag ccatcctgag aagcatgtgc    420
ggctaccaga cattctttgc cggcaagtac ctgaacgagt atggcgcccc agatgcagga    480
ggcctggagc acgtgccact gggatggagc tactggtatg ccctggagaa gaacagcaag    540
tactataact acacactgag catcaatggc aaggccagga agcacggcga gaactactcc    600
gtggactatc tgaccgatgt gctggccaac gtgagcctgg acttcctgga ttacaagtct    660
aactttgagc ccttctttat gatgatcgca accccagcac ctcacagccc atggacagcc    720
gccccccagt atcagaaggc cttccagaac gtgttcgccc ctcggaacaa gaacttcaac    780
atccacggca ccaacaagca ctggctgatc agacaggcca agaccccaat gacaaattcc    840
tctatccagt tcctggacaa cgcctttagg aagcggtggc agaccctgct gtccgtggac    900
gatctggtgg agaagctggt gaagagactg gagttcacag gcgagctgaa caacacctac    960
atcttttata caagcgataa cggctaccac accggccagt tctccctgcc catcgacaag   1020
aggcagctgt atgagtttga tatcaaggtg cctctgctgg tgcgcggccc cggcatcaag   1080
cctaatcaga catctaagat gctggtggcc aacatcgacc tgggaccaac catcctggac   1140
atcgcaggct acgatctgaa caagacacag atggatggca tgtccctgct gcctatcctg   1200
aggggagcaa gcaatctgac ctggcgctcc gacgtgctgg tggagtatca gggcgagggc   1260
aggaacgtga ccgatccaac atgcccaagc ctgtcccccg gcgtgtccca gtgtttccct   1320
gactgcgtgt gcgaggatgc ctacaacaat acctatgcct gcgtgcgcac aatgtctgcc   1380
ctgtggaatc tgcagtactg tgagttcgac gatcaggagg tgtttgtgga ggtgtataat   1440
ctgaccgccg accctgatca gatcaccaac atcgccaaga caatcgaccc agagctgctg   1500
ggcaagatga actaccggct gatgatgctg cagtcttgca gcggccctac ctgtagaaca   1560
ccaggcgtgt tcgaccccgg ctatcggttt gatcctagac tgatgttttc caatagaggc   1620
tccgtgagga ctcggcggtt tagtaagcac ctgctgtaa                          1659
```

<210> SEQ ID NO 5
<211> LENGTH: 7894
<212> TYPE: DNA
<213> ORGANISM: Artificial Sequence
<220> FEATURE:
<223> OTHER INFORMATION: pAAV-CAG-hGNS

<400> SEQUENCE: 5

```
attacgccag ctgcgcgctc gctcgctcac tgaggccgcc cgggcaaagc ccgggcgtcg     60
ggcgaccttt ggtcgcccgg cctcagtgag cgagcgagcg cgcagagagg gagtggccaa    120
ctccatcact aggggttcct tgtagttaat gattaacccg ccatgctact tatctactcg    180
acattgatta ttgactagtt attaatagta atcaattacg gggtcattag ttcatagccc    240
atatatggag ttccgcgtta cataacttac ggtaaatggc ccgcctggct gaccgcccaa    300
cgacccccgc ccattgacgt caataatgac gtatgttccc atagtaacgc caatagggac    360
tttccattga cgtcaatggg tggagtattt acggtaaact gcccacttgg cagtacatca    420
agtgtatcat atgccaagta cgccccctat tgacgtcaat gacggtaaat ggcccgcctg    480
gcattatgcc cagtacatga ccttatggga ctttcctact tggcagtaca tctacgtatt    540
agtcatcgct attaccatgg tcgaggtgag ccccacgttc tgcttcactc tccccatctc    600
cccccctcc ccacccccaa ttttgtattt atttattttt taattatttt gtgcagcgat     660
gggggcgggg gggggggggg ggcgcgcgcc aggcggggcg gggcggggcg aggggcgggg    720
```

-continued

```
cggggcgagg cggagaggtg cggcggcagc caatcagagc ggcgcgctcc gaaagtttcc    780
ttttatggcg aggcggcggc ggcggcggcc ctataaaaag cgaagcgcgc ggcgggcggg    840
agtcgctgcg ttgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagggc cctttgtgcg gggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcaccccc   1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatgcggc tcctgcctct agccccaggt cggctccggc ggggcagccc   1980
ccgccacctg ccctcctgca gcccagcgct gctactgctg gtgctgggcg gctgcctggg   2040
ggtcttcggg gtggctgcgg gaacccggag gcccaacgtg gtgctgctcc tcacggacga   2100
ccaggacgaa gtgctcggcg gcatgacacc gctaaagaaa accaaagctc tcatcggaga   2160
gatggggatg actttttcca gtgcttatgt gccaagtgct ctctgctgcc ccagcagagc   2220
cagtatcctg acaggaaagt acccacataa tcatcacgtt gtgaacaaca ctctggaggg   2280
gaactgcagt agtaagtcct ggcagaagat ccaagaacca aatactttcc cagcaattct   2340
cagatcaatg tgtggttatc agaccttttt tgcagggaaa tatttaaatg agtacggagc   2400
cccagatgca ggtggactag aacacgttcc tctgggttgg agttactggt atgccttgga   2460
aaagaattct aagtattata attacaccct gtctatcaat gggaaggcac ggaagcatgg   2520
tgaaaactat agtgtggact acctgacaga tgttttggct aatgtctcct tggactttct   2580
ggactacaag tccaactttg agcccttctt catgatgatc gccactccag cgcctcattc   2640
gccttggaca gctgcacctc agtaccagaa ggctttccag aatgtctttg caccaagaaa   2700
caagaacttc aacatccatg gaacgaacaa gcactggtta attaggcaag ccaagactcc   2760
aatgactaat tcttcaatac agtttttaga taatgcattt aggaaaaggt ggcaaactct   2820
cctctcagtt gatgaccttg tggagaaact ggtcaagagg ctggagttca ctggggagct   2880
caacaacact tacatcttct atacctcaga caatggctat cacacaggac agttttcctt   2940
gccaatagac aagagacagc tgtatgagtt tgatatcaaa gttccactgt tggttcgagg   3000
acctgggatc aaaccaaatc agacaagcaa gatgctggtt gccaacattg acttgggtcc   3060
tactattttg gacattgctg gctacgacct aaataagaca cagatggatg ggatgtcctt   3120
```

```
attgcccatt ttgagaggtg ccagtaactt gacctggcga tcagatgtcc tggtggaata   3180
ccaaggagaa ggccgtaacg tcactgaccc aacatgccct tccctgagtc ctggcgtatc   3240
tcaatgcttc ccagactgtg tatgtgaaga tgcttataac aatacctatg cctgtgtgag   3300
gacaatgtca gcattgtgga atttgcagta ttgcgagttt gatgaccagg aggtgtttgt   3360
agaagtctat aatctgactg cagacccaga ccagatcact aacattgcta aaaccataga   3420
cccagagctt ttaggaaaga tgaactatcg gttaatgatg ttacagtcct gttctgggcc   3480
aacctgtcgc actccagggg tttttgaccc cggatacagg tttgaccccc gtctcatgtt   3540
cagcaatcgc ggcagtgtca ggactcgaag attttccaaa catcttctgt aggaattcga   3600
gctcggtacc cgggaatcaa ttcactcctc aggtgcaggc tgcctatcag aaggtggtgg   3660
ctggtgtggc caatgccctg gctcacaaat accactgaga tctttttccc tctgccaaaa   3720
attatgggga catcatgaag ccccttgagc atctgacttc tggctaataa aggaaattta   3780
ttttcattgc aatagtgtgt tggaattttt tgtgtctctc actcggaagg acatatggga   3840
gggcaaatca tttaaaacat cagaatgagt atttggttta gagtttggca acatatgccc   3900
atatgctggc tgccatgaac aaaggttggc tataaagagg tcatcagtat atgaaacagc   3960
cccctgctgt ccattcctta ttccatagaa aagccttgac ttgaggttag atttttttta   4020
tattttgttt tgtgttattt ttttctttaa catccctaaa attttcctta catgttttac   4080
tagccagatt tttcctcctc tcctgactac tcccagtcat agctgtccct cttctcttat   4140
ggagatccct cgacctgcag cccaagctgt agataagtag catggcgggt taatcattaa   4200
ctacaaggaa cccctagtga tggagttggc cactccctct ctgcgcgctc gctcgctcac   4260
tgaggccgcc cgggctttgc ccgggcggcc tcagtgagcg agcgagcgcg cagctgcatt   4320
aatgaatcgg ccaacgcgcg gggagaggcg gtttgcgtat tgggcgctct tccgcttcct   4380
cgctcactga ctcgctgcgc tcggtcgttc ggctgcggcg agcggtatca gctcactcaa   4440
aggcggtaat acggttatcc acagaatcag gggataacgc aggaaagaac atgtgagcaa   4500
aaggccagca aaaggccagg aaccgtaaaa aggccgcgtt gctggcgttt ttccataggc   4560
tccgcccccc tgacgagcat cacaaaaatc gacgctcaag tcagaggtgg cgaaacccga   4620
caggactata aagataccag gcgtttcccc ctggaagctc cctcgtgcgc tctcctgttc   4680
cgaccctgcc gcttaccgga tacctgtccg cctttctccc ttcgggaagc gtggcgcttt   4740
ctcatagctc acgctgtagg tatctcagtt cggtgtaggt cgttcgctcc aagctgggct   4800
gtgtgcacga accccccgtt cagcccgacc gctgcgcctt atccggtaac tatcgtcttg   4860
agtccaaccc ggtaagacac gacttatcgc cactggcagc agccactggt aacaggatta   4920
gcagagcgag gtatgtaggc ggtgctacag agttcttgaa gtggtggcct aactacggct   4980
acactagaag aacagtattt ggtatctgcg ctctgctgaa gccagttacc ttcggaaaaa   5040
gagttggtag ctcttgatcc ggcaaacaaa ccaccgctgg tagcggtggt ttttttgttt   5100
gcaagcagca gattacgcgc agaaaaaaag gatctcaaga agatcctttg atcttttcta   5160
cggggtctga cgctcagtgg aacgaaaact cacgttaagg gattttggtc atgagattat   5220
caaaaaggat cttcacctag atccttttaa attaaaaatg aagttttaaa tcaatctaaa   5280
gtatatatga gtaaacttgg tctgacagtt accaatgctt aatcagtgag gcacctatct   5340
cagcgatctg tctatttcgt tcatccatag ttgcctgact ccccgtcgtg tagataacta   5400
cgatacggga gggcttacca tctggcccca gtgctgcaat gataccgcga gacccacgct   5460
```

-continued

```
caccggctcc agatttatca gcaataaacc agccagccgg aagggccgag cgcagaagtg   5520
gtcctgcaac tttatccgcc tccatccagt ctattaattg ttgccgggaa gctagagtaa   5580
gtagttcgcc agttaatagt ttgcgcaacg ttgttgccat tgctacaggc atcgtggtgt   5640
cacgctcgtc gtttggtatg gcttcattca gctccggttc ccaacgatca aggcgagtta   5700
catgatcccc catgttgtgc aaaaaagcgg ttagctcctt cggtcctccg atcgttgtca   5760
gaagtaagtt ggccgcagtg ttatcactca tggttatggc agcactgcat aattctctta   5820
ctgtcatgcc atccgtaaga tgcttttctg tgactggtga gtactcaacc aagtcattct   5880
gagaatagtg tatgcggcga ccgagttgct cttgcccggc gtcaatacgg gataataccg   5940
cgccacatag cagaacttta aaagtgctca tcattggaaa acgttcttcg gggcgaaaac   6000
tctcaaggat cttaccgctg ttgagatcca gttcgatgta acccactcgt gcacccaact   6060
gatcttcagc atcttttact ttcaccagcg tttctgggtg agcaaaaaca ggaaggcaaa   6120
atgccgcaaa aaagggaata agggcgacac ggaaatgttg aatactcata ctcttccttt   6180
ttcaatatta ttgaagcatt tatcagggtt attgtctcat gagcggatac atatttgaat   6240
gtatttagaa aaataaacaa ataggggttc cgcgcacatt tccccgaaaa gtgccacctg   6300
acgtctaaga aaccattatt atcatgacat taacctataa aaataggcgt atcacgaggc   6360
cctttcgtct cgcgcgtttc ggtgatgacg gtgaaaacct ctgacacatg cagctcccgg   6420
agacggtcac agcttgtctg taagcggatg ccgggagcag acaagcccgt cagggcgcgt   6480
cagcgggtgt tggcgggtgt cggggctggc ttaactatgc ggcatcagag cagattgtac   6540
tgagagtgca ccatatgcgg tgtgaaatac cgcacagatg cgtaaggaga aaataccgca   6600
tcaggcgatt ccaacatcca ataaatcata caggcaaggc aaagaattag caaaattaag   6660
caataaagcc tcagagcata aagctaaatc ggttgtacca aaaacattat gaccctgtaa   6720
tacttttgcg ggagaagcct ttatttcaac gcaaggataa aaatttttag aaccctcata   6780
tattttaaat gcaatgcctg agtaatgtgt aggtaaagat tcaaacgggt gagaaaggcc   6840
ggagacagtc aaatcaccat caatatgata ttcaaccgtt ctagctgata aattcatgcc   6900
ggagagggta gctatttttg agaggtctct acaaaggcta tcaggtcatt gcctgagagt   6960
ctggagcaaa caagagaatc gatgaacggt aatcgtaaaa ctagcatgtc aatcatatgt   7020
accccggttg ataatcagaa aagccccaaa aacaggaaga ttgtataagc aaatatttaa   7080
attgtaagcg ttaatatttt gttaaaattc gcgttaaatt tttgttaaat cagctcattt   7140
tttaaccaat aggccgaaat cggcaaaatc ccttataaat caaaagaata gaccgagata   7200
gggttgagtg ttgttccagt ttggaacaag agtccactat taaagaacgt ggactccaac   7260
gtcaaagggc gaaaaaccgt ctatcagggc gatggcccac tacgtgaacc atcaccctaa   7320
tcaagttttt tggggtcgag gtgccgtaaa gcactaaatc ggaaccctaa agggagcccc   7380
cgatttagag cttgacgggg aaagccggcg aacgtggcga gaaaggaagg gaagaaagcg   7440
aaaggagcgg gcgctagggc gctggcaagt gtagcggtca cgctgcgcgt aaccaccaca   7500
cccgccgcgc ttaatgcgcc gctacagggc gcgtactatg gttgctttga cgagcacgta   7560
taacgtgctt tcctcgttag aatcagagcg ggagctaaac aggaggccga ttaaagggat   7620
tttagacagg aacggtacgc cagaatcctg agaagtgttt ttataatcag tgaggccacc   7680
gagtaaaaga gtctgtccat cacgcaaatt aaccgttgtc gcaatacttc tttgattagt   7740
aataacatca cttgcctgag tagaagaact caaactatcg gccttgctgg taatatccag   7800
```

aacaatatta ccgccagcca ttgcaacgga atcgccattc gccattcagg ctgcgcaact 7860
gttgggaagg gcgatcggtg cgggcctctt cgct 7894

<210> SEQ ID NO 6
<211> LENGTH: 7894
<212> TYPE: DNA
<213> ORGANISM: Artificial Sequence
<220> FEATURE:
<223> OTHER INFORMATION: pAAV-CAG-ohGNS-version1

<400> SEQUENCE: 6
attacgccag ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctactcg 180
acattgatta ttgactagtt attaatagta atcaattacg gggtcattag ttcatagccc 240
atatatggag ttccgcgtta cataacttac ggtaaatggc ccgcctggct gaccgcccaa 300
cgacccccgc ccattgacgt caataatgac gtatgttccc atagtaacgc caatagggac 360
tttccattga cgtcaatggg tggagtattt acggtaaact gcccacttgg cagtacatca 420
agtgtatcat atgccaagta cgccccctat tgacgtcaat gacggtaaat ggcccgcctg 480
gcattatgcc cagtacatga ccttatggga ctttcctact tggcagtaca tctacgtatt 540
agtcatcgct attaccatgg tcgaggtgag ccccacgttc tgcttcactc tccccatctc 600
ccccccctcc ccacccccaa ttttgtattt atttattttt taattatttt gtgcagcgat 660
gggggcgggg gggggggggg ggcgcgcgcc aggcggggcg gggcggggcg aggggcgggg 720
cggggcgagg cggagaggtg cggcggcagc caatcagagc ggcgcgctcc gaaagtttcc 780
ttttatggcg aggcggcggc ggcggcggcc ctataaaaag cgaagcgcgc ggcgggcggg 840
agtcgctgcg ttgccttcgc cccgtgcccc gctccgccgc cgcctcgcgc cgcccgcccc 900
ggctctgact gaccgcgtta ctcccacagg tgagcgggcg ggacggccct tctcctccgg 960
gctgtaatta gcgcttggtt taatgacggc ttgtttcttt tctgtggctg cgtgaaagcc 1020
ttgaggggct ccgggagggc cctttgtgcg gggggagcgg ctcggggggt gcgtgcgtgt 1080
gtgtgtgcgt ggggagcgcc gcgtgcggct ccgcgctgcc cggcggctgt gagcgctgcg 1140
ggcgcggcgc ggggctttgt gcgctccgca gtgtgcgcga ggggagcgcg gccgggggcg 1200
gtgccccgcg gtgcgggggg ggctgcgagg ggaacaaagg ctgcgtgcgg ggtgtgtgcg 1260
tgggggggtg agcagggggt gtgggcgcgt cggtcgggct gcaacccccc ctgcaccccc 1320
ctccccgagt tgctgagcac ggcccggctt cgggtgcggg gctccgtacg gggcgtggcg 1380
cggggctcgc cgtgccgggc ggggggtggc ggcaggtggg ggtgccgggc ggggcggggc 1440
cgcctcgggc cggggagggc tcgggggagg ggcgcggcgg cccccggagc gccggcggct 1500
gtcgaggcgc ggcgagccgc agccattgcc ttttatggta atcgtgcgag agggcgcagg 1560
gacttccttt gtcccaaatc tgtgcggagc cgaaatctgg gaggcgccgc cgcaccccct 1620
ctagcgggcg cggggcgaag cggtgcggcg ccggcaggaa ggaaatgggc ggggagggcc 1680
ttcgtgcgtc gccgcgccgc cgtccccttc tccctctcca gcctcggggc tgtccgcggg 1740
gggacggctg ccttcggggg ggacggggca gggcggggtt cggcttctgg cgtgtgaccg 1800
gcggctctag agcctctgct aaccatgttc atgccttctt ctttttccta cagctcctgg 1860
gcaacgtgct ggttattgtg ctgtctcatc attttggcaa agaattgatt aattcgagcg 1920

-continued

```
aacgcgtgcc accatgagac tgctgcctct ggctcctggc cggctgagaa gaggcagccc   1980
tagacatctg cccagctgct ctccagccct gctgctgctg gtgctgggag gatgcctggg   2040
agtgtttgga gtggccgctg gcaccagacg gcccaatgtg gtgctgctgc tgaccgacga   2100
ccaggacgaa gtgctgggcg gcatgacccc cctgaaaaag accaaggccc tgatcggcga   2160
gatgggcatg accttcagca gcgcctatgt gcccagcgcc ctgtgctgtc ctagcagagc   2220
cagcatcctg accggcaagt acccccacaa ccaccatgtc gtgaacaaca ccctggaagg   2280
caactgcagc agcaagagct ggcagaagat ccaggaaccc aacaccttcc ccgccatcct   2340
gagatccatg tgcggctacc agaccttctt cgccggaaag tacctgaacg agtacggcgc   2400
tcctgacgct ggcggactgg aacatgtgcc tctgggctgg tcctattggt acgccctgga   2460
aaagaacagc aagtactaca actacaccct gagcatcaac ggcaaggccc ggaagcacgg   2520
cgagaactac agcgtggact acctgaccga tgtgctggcc aacgtgtccc tggacttcct   2580
ggactacaag agcaacttcg agcccttctt catgatgatc gccacccctg ccccccacag   2640
cccttggaca gctgctcctc agtaccagaa agccttccag aacgtgttcg cccccagaaa   2700
caagaacttc aacatccacg gcaccaacaa gcactggctg atccggcagg ccaagacccc   2760
catgaccaac agcagcatcc agtttctgga caacgccttc agaaagcggt ggcagaccct   2820
gctgtccgtg gacgacctgg tggaaaagct cgtgaagcgg ctggagttca ccggcgagct   2880
gaacaatacc tacatcttct acaccagcga caacggctac cacaccggcc agttcagcct   2940
gcccatcgac aagcggcagc tgtacgagtt cgacatcaag gtgcccctgc tcgtgcgggg   3000
acctggcatc aagcctaacc agacctccaa gatgctggtg gccaacatcg acctgggccc   3060
caccatcctg gatatcgccg gctacgacct gaacaagacc cagatggacg gcatgtccct   3120
gctgcctatc ctgagaggcg ccagcaatct gacatggcgg agcgacgtgc tggtggaata   3180
tcagggcgag ggccggaacg tgaccgaccc tacatgtcct agcctgagcc ctggcgtgtc   3240
ccagtgcttc cctgattgcg tgtgcgagga cgcctacaac aacacctacg cctgcgtgcg   3300
gaccatgtcc gccctgtgga acctgcagta ttgcgagttc gatgaccagg aagtgttcgt   3360
ggaagtgtac aacctgaccg ccgaccccga ccagatcacc aatatcgcca agaccatcga   3420
ccccgagctg ctgggaaaga tgaactaccg gctgatgatg ctgcagagct gcagcggccc   3480
tacctgcaga acaccaggcg tgttcgaccc cggctacaga ttcgacccca gactgatgtt   3540
cagcaaccgg ggctccgtgc gcaccagaag attcagcaaa catctgctct gagaattcga   3600
gctcggtacc cgggaatcaa ttcactcctc aggtgcaggc tgcctatcag aaggtggtgg   3660
ctggtgtggc caatgccctg gctcacaaat accactgaga tctttttccc tctgccaaaa   3720
attatgggga catcatgaag ccccttgagc atctgacttc tggctaataa aggaaattta   3780
ttttcattgc aatagtgtgt tggaattttt tgtgtctctc actcggaagg acatatggga   3840
gggcaaatca tttaaaacat cagaatgagt atttggttta gagtttggca acatatgccc   3900
atatgctggc tgccatgaac aaaggttggc tataaagagg tcatcagtat atgaaacagc   3960
cccctgctgt ccattcctta ttccatagaa aagccttgac ttgaggttag atttttttta   4020
tattttgttt tgtgttattt ttttctttaa catccctaaa attttcctta catgttttac   4080
tagccagatt tttcctcctc tcctgactac tcccagtcat agctgtccct cttctcttat   4140
ggagatccct cgacctgcag cccaagctgt agataagtag catggcgggt taatcattaa   4200
ctacaaggaa cccctagtga tggagttggc cactccctct ctgcgcgctc gctcgctcac   4260
tgaggccgcc cgggctttgc ccgggcggcc tcagtgagcg agcgagcgcg cagctgcatt   4320
```

-continued

```
aatgaatcgg ccaacgcgcg gggagaggcg gtttgcgtat tgggcgctct tccgcttcct   4380
cgctcactga ctcgctgcgc tcggtcgttc ggctgcggcg agcggtatca gctcactcaa   4440
aggcggtaat acggttatcc acagaatcag gggataacgc aggaaagaac atgtgagcaa   4500
aaggccagca aaaggccagg aaccgtaaaa aggccgcgtt gctggcgttt ttccataggc   4560
tccgcccccc tgacgagcat cacaaaaatc gacgctcaag tcagaggtgg cgaaacccga   4620
caggactata aagataccag gcgtttcccc ctggaagctc cctcgtgcgc tctcctgttc   4680
cgaccctgcc gcttaccgga tacctgtccg cctttctccc ttcgggaagc gtggcgcttt   4740
ctcatagctc acgctgtagg tatctcagtt cggtgtaggt cgttcgctcc aagctgggct   4800
gtgtgcacga accccccgtt cagcccgacc gctgcgcctt atccggtaac tatcgtcttg   4860
agtccaaccc ggtaagacac gacttatcgc cactggcagc agccactggt aacaggatta   4920
gcagagcgag gtatgtaggc ggtgctacag agttcttgaa gtggtggcct aactacggct   4980
acactagaag aacagtattt ggtatctgcg ctctgctgaa gccagttacc ttcggaaaaa   5040
gagttggtag ctcttgatcc ggcaaacaaa ccaccgctgg tagcggtggt ttttttgttt   5100
gcaagcagca gattacgcgc agaaaaaaag gatctcaaga agatcctttg atcttttcta   5160
cggggtctga cgctcagtgg aacgaaaact cacgttaagg gattttggtc atgagattat   5220
caaaaaggat cttcacctag atccttttaa attaaaaatg aagttttaaa tcaatctaaa   5280
gtatatatga gtaaacttgg tctgacagtt accaatgctt aatcagtgag gcacctatct   5340
cagcgatctg tctatttcgt tcatccatag ttgcctgact ccccgtcgtg tagataacta   5400
cgatacggga gggcttacca tctggcccca gtgctgcaat gataccgcga gacccacgct   5460
caccggctcc agatttatca gcaataaacc agccagccgg aagggccgag cgcagaagtg   5520
gtcctgcaac tttatccgcc tccatccagt ctattaattg ttgccgggaa gctagagtaa   5580
gtagttcgcc agttaatagt ttgcgcaacg ttgttgccat tgctacaggc atcgtggtgt   5640
cacgctcgtc gtttggtatg gcttcattca gctccggttc ccaacgatca aggcgagtta   5700
catgatcccc catgttgtgc aaaaaagcgg ttagctcctt cggtcctccg atcgttgtca   5760
gaagtaagtt ggccgcagtg ttatcactca tggttatggc agcactgcat aattctctta   5820
ctgtcatgcc atccgtaaga tgcttttctg tgactggtga gtactcaacc aagtcattct   5880
gagaatagtg tatgcggcga ccgagttgct cttgcccggc gtcaatacgg gataataccg   5940
cgccacatag cagaacttta aaagtgctca tcattggaaa acgttcttcg gggcgaaaac   6000
tctcaaggat cttaccgctg ttgagatcca gttcgatgta acccactcgt gcacccaact   6060
gatcttcagc atcttttact ttcaccagcg tttctgggtg agcaaaaaca ggaaggcaaa   6120
atgccgcaaa aaagggaata agggcgacac ggaaatgttg aatactcata ctcttccttt   6180
ttcaatatta ttgaagcatt tatcagggtt attgtctcat gagcggatac atatttgaat   6240
gtatttagaa aaataaacaa ataggggttc cgcgcacatt tccccgaaaa gtgccacctg   6300
acgtctaaga aaccattatt atcatgacat taacctataa aaataggcgt atcacgaggc   6360
cctttcgtct cgcgcgtttc ggtgatgacg gtgaaaacct ctgacacatg cagctcccgg   6420
agacggtcac agcttgtctg taagcggatg ccgggagcag acaagcccgt cagggcgcgt   6480
cagcgggtgt tggcgggtgt cggggctggc ttaactatgc ggcatcagag cagattgtac   6540
tgagagtgca ccatatgcgg tgtgaaatac cgcacagatg cgtaaggaga aaataccgca   6600
tcaggcgatt ccaacatcca ataaatcata caggcaaggc aaagaattag caaaattaag   6660
```

-continued

```
caataaagcc tcagagcata aagctaaatc ggttgtacca aaaacattat gaccctgtaa   6720
tacttttgcg ggagaagcct ttatttcaac gcaaggataa aaatttttag aaccctcata   6780
tattttaaat gcaatgcctg agtaatgtgt aggtaaagat tcaaacgggt gagaaaggcc   6840
ggagacagtc aaatcaccat caatatgata ttcaaccgtt ctagctgata aattcatgcc   6900
ggagagggta gctatttttg agaggtctct acaaaggcta tcaggtcatt gcctgagagt   6960
ctggagcaaa caagagaatc gatgaacggt aatcgtaaaa ctagcatgtc aatcatatgt   7020
accccggttg ataatcagaa aagccccaaa aacaggaaga ttgtataagc aaatatttaa   7080
attgtaagcg ttaatatttt gttaaaattc gcgttaaatt tttgttaaat cagctcattt   7140
tttaaccaat aggccgaaat cggcaaaatc ccttataaat caaaagaata gaccgagata   7200
gggttgagtg ttgttccagt ttggaacaag agtccactat taaagaacgt ggactccaac   7260
gtcaaagggc gaaaaaccgt ctatcagggc gatggcccac tacgtgaacc atcaccctaa   7320
tcaagttttt tggggtcgag gtgccgtaaa gcactaaatc ggaaccctaa agggagcccc   7380
cgatttagag cttgacgggg aaagccggcg aacgtggcga gaaaggaagg gaagaaagcg   7440
aaaggagcgg gcgctagggc gctggcaagt gtagcggtca cgctgcgcgt aaccaccaca   7500
cccgccgcgc ttaatgcgcc gctacagggc gcgtactatg gttgctttga cgagcacgta   7560
taacgtgctt tcctcgttag aatcagagcg ggagctaaac aggaggccga ttaaagggat   7620
tttagacagg aacggtacgc cagaatcctg agaagtgttt ttataatcag tgaggccacc   7680
gagtaaaaga gtctgtccat cacgcaaatt aaccgttgtc gcaatacttc tttgattagt   7740
aataacatca cttgcctgag tagaagaact caaactatcg gccttgctgg taatatccag   7800
aacaatatta ccgccagcca ttgcaacgga atcgccattc gccattcagg ctgcgcaact   7860
gttgggaagg gcgatcggtg cgggcctctt cgct                                7894
```

```
<210> SEQ ID NO 7
<211> LENGTH: 7894
<212> TYPE: DNA
<213> ORGANISM: Artificial Sequence
<220> FEATURE:
<223> OTHER INFORMATION: pAAV-CAG-ohGNS-version2

<400> SEQUENCE: 7
```

```
attacgccag ctgcgcgctc gctcgctcac tgaggccgcc cgggcaaagc ccgggcgtcg     60
ggcgaccttt ggtcgcccgg cctcagtgag cgagcgagcg cgcagagagg gagtggccaa    120
ctccatcact aggggttcct tgtagttaat gattaacccg ccatgctact tatctactcg    180
acattgatta ttgactagtt attaatagta atcaattacg gggtcattag ttcatagccc    240
atatatggag ttccgcgtta cataacttac ggtaaatggc ccgcctggct gaccgcccaa    300
cgacccccgc ccattgacgt caataatgac gtatgttccc atagtaacgc caatagggac    360
tttccattga cgtcaatggg tggagtattt acggtaaact gcccacttgg cagtacatca    420
agtgtatcat atgccaagta cgccccctat tgacgtcaat gacggtaaat ggcccgcctg    480
gcattatgcc cagtacatga ccttatggga ctttcctact tggcagtaca tctacgtatt    540
agtcatcgct attaccatgg tcgaggtgag ccccacgttc tgcttcactc tccccatctc    600
ccccccctcc ccacccccaa ttttgtattt atttattttt taattatttt gtgcagcgat    660
gggggcgggg gggggggggg ggcgcgcgcc aggcggggcg gggcggggcg aggggcgggg    720
cggggcgagg cggagaggtg cggcggcagc caatcagagc ggcgcgctcc gaaagtttcc    780
ttttatggcg aggcggcggc ggcggcggcc ctataaaaag cgaagcgcgc ggcgggcggg    840
```

```
agtcgctgcg ttgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagggc cctttgtgcg gggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcacccccc  1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcacccccct  1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatgaggc tgctgcccct ggcccccgga aggttgcggc ggggttcgcc   1980
tagacacctc ccttcatgct ctcccgccct gttgctgctc gtgctcggcg gatgcctcgg   2040
ggtgttcggg gtggccgcgg gcacccggcg cccgaacgtc gtgctgctgc tgaccgacga   2100
ccaagacgag gtgctcggtg gcatgacccc gctgaagaaa accaaggcgc tgatcggtga   2160
aatgggcatg accttctcct ccgcatacgt gccctcggcc ctttgctgtc cgtcccgcgc   2220
gtccatcctg accgggaagt acccgcataa tcaccacgtc gtgaacaaca ctctcgaggg   2280
gaactgcagc tccaagtcct ggcagaagat ccaagagccc aataccttcc ctgctatcct   2340
gcggtcgatg tgcggatacc agaccttctt tgccggaaag tatctgaacg aatacggagc   2400
accagatgcc ggtggactgg aacatgtgcc gctgggatgg agctattggt acgcactgga   2460
gaagaactcc aagtactaca attacaccct gtccatcaac gggaaggccc gcaagcacgg   2520
cgaaaactat tccgtggact acctcaccga cgtgctggcc aacgtgtcgc tggatttcct   2580
tgactacaag tccaactttg agcccttctt catgatgatc gccactccgg cgccccatag   2640
cccctggacc gccgcgcctc agtaccaaaa ggctttccag aacgtgttcg ccccaagaaa   2700
caagaacttc aatattcacg gaactaacaa gcactggctg atcagacagg ccaaaactcc   2760
aatgaccaac tcgagcatcc agttcctgga caacgccttc cggaagcgct ggcagaccct   2820
gctctccgtg gatgacctgg tggaaaagct ggtcaagcgg ctggagttca ctggggagtt   2880
gaacaacacc tatatcttct acacctccga caatggttac cacaccggac agttctcgct   2940
gccaattgac aagcggcagc tgtacgagtt cgatattaag gtcccacttc ttgtgcgcgg   3000
gccgggaatc aagcccaacc aaacttccaa gatgctggtc gccaacattg acctgggtcc   3060
gactattctc gatatcgccg gctacgacct gaacaagact cagatggacg gcatgagctt   3120
gctgccgatc ctgcgcggag cgtccaacct gacttggagg tccgacgtct tggtggaata   3180
```

-continued

```
ccagggcgaa gggcgcaacg tcaccgaccc aacttgccct tcactgtcac ccggagtgtc   3240
ccagtgcttc cccgactgcg tgtgtgaaga tgcctacaac aatacctacg cctgcgtgcg   3300
caccatgtcc gctctctgga acctccagta ctgcgaattt gacgaccagg aggtgttcgt   3360
ggaagtgtac aacctgacag ccgatcctga ccaaatcacc aacattgcaa agaccatcga   3420
ccctgagctg ctgggaaaga tgaactacag gctgatgatg ctccagagct gctccggccc   3480
gacgtgccgg acgccgggag tgtttgaccc tggataccgg ttcgacccga gactgatgtt   3540
ctcaaaccgg ggctcggtcc ggacccgaag attcagcaaa cacctcctct gagaattcga   3600
gctcggtacc cgggaatcaa ttcactcctc aggtgcaggc tgcctatcag aaggtggtgg   3660
ctggtgtggc caatgccctg gctcacaaat accactgaga tctttttccc tctgccaaaa   3720
attatgggga catcatgaag ccccttgagc atctgacttc tggctaataa aggaaattta   3780
ttttcattgc aatagtgtgt tggaattttt tgtgtctctc actcggaagg acatatggga   3840
gggcaaatca tttaaaacat cagaatgagt atttggttta gagtttggca acatatgccc   3900
atatgctggc tgccatgaac aaaggttggc tataaagagg tcatcagtat atgaaacagc   3960
cccctgctgt ccattcctta ttccatagaa aagccttgac ttgaggttag atttttttta   4020
tattttgttt tgtgttattt ttttctttaa catccctaaa attttcctta catgttttac   4080
tagccagatt tttcctcctc tcctgactac tcccagtcat agctgtccct cttctcttat   4140
ggagatccct cgacctgcag cccaagctgt agataagtag catggcgggt taatcattaa   4200
ctacaaggaa cccctagtga tggagttggc cactccctct ctgcgcgctc gctcgctcac   4260
tgaggccgcc cgggctttgc ccgggcggcc tcagtgagcg agcgagcgcg cagctgcatt   4320
aatgaatcgg ccaacgcgcg gggagaggcg gtttgcgtat tgggcgctct tccgcttcct   4380
cgctcactga ctcgctgcgc tcggtcgttc ggctgcggcg agcggtatca gctcactcaa   4440
aggcggtaat acggttatcc acagaatcag gggataacgc aggaaagaac atgtgagcaa   4500
aaggccagca aaaggccagg aaccgtaaaa aggccgcgtt gctggcgttt ttccataggc   4560
tccgcccccc tgacgagcat cacaaaaatc gacgctcaag tcagaggtgg cgaaacccga   4620
caggactata aagataccag gcgtttcccc ctggaagctc cctcgtgcgc tctcctgttc   4680
cgaccctgcc gcttaccgga tacctgtccg cctttctccc ttcgggaagc gtggcgcttt   4740
ctcatagctc acgctgtagg tatctcagtt cggtgtaggt cgttcgctcc aagctgggct   4800
gtgtgcacga accccccgtt cagcccgacc gctgcgcctt atccggtaac tatcgtcttg   4860
agtccaaccc ggtaagacac gacttatcgc cactggcagc agccactggt aacaggatta   4920
gcagagcgag gtatgtaggc ggtgctacag agttcttgaa gtggtggcct aactacggct   4980
acactagaag aacagtattt ggtatctgcg ctctgctgaa gccagttacc ttcggaaaaa   5040
gagttggtag ctcttgatcc ggcaaacaaa ccaccgctgg tagcggtggt ttttttgttt   5100
gcaagcagca gattacgcgc agaaaaaaag gatctcaaga agatcctttg atcttttcta   5160
cggggtctga cgctcagtgg aacgaaaact cacgttaagg gattttggtc atgagattat   5220
caaaaaggat cttcacctag atccttttaa attaaaaatg aagttttaaa tcaatctaaa   5280
gtatatatga gtaaacttgg tctgacagtt accaatgctt aatcagtgag gcacctatct   5340
cagcgatctg tctatttcgt tcatccatag ttgcctgact ccccgtcgtg tagataacta   5400
cgatacggga gggcttacca tctggcccca gtgctgcaat gataccgcga gacccacgct   5460
caccggctcc agatttatca gcaataaacc agccagccgg aagggccgag cgcagaagtg   5520
gtcctgcaac tttatccgcc tccatccagt ctattaattg ttgccgggaa gctagagtaa   5580
```

-continued

```
gtagttcgcc agttaatagt ttgcgcaacg ttgttgccat tgctacaggc atcgtggtgt   5640
cacgctcgtc gtttggtatg gcttcattca gctccggttc ccaacgatca aggcgagtta   5700
catgatcccc catgttgtgc aaaaaagcgg ttagctcctt cggtcctccg atcgttgtca   5760
gaagtaagtt ggccgcagtg ttatcactca tggttatggc agcactgcat aattctctta   5820
ctgtcatgcc atccgtaaga tgcttttctg tgactggtga gtactcaacc aagtcattct   5880
gagaatagtg tatgcggcga ccgagttgct cttgcccggc gtcaatacgg gataataccg   5940
cgccacatag cagaacttta aaagtgctca tcattggaaa acgttcttcg gggcgaaaac   6000
tctcaaggat cttaccgctg ttgagatcca gttcgatgta acccactcgt gcacccaact   6060
gatcttcagc atcttttact ttcaccagcg tttctgggtg agcaaaaaca ggaaggcaaa   6120
atgccgcaaa aaagggaata agggcgacac ggaaatgttg aatactcata ctcttccttt   6180
ttcaatatta ttgaagcatt tatcagggtt attgtctcat gagcggatac atatttgaat   6240
gtatttagaa aaataaacaa ataggggttc cgcgcacatt tccccgaaaa gtgccacctg   6300
acgtctaaga aaccattatt atcatgacat taacctataa aaataggcgt atcacgaggc   6360
cctttcgtct cgcgcgtttc ggtgatgacg gtgaaaacct ctgacacatg cagctcccgg   6420
agacggtcac agcttgtctg taagcggatg ccgggagcag acaagcccgt cagggcgcgt   6480
cagcgggtgt tggcgggtgt cggggctggc ttaactatgc ggcatcagag cagattgtac   6540
tgagagtgca ccatatgcgg tgtgaaatac cgcacagatg cgtaaggaga aaataccgca   6600
tcaggcgatt ccaacatcca ataaatcata caggcaaggc aaagaattag caaaattaag   6660
caataaagcc tcagagcata aagctaaatc ggttgtacca aaaacattat gaccctgtaa   6720
tacttttgcg ggagaagcct ttatttcaac gcaaggataa aaatttttag aaccctcata   6780
tattttaaat gcaatgcctg agtaatgtgt aggtaaagat tcaaacgggt gagaaaggcc   6840
ggagacagtc aaatcaccat caatatgata ttcaaccgtt ctagctgata aattcatgcc   6900
ggagagggta gctatttttg agaggtctct acaaaggcta tcaggtcatt gcctgagagt   6960
ctggagcaaa caagagaatc gatgaacggt aatcgtaaaa ctagcatgtc aatcatatgt   7020
accccggttg ataatcagaa aagccccaaa aacaggaaga ttgtataagc aaatatttaa   7080
attgtaagcg ttaatatttt gttaaaattc gcgttaaatt tttgttaaat cagctcattt   7140
tttaaccaat aggccgaaat cggcaaaatc ccttataaat caaaagaata gaccgagata   7200
gggttgagtg ttgttccagt ttggaacaag agtccactat taaagaacgt ggactccaac   7260
gtcaaagggc gaaaaaccgt ctatcagggc gatggcccac tacgtgaacc atcaccctaa   7320
tcaagttttt tggggtcgag gtgccgtaaa gcactaaatc ggaaccctaa agggagcccc   7380
cgatttagag cttgacgggg aaagccggcg aacgtggcga gaaaggaagg gaagaaagcg   7440
aaaggagcgg gcgctagggc gctggcaagt gtagcggtca cgctgcgcgt aaccaccaca   7500
cccgccgcgc ttaatgcgcc gctacagggc gcgtactatg gttgctttga cgagcacgta   7560
taacgtgctt tcctcgttag aatcagagcg ggagctaaac aggaggccga ttaaagggat   7620
tttagacagg aacggtacgc cagaatcctg agaagtgttt ttataatcag tgaggccacc   7680
gagtaaaaga gtctgtccat cacgcaaatt aaccgttgtc gcaatacttc tttgattagt   7740
aataacatca cttgcctgag tagaagaact caaactatcg gccttgctgg taatatccag   7800
aacaatatta ccgccagcca ttgcaacgga atcgccattc gccattcagg ctgcgcaact   7860
gttgggaagg gcgatcggtg cgggcctctt cgct                                7894
```

<210> SEQ ID NO 8
<211> LENGTH: 7894
<212> TYPE: DNA
<213> ORGANISM: Artificial Sequence
<220> FEATURE:
<223> OTHER INFORMATION: pAAV-CAG-ohGNS-version3

<400> SEQUENCE: 8
attacgccag ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctactcg 180
acattgatta ttgactagtt attaatagta atcaattacg gggtcattag ttcatagccc 240
atatatggag ttccgcgtta cataacttac ggtaaatggc ccgcctggct gaccgcccaa 300
cgacccccgc ccattgacgt caataatgac gtatgttccc atagtaacgc caatagggac 360
tttccattga cgtcaatggg tggagtattt acggtaaact gcccacttgg cagtacatca 420
agtgtatcat atgccaagta cgccccctat tgacgtcaat gacggtaaat ggcccgcctg 480
gcattatgcc cagtacatga ccttatggga ctttcctact tggcagtaca tctacgtatt 540
agtcatcgct attaccatgg tcgaggtgag ccccacgttc tgcttcactc tccccatctc 600
ccccccctcc ccacccccaa ttttgtattt atttattttt taattatttt gtgcagcgat 660
gggggcgggg gggggggggg ggcgcgcgcc aggcggggcg gggcggggcg aggggcgggg 720
cggggcgagg cggagaggtg cggcggcagc caatcagagc ggcgcgctcc gaaagtttcc 780
ttttatggcg aggcggcggc ggcggcggcc ctataaaaag cgaagcgcgc ggcgggcggg 840
agtcgctgcg ttgccttcgc cccgtgcccc gctccgccgc cgcctcgcgc cgcccgcccc 900
ggctctgact gaccgcgtta ctcccacagg tgagcgggcg ggacggccct tctcctccgg 960
gctgtaatta gcgcttggtt taatgacggc ttgtttcttt tctgtggctg cgtgaaagcc 1020
ttgaggggct ccgggagggc cctttgtgcg gggggagcgg ctcggggggt gcgtgcgtgt 1080
gtgtgtgcgt ggggagcgcc gcgtgcggct ccgcgctgcc cggcggctgt gagcgctgcg 1140
ggcgcggcgc ggggctttgt gcgctccgca gtgtgcgcga ggggagcgcg gccgggggcg 1200
gtgccccgcg gtgcgggggg ggctgcgagg ggaacaaagg ctgcgtgcgg ggtgtgtgcg 1260
tgggggggtg agcagggggt gtgggcgcgt cggtcgggct gcaacccccc ctgcaccccc 1320
ctccccgagt tgctgagcac ggcccggctt cgggtgcggg gctccgtacg gggcgtggcg 1380
cggggctcgc cgtgccgggc ggggggtggc ggcaggtggg ggtgccgggc ggggcggggc 1440
cgcctcgggc cggggagggc tcgggggagg ggcgcggcgg cccccggagc gccggcggct 1500
gtcgaggcgc ggcgagccgc agccattgcc ttttatggta atcgtgcgag agggcgcagg 1560
gacttccttt gtcccaaatc tgtgcggagc cgaaatctgg gaggcgccgc cgcacccccct 1620 ctagcgggcg cggggcgaag cggtgcggcg ccggcaggaa ggaaatgggc ggggagggcc 1680
ttcgtgcgtc gccgcgccgc cgtccccttc tccctctcca gcctcggggc tgtccgcggg 1740
gggacggctg ccttcggggg ggacggggca gggcggggtt cggcttctgg cgtgtgaccg 1800
gcggctctag agcctctgct aaccatgttc atgccttctt ctttttccta cagctcctgg 1860
gcaacgtgct ggttattgtg ctgtctcatc attttggcaa agaattgatt aattcgagcg 1920
aacgcgtgcc accatgcgac tgctgccact ggctcctgga agactgagac gagggtcacc 1980
aagacatctg cctagttgtt cacctgctct gctgctgctg gtgctgggcg gctgcctggg 2040
cgtgttcgga gtggcagcag gaacccggcg gcccaacgtg gtgctgctgc tgacagacga 2100

-continued

```
tcaggacgag gtgctgggag gaatgacccc cctgaagaag acaaaggccc tgatcggcga   2160
gatgggcatg acctttagct ccgcctacgt gcctagcgcc ctgtgctgtc caagccgggc   2220
ctctatcctg accggcaagt atccacacaa tcaccacgtg gtgaacaata cactggaggg   2280
caactgctct agcaagtctt ggcagaagat ccaggagcct aataccttcc cagccatcct   2340
gagaagcatg tgcggctacc agacattctt tgccggcaag tacctgaacg agtatggcgc   2400
cccagatgca ggaggcctgg agcacgtgcc actgggatgg agctactggt atgccctgga   2460
gaagaacagc aagtactata actacacact gagcatcaat ggcaaggcca ggaagcacgg   2520
cgagaactac tccgtggact atctgaccga tgtgctggcc aacgtgagcc tggacttcct   2580
ggattacaag tctaactttg agcccttctt tatgatgatc gcaaccccag cacctcacag   2640
cccatggaca gccgcccccc agtatcagaa ggccttccag aacgtgttcg cccctcggaa   2700
caagaacttc aacatccacg gcaccaacaa gcactggctg atcagacagg ccaagacccc   2760
aatgacaaat tcctctatcc agttcctgga caacgccttt aggaagcggt ggcagaccct   2820
gctgtccgtg gacgatctgg tggagaagct ggtgaagaga ctggagttca caggcgagct   2880
gaacaacacc tacatctttt atacaagcga taacggctac cacaccggcc agttctccct   2940
gcccatcgac aagaggcagc tgtatgagtt tgatatcaag gtgcctctgc tggtgcgcgg   3000
ccccggcatc aagcctaatc agacatctaa gatgctggtg gccaacatcg acctgggacc   3060
aaccatcctg gacatcgcag gctacgatct gaacaagaca cagatggatg gcatgtccct   3120
gctgcctatc ctgaggggag caagcaatct gacctggcgc tccgacgtgc tggtggagta   3180
tcagggcgag ggcaggaacg tgaccgatcc aacatgccca agcctgtccc ccggcgtgtc   3240
ccagtgtttc cctgactgcg tgtgcgagga tgcctacaac aatacctatg cctgcgtgcg   3300
cacaatgtct gccctgtgga atctgcagta ctgtgagttc gacgatcagg aggtgtttgt   3360
ggaggtgtat aatctgaccg ccgaccctga tcagatcacc aacatcgcca agacaatcga   3420
cccagagctg ctgggcaaga tgaactaccg gctgatgatg ctgcagtctt gcagcggccc   3480
tacctgtaga acaccaggcg tgttcgaccc cggctatcgg tttgatccta gactgatgtt   3540
ttccaataga ggctccgtga ggactcggcg gtttagtaag cacctgctgt aagaattcga   3600
gctcggtacc cgggaatcaa ttcactcctc aggtgcaggc tgcctatcag aaggtggtgg   3660
ctggtgtggc caatgccctg gctcacaaat accactgaga tctttttccc tctgccaaaa   3720
attatgggga catcatgaag ccccttgagc atctgacttc tggctaataa aggaaattta   3780
ttttcattgc aatagtgtgt tggaattttt tgtgtctctc actcggaagg acatatggga   3840
gggcaaatca tttaaaacat cagaatgagt atttggttta gagtttggca acatatgccc   3900
atatgctggc tgccatgaac aaaggttggc tataaagagg tcatcagtat atgaaacagc   3960
cccctgctgt ccattcctta ttccatagaa aagccttgac ttgaggttag attttttta   4020
tattttgttt tgtgttattt ttttctttaa catccctaaa atttccttta catgttttac   4080
tagccagatt tttcctcctc tcctgactac tcccagtcat agctgtccct cttctcttat   4140
ggagatccct cgacctgcag cccaagctgt agataagtag catggcgggt taatcattaa   4200
ctacaaggaa cccctagtga tggagttggc cactccctct ctgcgcgctc gctcgctcac   4260
tgaggccgcc cgggctttgc ccgggcggcc tcagtgagcg agcgagcgcg cagctgcatt   4320
aatgaatcgg ccaacgcgcg gggagaggcg gtttgcgtat tgggcgctct tccgcttcct   4380
cgctcactga ctcgctgcgc tcggtcgttc ggctgcggcg agcggtatca gctcactcaa   4440
```

-continued

```
aggcggtaat acggttatcc acagaatcag gggataacgc aggaaagaac atgtgagcaa   4500
aaggccagca aaaggccagg aaccgtaaaa aggccgcgtt gctggcgttt ttccataggc   4560
tccgcccccc tgacgagcat cacaaaaatc gacgctcaag tcagaggtgg cgaaacccga   4620
caggactata aagataccag gcgtttcccc ctggaagctc cctcgtgcgc tctcctgttc   4680
cgaccctgcc gcttaccgga tacctgtccg cctttctccc ttcgggaagc gtggcgcttt   4740
ctcatagctc acgctgtagg tatctcagtt cggtgtaggt cgttcgctcc aagctgggct   4800
gtgtgcacga accccccgtt cagcccgacc gctgcgcctt atccggtaac tatcgtcttg   4860
agtccaaccc ggtaagacac gacttatcgc cactggcagc agccactggt aacaggatta   4920
gcagagcgag gtatgtaggc ggtgctacag agttcttgaa gtggtggcct aactacggct   4980
acactagaag aacagtattt ggtatctgcg ctctgctgaa gccagttacc ttcggaaaaa   5040
gagttggtag ctcttgatcc ggcaaacaaa ccaccgctgg tagcggtggt ttttttgttt   5100
gcaagcagca gattacgcgc agaaaaaaag gatctcaaga agatcctttg atcttttcta   5160
cggggtctga cgctcagtgg aacgaaaact cacgttaagg gattttggtc atgagattat   5220
caaaaaggat cttcacctag atccttttaa attaaaaatg aagttttaaa tcaatctaaa   5280
gtatatatga gtaaacttgg tctgacagtt accaatgctt aatcagtgag gcacctatct   5340
cagcgatctg tctatttcgt tcatccatag ttgcctgact ccccgtcgtg tagataacta   5400
cgatacggga gggcttacca tctggcccca gtgctgcaat gataccgcga gacccacgct   5460
caccggctcc agatttatca gcaataaacc agccagccgg aagggccgag cgcagaagtg   5520
gtcctgcaac tttatccgcc tccatccagt ctattaattg ttgccgggaa gctagagtaa   5580
gtagttcgcc agttaatagt ttgcgcaacg ttgttgccat tgctacaggc atcgtggtgt   5640
cacgctcgtc gtttggtatg gcttcattca gctccggttc ccaacgatca aggcgagtta   5700
catgatcccc catgttgtgc aaaaaagcgg ttagctcctt cggtcctccg atcgttgtca   5760
gaagtaagtt ggccgcagtg ttatcactca tggttatggc agcactgcat aattctctta   5820
ctgtcatgcc atccgtaaga tgcttttctg tgactggtga gtactcaacc aagtcattct   5880
gagaatagtg tatgcggcga ccgagttgct cttgcccggc gtcaatacgg gataataccg   5940
cgccacatag cagaacttta aaagtgctca tcattggaaa acgttcttcg gggcgaaaac   6000
tctcaaggat cttaccgctg ttgagatcca gttcgatgta acccactcgt gcacccaact   6060
gatcttcagc atcttttact ttcaccagcg tttctgggtg agcaaaaaca ggaaggcaaa   6120
atgccgcaaa aaagggaata agggcgacac ggaaatgttg aatactcata ctcttccttt   6180
ttcaatatta ttgaagcatt tatcagggtt attgtctcat gagcggatac atatttgaat   6240
gtatttagaa aaataaacaa ataggggttc cgcgcacatt tccccgaaaa gtgccacctg   6300
acgtctaaga aaccattatt atcatgacat taacctataa aaataggcgt atcacgaggc   6360
cctttcgtct cgcgcgtttc ggtgatgacg gtgaaaacct ctgacacatg cagctcccgg   6420
agacggtcac agcttgtctg taagcggatg ccgggagcag acaagcccgt cagggcgcgt   6480
cagcgggtgt tggcgggtgt cggggctggc ttaactatgc ggcatcagag cagattgtac   6540
tgagagtgca ccatatgcgg tgtgaaatac cgcacagatg cgtaaggaga aaataccgca   6600
tcaggcgatt ccaacatcca ataaatcata caggcaaggc aaagaattag caaaattaag   6660
caataaagcc tcagagcata aagctaaatc ggttgtacca aaaacattat gaccctgtaa   6720
tacttttgcg ggagaagcct ttatttcaac gcaaggataa aaatttttag aaccctcata   6780
tattttaaat gcaatgcctg agtaatgtgt aggtaaagat tcaaacgggt gagaaaggcc   6840
```

```
ggagacagtc aaatcaccat caatatgata ttcaaccgtt ctagctgata aattcatgcc   6900

ggagagggta gctatttttg agaggtctct acaaaggcta tcaggtcatt gcctgagagt   6960

ctggagcaaa caagagaatc gatgaacggt aatcgtaaaa ctagcatgtc aatcatatgt   7020

accccggttg ataatcagaa aagccccaaa aacaggaaga ttgtataagc aaatatttaa   7080

attgtaagcg ttaatatttt gttaaaattc gcgttaaatt tttgttaaat cagctcattt   7140

tttaaccaat aggccgaaat cggcaaaatc ccttataaat caaaagaata gaccgagata   7200

gggttgagtg ttgttccagt ttggaacaag agtccactat taaagaacgt ggactccaac   7260

gtcaaagggc gaaaaaccgt ctatcagggc gatggcccac tacgtgaacc atcaccctaa   7320

tcaagttttt tggggtcgag gtgccgtaaa gcactaaatc ggaaccctaa agggagcccc   7380

cgatttagag cttgacgggg aaagccggcg aacgtggcga gaaaggaagg gaagaaagcg   7440

aaaggagcgg gcgctagggc gctggcaagt gtagcggtca cgctgcgcgt aaccaccaca   7500

cccgccgcgc ttaatgcgcc gctacagggc gcgtactatg gttgctttga cgagcacgta   7560

taacgtgctt tcctcgttag aatcagagcg ggagctaaac aggaggccga ttaaagggat   7620

tttagacagg aacggtacgc cagaatcctg agaagtgttt ttataatcag tgaggccacc   7680

gagtaaaaga gtctgtccat cacgcaaatt aaccgttgtc gcaatacttc tttgattagt   7740

aataacatca cttgcctgag tagaagaact caaactatcg gccttgctgg taatatccag   7800

aacaatatta ccgccagcca ttgcaacgga atcgccattc gccattcagg ctgcgcaact   7860

gttgggaagg gcgatcggtg cgggcctctt cgct                               7894


<210> SEQ ID NO 9
<211> LENGTH: 4313
<212> TYPE: DNA
<213> ORGANISM: Artificial Sequence
<220> FEATURE:
<223> OTHER INFORMATION: AAV9-CAG-hGNS

<400> SEQUENCE: 9

attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960
```

-continued

```
gctgtaatta gcgcttggtt taatgacggc ttgtttcttt tctgtggctg cgtgaaagcc   1020
ttgaggggct ccgggagggc cctttgtgcg gggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcaccccc   1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcacccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatgcggc tcctgcctct agccccaggt cggctccggc ggggcagccc   1980
ccgccacctg ccctcctgca gcccagcgct gctactgctg gtgctgggcg gctgcctggg   2040
ggtcttcggg gtggctgcgg gaacccggag gcccaacgtg gtgctgctcc tcacggacga   2100
ccaggacgaa gtgctcggcg gcatgacacc gctaaagaaa accaaagctc tcatcggaga   2160
gatggggatg actttttcca gtgcttatgt gccaagtgct ctctgctgcc ccagcagagc   2220
cagtatcctg acaggaaagt acccacataa tcatcacgtt gtgaacaaca ctctggaggg   2280
gaactgcagt agtaagtcct ggcagaagat ccaagaacca aatactttcc cagcaattct   2340
cagatcaatg tgtggttatc agaccttttt tgcagggaaa tatttaaatg agtacggagc   2400
cccagatgca ggtggactag aacacgttcc tctgggttgg agttactggt atgccttgga   2460
aaagaattct aagtattata attacaccct gtctatcaat gggaaggcac ggaagcatgg   2520
tgaaaactat agtgtggact acctgacaga tgttttggct aatgtctcct tggactttct   2580
ggactacaag tccaactttg agcccttctt catgatgatc gccactccag cgcctcattc   2640
gccttggaca gctgcacctc agtaccagaa ggctttccag aatgtctttg caccaagaaa   2700
caagaacttc aacatccatg gaacgaacaa gcactggtta attaggcaag ccaagactcc   2760
aatgactaat tcttcaatac agtttttaga taatgcattt aggaaaaggt ggcaaactct   2820
cctctcagtt gatgaccttg tggagaaact ggtcaagagg ctggagttca ctggggagct   2880
caacaacact tacatcttct atacctcaga caatggctat cacacaggac agttttcctt   2940
gccaatagac aagagacagc tgtatgagtt tgatatcaaa gttccactgt tggttcgagg   3000
acctgggatc aaaccaaatc agacaagcaa gatgctggtt gccaacattg acttgggtcc   3060
tactattttg gacattgctg gctacgacct aaataagaca cagatggatg ggatgtcctt   3120
attgcccatt ttgagaggtg ccagtaactt gacctggcga tcagatgtcc tggtggaata   3180
ccaaggagaa ggccgtaacg tcactgaccc aacatgccct tccctgagtc ctggcgtatc   3240
tcaatgcttc ccagactgtg tatgtgaaga tgcttataac aatacctatg cctgtgtgag   3300
gacaatgtca gcattgtgga atttgcagta ttgcgagttt gatgaccagg aggtgtttgt   3360
```

```
agaagtctat aatctgactg cagacccaga ccagatcact aacattgcta aaaccataga   3420

cccagagctt ttaggaaaga tgaactatcg gttaatgatg ttacagtcct gttctgggcc   3480

aacctgtcgc actccagggg tttttgaccc cggatacagg tttgaccccc gtctcatgtt   3540

cagcaatcgc ggcagtgtca ggactcgaag attttccaaa catcttctgt aggaattcga   3600

gctcggtacc cgggaatcaa ttcactcctc aggtgcaggc tgcctatcag aaggtggtgg   3660

ctggtgtggc caatgccctg gctcacaaat accactgaga tctttttccc tctgccaaaa   3720

attatgggga catcatgaag ccccttgagc atctgacttc tggctaataa aggaaattta   3780

ttttcattgc aatagtgtgt tggaattttt tgtgtctctc actcggaagg acatatggga   3840

gggcaaatca tttaaaacat cagaatgagt atttggttta gagtttggca acatatgccc   3900

atatgctggc tgccatgaac aaaggttggc tataaagagg tcatcagtat atgaaacagc   3960

cccctgctgt ccattcctta ttccatagaa aagccttgac ttgaggttag atttttttta   4020

tattttgttt tgtgttattt ttttctttaa catccctaaa attttcctta catgttttac   4080

tagccagatt tttcctcctc tcctgactac tcccagtcat agctgtccct cttctcttat   4140

ggagatccct cgacctgcag cccaagctgt agataagtag catggcgggt taatcattaa   4200

ctacaaggaa cccctagtga tggagttggc cactccctct ctgcgcgctc gctcgctcac   4260

tgaggccgcc cgggctttgc ccgggcggcc tcagtgagcg agcgagcgcg cag          4313
```

```
<210> SEQ ID NO 10
<211> LENGTH: 4313
<212> TYPE: DNA
<213> ORGANISM: Artificial Sequence
<220> FEATURE:
<223> OTHER INFORMATION: AAV9-CAG-ohGNS-version1

<400> SEQUENCE: 10

attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcgggggt gcgtgcgtgt   1080
```

-continued

```
gtgtgtgcgt ggggagcgcc gcgtgcggct ccgcgctgcc cggcggctgt gagcgctgcg   1140
ggcgcggcgc ggggctttgt gcgctccgca gtgtgcgcga ggggagcgcg gccgggggcg   1200
gtgccccgcg gtgcgggggg ggctgcgagg ggaacaaagg ctgcgtgcgg ggtgtgtgcg   1260
tgggggggtg agcagggggt gtgggcgcgt cggtcgggct gcaacccccc ctgcaccccc   1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatgagac tgctgcctct ggctcctggc cggctgagaa gaggcagccc   1980
tagacatctg cccagctgct ctccagccct gctgctgctg gtgctgggag gatgcctggg   2040
agtgtttgga gtggccgctg gcaccagacg gcccaatgtg gtgctgctgc tgaccgacga   2100
ccaggacgaa gtgctgggcg gcatgacccc cctgaaaaag accaaggccc tgatcggcga   2160
gatgggcatg accttcagca gcgcctatgt gcccagcgcc ctgtgctgtc ctagcagagc   2220
cagcatcctg accggcaagt acccccacaa ccaccatgtc gtgaacaaca ccctggaagg   2280
caactgcagc agcaagagct ggcagaagat ccaggaaccc aacaccttcc ccgccatcct   2340
gagatccatg tgcggctacc agaccttctt cgccggaaag tacctgaacg agtacggcgc   2400
tcctgacgct ggcggactgg aacatgtgcc tctgggctgg tcctattggt acgccctgga   2460
aaagaacagc aagtactaca actacaccct gagcatcaac ggcaaggccc ggaagcacgg   2520
cgagaactac agcgtggact acctgaccga tgtgctggcc aacgtgtccc tggacttcct   2580
ggactacaag agcaacttcg agcccttctt catgatgatc gccacccctg ccccccacag   2640
cccttggaca gctgctcctc agtaccagaa agccttccag aacgtgttcg cccccagaaa   2700
caagaacttc aacatccacg gcaccaacaa gcactggctg atccggcagg ccaagacccc   2760
catgaccaac agcagcatcc agtttctgga caacgccttc agaaagcggt ggcagaccct   2820
gctgtccgtg gacgacctgg tggaaaagct cgtgaagcgg ctggagttca ccggcgagct   2880
gaacaatacc tacatcttct acaccagcga caacggctac cacaccggcc agttcagcct   2940
gcccatcgac aagcggcagc tgtacgagtt cgacatcaag gtgcccctgc tcgtgcgggg   3000
acctggcatc aagcctaacc agacctccaa gatgctggtg gccaacatcg acctgggccc   3060
caccatcctg gatatcgccg gctacgacct gaacaagacc cagatggacg gcatgtccct   3120
gctgcctatc ctgagaggcg ccagcaatct gacatggcgg agcgacgtgc tggtggaata   3180
tcagggcgag ggccggaacg tgaccgaccc tacatgtcct agcctgagcc ctggcgtgtc   3240
ccagtgcttc cctgattgcg tgtgcgagga cgcctacaac aacacctacg cctgcgtgcg   3300
gaccatgtcc gccctgtgga acctgcagta ttgcgagttc gatgaccagg aagtgttcgt   3360
ggaagtgtac aacctgaccg ccgaccccga ccagatcacc aatatcgcca agaccatcga   3420
ccccgagctg ctgggaaaga tgaactaccg gctgatgatg ctgcagagct gcagcggccc   3480
```

```
tacctgcaga acaccaggcg tgttcgaccc cggctacaga ttcgacccca gactgatgtt   3540

cagcaaccgg ggctccgtgc gcaccagaag attcagcaaa catctgctct gagaattcga   3600

gctcggtacc cgggaatcaa ttcactcctc aggtgcaggc tgcctatcag aaggtggtgg   3660

ctggtgtggc caatgccctg gctcacaaat accactgaga tctttttccc tctgccaaaa   3720

attatgggga catcatgaag ccccttgagc atctgacttc tggctaataa aggaaattta   3780

ttttcattgc aatagtgtgt tggaattttt tgtgtctctc actcggaagg acatatggga   3840

gggcaaatca tttaaaacat cagaatgagt atttggttta gagtttggca acatatgccc   3900

atatgctggc tgccatgaac aaaggttggc tataaagagg tcatcagtat atgaaacagc   3960

cccctgctgt ccattcctta ttccatagaa aagccttgac ttgaggttag atttttttta   4020

tattttgttt tgtgttattt ttttctttaa catccctaaa attttcctta catgttttac   4080

tagccagatt tttcctcctc tcctgactac tcccagtcat agctgtccct cttctcttat   4140

ggagatccct cgacctgcag cccaagctgt agataagtag catggcgggt taatcattaa   4200

ctacaaggaa cccctagtga tggagttggc cactccctct ctgcgcgctc gctcgctcac   4260

tgaggccgcc cgggctttgc ccgggcggcc tcagtgagcg agcgagcgcg cag          4313
```

<210> SEQ ID NO 11
<211> LENGTH: 4313
<212> TYPE: DNA
<213> ORGANISM: Artificial Sequence
<220> FEATURE:
<223> OTHER INFORMATION: AAV9-CAG-ohGNS-version2

<400> SEQUENCE: 11

```
attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcggggggt gcgtgcgtgt   1080

gtgtgtgcgt ggggagcgcc gcgtgcggct ccgcgctgcc cggcggctgt gagcgctgcg   1140

ggcgcggcgc ggggctttgt gcgctccgca gtgtgcgcga ggggagcgcg gccgggggcg   1200
```

gtgccccgcg gtgcgggggg ggctgcgagg ggaacaaagg ctgcgtgcgg ggtgtgtgcg 1260
tgggggggtg agcagggggt gtgggcgcgt cggtcgggct gcaacccccc ctgcaccccc 1320
ctccccgagt tgctgagcac ggcccggctt cgggtgcggg gctccgtacg gggcgtggcg 1380
cggggctcgc cgtgccgggc ggggggtggc ggcaggtggg ggtgccgggc ggggcggggc 1440
cgcctcgggc cggggagggc tcgggggagg ggcgcggcgg cccccggagc gccggcggct 1500
gtcgaggcgc ggcgagccgc agccattgcc ttttatggta atcgtgcgag agggcgcagg 1560
gacttccttt gtcccaaatc tgtgcggagc cgaaatctgg gaggcgccgc cgcaccccct 1620
ctagcgggcg cggggcgaag cggtgcggcg ccggcaggaa ggaaatgggc ggggagggcc 1680
ttcgtgcgtc gccgcgccgc cgtccccttc tccctctcca gcctcggggc tgtccgcggg 1740
gggacggctg ccttcggggg ggacggggca gggcggggtt cggcttctgg cgtgtgaccg 1800
gcggctctag agcctctgct aaccatgttc atgccttctt ctttttccta cagctcctgg 1860
gcaacgtgct ggttattgtg ctgtctcatc attttggcaa agaattgatt aattcgagcg 1920
aacgcgtgcc accatgaggc tgctgccct ggcccccgga aggttgcggc ggggttcgcc 1980
tagacacctc ccttcatgct ctcccgccct gttgctgctc gtgctcggcg gatgcctcgg 2040
ggtgttcggg gtggccgcgg gcacccggcg cccgaacgtc gtgctgctgc tgaccgacga 2100
ccaagacgag gtgctcggtg gcatgacccc gctgaagaaa accaaggcgc tgatcggtga 2160
aatgggcatg accttctcct ccgcatacgt gccctcggcc ctttgctgtc cgtcccgcgc 2220
gtccatcctg accgggaagt acccgcataa tcaccacgtc gtgaacaaca ctctcgaggg 2280
gaactgcagc tccaagtcct ggcagaagat ccaagagccc aataccttcc ctgctatcct 2340
gcggtcgatg tgcggatacc agaccttctt tgccggaaag tatctgaacg aatacggagc 2400
accagatgcc ggtggactgg aacatgtgcc gctgggatgg agctattggt acgcactgga 2460
gaagaactcc aagtactaca attacaccct gtccatcaac gggaaggccc gcaagcacgg 2520
cgaaaactat tccgtggact acctcaccga cgtgctggcc aacgtgtcgc tggatttcct 2580
tgactacaag tccaactttg agcccttctt catgatgatc gccactccgg cgccccatag 2640
cccctggacc gccgcgcctc agtaccaaaa ggctttccag aacgtgttcg ccccaagaaa 2700
caagaacttc aatattcacg gaactaacaa gcactggctg atcagacagg ccaaaactcc 2760
aatgaccaac tcgagcatcc agttcctgga caacgccttc cggaagcgct ggcagaccct 2820
gctctccgtg gatgacctgg tggaaaagct ggtcaagcgg ctggagttca ctggggagtt 2880
gaacaacacc tatatcttct acacctccga caatggttac cacaccggac agttctcgct 2940
gccaattgac aagcggcagc tgtacgagtt cgatattaag gtcccacttc ttgtgcgcgg 3000
gccgggaatc aagcccaacc aaacttccaa gatgctggtc gccaacattg acctgggtcc 3060
gactattctc gatatcgccg gctacgacct gaacaagact cagatggacg gcatgagctt 3120
gctgccgatc ctgcgcggag cgtccaacct gacttggagg tccgacgtct tggtggaata 3180
ccagggcgaa gggcgcaacg tcaccgaccc aacttgccct tcactgtcac ccggagtgtc 3240
ccagtgcttc cccgactgcg tgtgtgaaga tgcctacaac aatacctacg cctgcgtgcg 3300
caccatgtcc gctctctgga acctccagta ctgcgaattt gacgaccagg aggtgttcgt 3360
ggaagtgtac aacctgacag ccgatcctga ccaaatcacc aacattgcaa agaccatcga 3420
ccctgagctg ctgggaaaga tgaactacag gctgatgatg ctccagagct gctccggccc 3480
gacgtgccgg acgccgggag tgtttgaccc tggataccgg ttcgacccga gactgatgtt 3540
ctcaaaccgg ggctcggtcc ggacccgaag attcagcaaa cacctcctct gagaattcga 3600

```
gctcggtacc cgggaatcaa ttcactcctc aggtgcaggc tgcctatcag aaggtggtgg   3660

ctggtgtggc caatgccctg gctcacaaat accactgaga tctttttccc tctgccaaaa   3720

attatgggga catcatgaag ccccttgagc atctgacttc tggctaataa aggaaattta   3780

ttttcattgc aatagtgtgt tggaattttt tgtgtctctc actcggaagg acatatggga   3840

gggcaaatca tttaaaacat cagaatgagt atttggttta gagtttggca acatatgccc   3900

atatgctggc tgccatgaac aaaggttggc tataaagagg tcatcagtat atgaaacagc   3960

cccctgctgt ccattcctta ttccatagaa aagccttgac ttgaggttag atttttttta   4020

tattttgttt tgtgttattt ttttctttaa catccctaaa attttcctta catgttttac   4080

tagccagatt tttcctcctc tcctgactac tcccagtcat agctgtccct cttctcttat   4140

ggagatccct cgacctgcag cccaagctgt agataagtag catggcgggt taatcattaa   4200

ctacaaggaa cccctagtga tggagttggc cactccctct ctgcgcgctc gctcgctcac   4260

tgaggccgcc cgggctttgc ccgggcggcc tcagtgagcg agcgagcgcg cag          4313
```

<210> SEQ ID NO 12
<211> LENGTH: 4313
<212> TYPE: DNA
<213> ORGANISM: Artificial Sequence
<220> FEATURE:
<223> OTHER INFORMATION: AAV9-CAG-ohGNS-version3

<400> SEQUENCE: 12

```
attacgccag ctgcgcgctc gctcgctcac tgaggccgcc cgggcaaagc ccgggcgtcg     60

ggcgaccttt ggtcgcccgg cctcagtgag cgagcgagcg cgcagagagg gagtggccaa    120

ctccatcact aggggttcct tgtagttaat gattaacccg ccatgctact tatctactcg    180

acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcggggggt gcgtgcgtgt   1080

gtgtgtgcgt ggggagcgcc gcgtgcggct ccgcgctgcc cggcggctgt gagcgctgcg   1140

ggcgcggcgc ggggctttgt gcgctccgca gtgtgcgcga ggggagcgcg gccgggggcg   1200

gtgccccgcg gtgcgggggg ggctgcgagg ggaacaaagg ctgcgtgcgg ggtgtgtgcg   1260

tggggggggtg agcagggggt gtgggcgcgt cggtcgggct gcaacccccc ctgcaccccc   1320
```

```
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgcc accatgcgac tgctgccact ggctcctgga agactgagac gagggtcacc   1980
aagacatctg cctagttgtt cacctgctct gctgctgctg gtgctgggcg gctgcctggg   2040
cgtgttcgga gtggcagcag gaacccggcg gcccaacgtg gtgctgctgc tgacagacga   2100
tcaggacgag gtgctgggag gaatgacccc cctgaagaag acaaaggccc tgatcggcga   2160
gatgggcatg acctttagct ccgcctacgt gcctagcgcc ctgtgctgtc caagccgggc   2220
ctctatcctg accggcaagt atccacacaa tcaccacgtg gtgaacaata cactggaggg   2280
caactgctct agcaagtctt ggcagaagat ccaggagcct aataccttcc cagccatcct   2340
gagaagcatg tgcggctacc agacattctt tgccggcaag tacctgaacg agtatggcgc   2400
cccagatgca ggaggcctgg agcacgtgcc actgggatgg agctactggt atgccctgga   2460
gaagaacagc aagtactata actacacact gagcatcaat ggcaaggcca ggaagcacgg   2520
cgagaactac tccgtggact atctgaccga tgtgctggcc aacgtgagcc tggacttcct   2580
ggattacaag tctaactttg agcccttctt tatgatgatc gcaaccccag cacctcacag   2640
cccatggaca gccgcccccc agtatcagaa ggccttccag aacgtgttcg cccctcggaa   2700
caagaacttc aacatccacg gcaccaacaa gcactggctg atcagacagg ccaagacccc   2760
aatgacaaat tcctctatcc agttcctgga caacgccttt aggaagcggt ggcagaccct   2820
gctgtccgtg gacgatctgg tggagaagct ggtgaagaga ctggagttca caggcgagct   2880
gaacaacacc tacatctttt atacaagcga taacggctac cacaccggcc agttctccct   2940
gcccatcgac aagaggcagc tgtatgagtt tgatatcaag gtgcctctgc tggtgcgcgg   3000
ccccggcatc aagcctaatc agacatctaa gatgctggtg gccaacatcg acctgggacc   3060
aaccatcctg gacatcgcag gctacgatct gaacaagaca cagatggatg gcatgtccct   3120
gctgcctatc ctgaggggag caagcaatct gacctggcgc tccgacgtgc tggtggagta   3180
tcagggcgag ggcaggaacg tgaccgatcc aacatgccca agcctgtccc ccggcgtgtc   3240
ccagtgtttc cctgactgcg tgtgcgagga tgcctacaac aatacctatg cctgcgtgcg   3300
cacaatgtct gccctgtgga atctgcagta ctgtgagttc gacgatcagg aggtgtttgt   3360
ggaggtgtat aatctgaccg ccgaccctga tcagatcacc aacatcgcca agacaatcga   3420
cccagagctg ctgggcaaga tgaactaccg gctgatgatg ctgcagtctt gcagcggccc   3480
tacctgtaga acaccaggcg tgttcgaccc cggctatcgg tttgatccta gactgatgtt   3540
ttccaataga ggctccgtga ggactcggcg gtttagtaag cacctgctgt aagaattcga   3600
gctcggtacc cgggaatcaa ttcactcctc aggtgcaggc tgcctatcag aaggtggtgg   3660
ctggtgtggc caatgccctg gctcacaaat accactgaga tctttttccc tctgccaaaa   3720
```

attatgggga catcatgaag ccccttgagc atctgacttc tggctaataa aggaaattta 3780
ttttcattgc aatagtgtgt tggaattttt tgtgtctctc actcggaagg acatatggga 3840
gggcaaatca tttaaaacat cagaatgagt atttggttta gagtttggca acatatgccc 3900
atatgctggc tgccatgaac aaaggttggc tataaagagg tcatcagtat atgaaacagc 3960
cccctgctgt ccattcctta ttccatagaa aagccttgac ttgaggttag atttttttta 4020
tattttgttt tgtgttattt ttttctttaa catccctaaa attttcctta catgttttac 4080
tagccagatt tttcctcctc tcctgactac tcccagtcat agctgtccct cttctcttat 4140
ggagatccct cgacctgcag cccaagctgt agataagtag catggcgggt taatcattaa 4200
ctacaaggaa cccctagtga tggagttggc cactccctct ctgcgcgctc gctcgctcac 4260
tgaggccgcc cgggctttgc ccgggcggcc tcagtgagcg agcgagcgcg cag 4313

<210> SEQ ID NO 13
<211> LENGTH: 20
<212> TYPE: DNA
<213> ORGANISM: Artificial Sequence
<220> FEATURE:
<223> OTHER INFORMATION: GNS sense primer

<400> SEQUENCE: 13
ccacacaggg cagttctctt 20

<210> SEQ ID NO 14
<211> LENGTH: 20
<212> TYPE: DNA
<213> ORGANISM: Artificial Sequence
<220> FEATURE:
<223> OTHER INFORMATION: GNS antisense primer

<400> SEQUENCE: 14
gtgggaccca agtcgatgtt 20

<210> SEQ ID NO 15
<211> LENGTH: 646
<212> TYPE: DNA
<213> ORGANISM: Artificial Sequence
<220> FEATURE:
<223> OTHER INFORMATION: CAG promoter

<400> SEQUENCE: 15
actagttatt aatagtaatc aattacgggg tcattagttc atagcccata tatggagttc 60
cgcgttacat aacttacggt aaatggcccg cctggctgac cgcccaacga cccccgccca 120
ttgacgtcaa taatgacgta tgttcccata gtaacgccaa tagggacttt ccattgacgt 180
caatgggtgg agtatttacg gtaaactgcc cacttggcag tacatcaagt gtatcatatg 240
ccaagtacgc cccctattga cgtcaatgac ggtaaatggc ccgcctggca ttatgcccag 300
tacatgacct tatgggactt tcctacttgg cagtacatct acgtattagt catcgctatt 360
accatggtcg aggtgagccc cacgttctgc ttcactctcc ccatctcccc cccctcccca 420
cccccaattt tgtatttatt tattttttaa ttattttgtg cagcgatggg ggcggggggg 480
gggggggggc gcgcgccagg cggggcgggg cggggcgagg ggcggggcgg ggcgaggcgg 540
agaggtgcgg cggcagccaa tcagagcggc gcgctccgaa agtttccttt tatggcgagg 600
cggcggcggc ggcggcccta taaaaagcga agcgcgcggc gggcgg 646

<210> SEQ ID NO 16

<211> LENGTH: 1635
<212> TYPE: DNA
<213> ORGANISM: Artificial Sequence
<220> FEATURE:
<223> OTHER INFORMATION: omGNS

<400> SEQUENCE: 16
atgagactgc ctagcgccgc tggccccaga cccggcagac ctagaaggct gcctgccctg 60
ctgctgctgc ctctcctggg cggatgtctg ggccttgtgg gagccgctag aaggcccaac 120
gtgctgctgc tgctgacaga cgaccaggat gccgagctgg gcggcatgac ccccctgaaa 180
aagaccaagg ccctgatcgg cgagaagggc atgaccttca gcagcgccta cgtgcccagc 240
gccctgtgct gtcccagcag agccagcatc ctgaccggca agtacccccca caaccaccac 300 gtggtgaaca acaccctgga aggcaactgc agcagcaagg cctggcagaa gatccaagaa 360
ccctacacct tccccgccat cctgaagtcc gtgtgcggct accagacctt cttcgctggc 420
aagtacctga acgagtacgg cgctcccgac gctggcggcc tggaacatat ccccctgggc 480
tggtcctatt ggtacgccct ggaaaagaac agcaagtact acaactacac cctgagcatc 540
aacggcaagg ccagaaagca cggcgagaac tacagcgtgg actacctgac cgacgtgctg 600
gccaacctga gcctggactt cctggactac aagagcaaca gcgagccatt cttcatgatg 660
atcagcaccc ctgcccccca cagcccttgg acagccgccc ctcagtacca gaaagccttc 720
cagaacgtga tcgcccccag aaacaagaac ttcaacatcc acggcaccaa caagcactgg 780
ctgatcagac aggccaagac ccccatgacc aacagctcta tcagattcct ggacgacgcc 840
ttcaggcgga gatggcagac cctgctgtcc gtggacgacc tggtggaaaa gctggtgaaa 900
agactggaca gcaccggcga gctggacaac acctacatct tctacaccag cgacaacggc 960
taccacaccg gccagttcag cctgcccatc gacaagagac agctgtacga gttcgacatc 1020
aaggtgcccc tgctcgtgcg cggacccggc atcaagccca accagaccag caagatgctg 1080
gtgtccaaca tcgacctggg ccccaccatc ctggacctgg ccggctacga cctgaacaag 1140
acccagatgg acggcatgag cctgctgcct atcctgaagg gcgacagaaa cctgacctgg 1200
cgctctgacg tgctggtgga ataccagggc gagggcagaa acgtgaccga ccctacctgc 1260
cccagcctgt ctcctggcgt gtcccagtgc ttccccgact gtgtgtgcga ggacgcctac 1320
aacaacacat acgcctgcgt gcggaccctg agcagcctgt ggaacctgca gtactgcgag 1380
ttcgatgacc aagaagtgtt cgtcgaagtc tacaacatca ccgccgaccc cgaccagatc 1440
accaatatcg ccaagagcat cgaccccgag ctgctgggca agatgaacta cagactgatg 1500
atgctgcaga gctgcagcgg ccctacctgc agaacccctg gcgtgttcga ccccggctac 1560
agattcgacc tgagactgat gttcaactcc cacggcagcg tgcgcaccag aagattcagc 1620
aagcaccccc tgtga 1635

<210> SEQ ID NO 17
<211> LENGTH: 7887
<212> TYPE: DNA
<213> ORGANISM: Artificial Sequence
<220> FEATURE:
<223> OTHER INFORMATION: pAAV-CAG-omGNS

<400> SEQUENCE: 17
attacgccag ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctactcg 180

```
acattgatta ttgactagtt attaatagta atcaattacg gggtcattag ttcatagccc    240

atatatggag ttccgcgtta cataacttac ggtaaatggc ccgcctggct gaccgcccaa    300

cgacccccgc ccattgacgt caataatgac gtatgttccc atagtaacgc caatagggac    360

tttccattga cgtcaatggg tggagtattt acggtaaact gcccacttgg cagtacatca    420

agtgtatcat atgccaagta cgccccctat tgacgtcaat gacggtaaat ggcccgcctg    480

gcattatgcc cagtacatga ccttatggga ctttcctact tggcagtaca tctacgtatt    540

agtcatcgct attaccatgg tcgaggtgag ccccacgttc tgcttcactc tccccatctc    600

ccccccctcc ccacccccaa ttttgtattt atttattttt taattatttt gtgcagcgat    660

gggggcgggg gggggggggg ggcgcgcgcc aggcggggcg gggcggggcg aggggcgggg    720

cggggcgagg cggagaggtg cggcggcagc caatcagagc ggcgcgctcc gaaagtttcc    780

ttttatggcg aggcggcggc ggcggcggcc ctataaaaag cgaagcgcgc ggcgggcggg    840

agtcgctgcg ttgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagggc cctttgtgcg gggggagcgg ctcggggggt gcgtgcgtgt   1080

gtgtgtgcgt ggggagcgcc gcgtgcggct ccgcgctgcc cggcggctgt gagcgctgcg   1140

ggcgcggcgc ggggctttgt gcgctccgca gtgtgcgcga ggggagcgcg gccgggggcg   1200

gtgccccgcg gtgcgggggg ggctgcgagg ggaacaaagg ctgcgtgcgg ggtgtgtgcg   1260

tgggggggtg agcagggggt gtgggcgcgt cggtcgggct gcaacccccc ctgcaccccc   1320

ctccccgagt tgctgagcac ggcccggctt cgggtgcggg gctccgtacg gggcgtggcg   1380

cggggctcgc cgtgccgggc ggggggtggc ggcaggtggg ggtgccgggc ggggcggggc   1440

cgcctcgggc cggggagggc tcgggggagg ggcgcggcgg cccccggagc gccggcggct   1500

gtcgaggcgc ggcgagccgc agccattgcc ttttatggta atcgtgcgag agggcgcagg   1560

gacttccttt gtcccaaatc tgtgcggagc cgaaatctgg gaggcgccgc cgcacccccct   1620

ctagcgggcg cggggcgaag cggtgcggcg ccggcaggaa ggaaatgggc ggggagggcc   1680

ttcgtgcgtc gccgcgccgc cgtccccttc tccctctcca gcctcggggc tgtccgcggg   1740

gggacggctg ccttcggggg ggacggggca gggcggggtt cggcttctgg cgtgtgaccg   1800

gcggctctag agcctctgct aaccatgttc atgccttctt ctttttccta cagctcctgg   1860

gcaacgtgct ggttattgtg ctgtctcatc attttggcaa agaattgatt aattcgagcg   1920

aacgcgtgct agcgccacca tgagactgcc tagcgccgct ggccccagac ccggcagacc   1980

tagaaggctg cctgccctgc tgctgctgcc tctcctgggc ggatgtctgg gccttgtggg   2040

agccgctaga aggcccaacg tgctgctgct gctgacagac gaccaggatg ccgagctggg   2100

cggcatgacc cccctgaaaa agaccaaggc cctgatcggc gagaagggca tgaccttcag   2160

cagcgcctac gtgcccagcg ccctgtgctg tcccagcaga gccagcatcc tgaccggcaa   2220

gtacccccac aaccaccacg tggtgaacaa caccctggaa ggcaactgca gcagcaaggc   2280

ctggcagaag atccaagaac cctacacctt ccccgccatc ctgaagtccg tgtgcggcta   2340

ccagaccttc ttcgctggca agtacctgaa cgagtacggc gctcccgacg ctggcggcct   2400

ggaacatatc cccctgggct ggtcctattg gtacgccctg gaaaagaaca gcaagtacta   2460

caactacacc ctgagcatca acggcaaggc cagaaagcac ggcgagaact acagcgtgga   2520
```

-continued

```
ctacctgacc gacgtgctgg ccaacctgag cctggacttc ctggactaca agagcaacag   2580
cgagccattc ttcatgatga tcagcacccc tgccccccac agcccttgga cagccgcccc   2640
tcagtaccag aaagccttcc agaacgtgat cgcccccaga aacaagaact tcaacatcca   2700
cggcaccaac aagcactggc tgatcagaca ggccaagacc cccatgacca acagctctat   2760
cagattcctg gacgacgcct tcaggcggag atggcagacc ctgctgtccg tggacgacct   2820
ggtggaaaag ctggtgaaaa gactggacag caccggcgag ctggacaaca cctacatctt   2880
ctacaccagc gacaacggct accacaccgg ccagttcagc ctgcccatcg acaagagaca   2940
gctgtacgag ttcgacatca aggtgcccct gctcgtgcgc ggacccggca tcaagcccaa   3000
ccagaccagc aagatgctgg tgtccaacat cgacctgggc cccaccatcc tggacctggc   3060
cggctacgac ctgaacaaga cccagatgga cggcatgagc ctgctgccta tcctgaaggg   3120
cgacagaaac ctgacctggc gctctgacgt gctggtggaa taccagggcg agggcagaaa   3180
cgtgaccgac cctacctgcc ccagcctgtc tcctggcgtg tcccagtgct tccccgactg   3240
tgtgtgcgag gacgcctaca acaacacata cgcctgcgtg cggaccctga gcagcctgtg   3300
gaacctgcag tactgcgagt tcgatgacca agaagtgttc gtcgaagtct acaacatcac   3360
cgccgacccc gaccagatca ccaatatcgc caagagcatc gaccccgagc tgctgggcaa   3420
gatgaactac agactgatga tgctgcagag ctgcagcggc cctacctgca gaacccctgg   3480
cgtgttcgac cccggctaca gattcgacct gagactgatg ttcaactccc acggcagcgt   3540
gcgcaccaga agattcagca agcacccccct gtgatgagcg gccgcgaatt cgagctcggt   3600
acccgggaat caattcactc ctcaggtgca ggctgcctat cagaaggtgg tggctggtgt   3660
ggccaatgcc ctggctcaca aataccactg agatcttttt ccctctgcca aaaattatgg   3720
ggacatcatg aagccccttg agcatctgac ttctggctaa taaaggaaat ttattttcat   3780
tgcaatagtg tgttggaatt ttttgtgtct ctcactcgga aggacatatg ggagggcaaa   3840
tcatttaaaa catcagaatg agtatttggt ttagagtttg gcaacatatg cccatatgct   3900
ggctgccatg aacaaaggtt ggctataaag aggtcatcag tatatgaaac agccccctgc   3960
tgtccattcc ttattccata gaaaagcctt gacttgaggt tagatttttt ttatattttg   4020
ttttgtgtta tttttttctt taacatccct aaaattttcc ttacatgttt tactagccag   4080
atttttcctc ctctcctgac tactcccagt catagctgtc cctcttctct tatggagatc   4140
cctcgacctg cagcccaagc tgtagataag tagcatggcg ggttaatcat taactacaag   4200
gaacccctag tgatggagtt ggccactccc tctctgcgcg ctcgctcgct cactgaggcc   4260
gcccgggctt tgcccgggcg gcctcagtga gcgagcgagc gcgcagctgc attaatgaat   4320
cggccaacgc gcggggagag gcggtttgcg tattgggcgc tcttccgctt cctcgctcac   4380
tgactcgctg cgctcggtcg ttcggctgcg gcgagcggta tcagctcact caaaggcggt   4440
aatacggtta tccacagaat caggggataa cgcaggaaag aacatgtgag caaaaggcca   4500
gcaaaaggcc aggaaccgta aaaaggccgc gttgctggcg tttttccata ggctccgccc   4560
ccctgacgag catcacaaaa atcgacgctc aagtcagagg tggcgaaacc cgacaggact   4620
ataaagatac caggcgtttc cccctggaag ctccctcgtg cgctctcctg ttccgaccct   4680
gccgcttacc ggatacctgt ccgcctttct cccttcggga agcgtggcgc tttctcatag   4740
ctcacgctgt aggtatctca gttcggtgta ggtcgttcgc tccaagctgg gctgtgtgca   4800
cgaacccccc gttcagcccg accgctgcgc cttatccggt aactatcgtc ttgagtccaa   4860
cccggtaaga cacgacttat cgccactggc agcagccact ggtaacagga ttagcagagc   4920
```

-continued

```
gaggtatgta ggcggtgcta cagagttctt gaagtggtgg cctaactacg gctacactag   4980
aagaacagta tttggtatct gcgctctgct gaagccagtt accttcggaa aaagagttgg   5040
tagctcttga tccggcaaac aaaccaccgc tggtagcggt ggtttttttg tttgcaagca   5100
gcagattacg cgcagaaaaa aaggatctca agaagatcct ttgatctttt ctacggggtc   5160
tgacgctcag tggaacgaaa actcacgtta agggattttg gtcatgagat tatcaaaaag   5220
gatcttcacc tagatccttt taaattaaaa atgaagtttt aaatcaatct aaagtatata   5280
tgagtaaact tggtctgaca gttaccaatg cttaatcagt gaggcaccta tctcagcgat   5340
ctgtctattt cgttcatcca tagttgcctg actccccgtc gtgtagataa ctacgatacg   5400
ggagggctta ccatctggcc ccagtgctgc aatgataccg cgagacccac gctcaccggc   5460
tccagattta tcagcaataa accagccagc cggaagggcc gagcgcagaa gtggtcctgc   5520
aactttatcc gcctccatcc agtctattaa ttgttgccgg gaagctagag taagtagttc   5580
gccagttaat agtttgcgca acgttgttgc cattgctaca ggcatcgtgg tgtcacgctc   5640
gtcgtttggt atggcttcat tcagctccgg ttcccaacga tcaaggcgag ttacatgatc   5700
ccccatgttg tgcaaaaaag cggttagctc cttcggtcct ccgatcgttg tcagaagtaa   5760
gttggccgca gtgttatcac tcatggttat ggcagcactg cataattctc ttactgtcat   5820
gccatccgta agatgctttt ctgtgactgg tgagtactca accaagtcat tctgagaata   5880
gtgtatgcgg cgaccgagtt gctcttgccc ggcgtcaata cgggataata ccgcgccaca   5940
tagcagaact ttaaaagtgc tcatcattgg aaaacgttct tcggggcgaa aactctcaag   6000
gatcttaccg ctgttgagat ccagttcgat gtaacccact cgtgcaccca actgatcttc   6060
agcatctttt actttcacca gcgtttctgg gtgagcaaaa acaggaaggc aaaatgccgc   6120
aaaaaaggga ataagggcga cacggaaatg ttgaatactc atactcttcc tttttcaata   6180
ttattgaagc atttatcagg gttattgtct catgagcgga tacatatttg aatgtattta   6240
gaaaaataaa caaatagggg ttccgcgcac atttccccga aaagtgccac ctgacgtcta   6300
agaaaccatt attatcatga cattaaccta taaaaatagg cgtatcacga ggccctttcg   6360
tctcgcgcgt ttcggtgatg acggtgaaaa cctctgacac atgcagctcc cggagacggt   6420
cacagcttgt ctgtaagcgg atgccgggag cagacaagcc cgtcagggcg cgtcagcggg   6480
tgttggcggg tgtcggggct ggcttaacta tgcggcatca gagcagattg tactgagagt   6540
gcaccatatg cggtgtgaaa taccgcacag atgcgtaagg agaaaatacc gcatcaggcg   6600
attccaacat ccaataaatc atacaggcaa ggcaaagaat tagcaaaatt aagcaataaa   6660
gcctcagagc ataaagctaa atcggttgta ccaaaaacat tatgaccctg taatactttt   6720
gcgggagaag cctttatttc aacgcaagga taaaaatttt tagaaccctc atatatttta   6780
aatgcaatgc ctgagtaatg tgtaggtaaa gattcaaacg ggtgagaaag gccggagaca   6840
gtcaaatcac catcaatatg atattcaacc gttctagctg ataaattcat gccggagagg   6900
gtagctattt ttgagaggtc tctacaaagg ctatcaggtc attgcctgag agtctggagc   6960
aaacaagaga atcgatgaac ggtaatcgta aaactagcat gtcaatcata tgtaccccgg   7020
ttgataatca gaaaagcccc aaaaacagga agattgtata agcaaatatt taaattgtaa   7080
gcgttaatat tttgttaaaa ttcgcgttaa atttttgtta aatcagctca ttttttaacc   7140
aataggccga aatcggcaaa atcccttata aatcaaaaga atagaccgag atagggttga   7200
gtgttgttcc agtttggaac aagagtccac tattaaagaa cgtggactcc aacgtcaaag   7260
```

ggcgaaaaac cgtctatcag ggcgatggcc cactacgtga accatcaccc taatcaagtt 7320
ttttggggtc gaggtgccgt aaagcactaa atcggaaccc taaagggagc ccccgattta 7380
gagcttgacg gggaaagccg gcgaacgtgg cgagaaagga agggaagaaa gcgaaaggag 7440
cgggcgctag ggcgctggca agtgtagcgg tcacgctgcg cgtaaccacc acacccgccg 7500
cgcttaatgc gccgctacag ggcgcgtact atggttgctt tgacgagcac gtataacgtg 7560
ctttcctcgt tagaatcaga gcgggagcta aacaggaggc cgattaaagg gattttagac 7620
aggaacggta cgccagaatc ctgagaagtg tttttataat cagtgaggcc accgagtaaa 7680
agagtctgtc catcacgcaa attaaccgtt gtcgcaatac ttctttgatt agtaataaca 7740
tcacttgcct gagtagaaga actcaaacta tcggccttgc tggtaatatc cagaacaata 7800
ttaccgccag ccattgcaac ggaatcgcca ttcgccattc aggctgcgca actgttggga 7860
agggcgatcg gtgcgggcct cttcgct 7887

<210> SEQ ID NO 18
<211> LENGTH: 4306
<212> TYPE: DNA
<213> ORGANISM: Artificial Sequence
<220> FEATURE:
<223> OTHER INFORMATION: AAV9-CAG-omGNS

<400> SEQUENCE: 18
attacgccag ctgcgcgctc gctcgctcac tgaggccgcc cgggcaaagc ccgggcgtcg 60
ggcgaccttt ggtcgcccgg cctcagtgag cgagcgagcg cgcagagagg gagtggccaa 120
ctccatcact aggggttcct tgtagttaat gattaacccg ccatgctact tatctactcg 180
acattgatta ttgactagtt attaatagta atcaattacg gggtcattag ttcatagccc 240
atatatggag ttccgcgtta cataacttac ggtaaatggc ccgcctggct gaccgcccaa 300
cgacccccgc ccattgacgt caataatgac gtatgttccc atagtaacgc caatagggac 360
tttccattga cgtcaatggg tggagtattt acggtaaact gcccacttgg cagtacatca 420
agtgtatcat atgccaagta cgccccctat tgacgtcaat gacggtaaat ggcccgcctg 480
gcattatgcc cagtacatga ccttatggga ctttcctact tggcagtaca tctacgtatt 540
agtcatcgct attaccatgg tcgaggtgag ccccacgttc tgcttcactc tccccatctc 600
ccccccctcc ccacccccaa ttttgtattt atttattttt taattatttt gtgcagcgat 660
gggggcgggg gggggggggg ggcgcgcgcc aggcggggcg gggcggggcg aggggcgggg 720
cggggcgagg cggagaggtg cggcggcagc caatcagagc ggcgcgctcc gaaagtttcc 780
ttttatggcg aggcggcggc ggcggcggcc ctataaaaag cgaagcgcgc ggcgggcggg 840
agtcgctgcg ttgccttcgc cccgtgcccc gctccgccgc cgcctcgcgc cgcccgcccc 900
ggctctgact gaccgcgtta ctcccacagg tgagcgggcg ggacggccct tctcctccgg 960
gctgtaatta gcgcttggtt taatgacggc ttgtttcttt tctgtggctg cgtgaaagcc 1020
ttgaggggct ccgggagggc cctttgtgcg gggggagcgg ctcggggggt gcgtgcgtgt 1080
gtgtgtgcgt ggggagcgcc gcgtgcggct ccgcgctgcc cggcggctgt gagcgctgcg 1140
ggcgcggcgc ggggctttgt gcgctccgca gtgtgcgcga ggggagcgcg gccgggggcg 1200
gtgccccgcg gtgcgggggg ggctgcgagg ggaacaaagg ctgcgtgcgg ggtgtgtgcg 1260
tgggggggtg agcagggggt gtgggcgcgt cggtcgggct gcaacccccc ctgcaccccc 1320
ctccccgagt tgctgagcac ggcccggctt cgggtgcggg gctccgtacg gggcgtggcg 1380
cggggctcgc cgtgccgggc ggggggtggc ggcaggtggg ggtgccgggc ggggcggggc 1440

-continued

```
cgcctcgggc cggggagggc tcgggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcacccccct  1620
ctagcgggcg cggggcgaag cggtgcggcg ccggcaggaa ggaaatgggc ggggagggcc   1680
ttcgtgcgtc gccgcgccgc cgtccccttc tccctctcca gcctcggggc tgtccgcggg   1740
gggacggctg ccttcggggg ggacggggca gggcggggtt cggcttctgg cgtgtgaccg   1800
gcggctctag agcctctgct aaccatgttc atgccttctt ctttttccta cagctcctgg   1860
gcaacgtgct ggttattgtg ctgtctcatc attttggcaa agaattgatt aattcgagcg   1920
aacgcgtgct agcgccacca tgagactgcc tagcgccgct ggccccagac ccggcagacc   1980
tagaaggctg cctgccctgc tgctgctgcc tctcctgggc ggatgtctgg gccttgtggg   2040
agccgctaga aggcccaacg tgctgctgct gctgacagac gaccaggatg ccgagctggg   2100
cggcatgacc cccctgaaaa agaccaaggc cctgatcggc gagaagggca tgaccttcag   2160
cagcgcctac gtgcccagcg ccctgtgctg tcccagcaga gccagcatcc tgaccggcaa   2220
gtacccccac aaccaccacg tggtgaacaa caccctggaa ggcaactgca gcagcaaggc   2280
ctggcagaag atccaagaac cctacacctt ccccgccatc ctgaagtccg tgtgcggcta   2340
ccagaccttc ttcgctggca agtacctgaa cgagtacggc gctcccgacg ctggcggcct   2400
ggaacatatc cccctgggct ggtcctattg gtacgccctg gaaaagaaca gcaagtacta   2460
caactacacc ctgagcatca acggcaaggc cagaaagcac ggcgagaact acagcgtgga   2520
ctacctgacc gacgtgctgg ccaacctgag cctggacttc ctggactaca agagcaacag   2580
cgagccattc ttcatgatga tcagcacccc tgccccccac agcccttgga cagccgcccc   2640
tcagtaccag aaagccttcc agaacgtgat cgcccccaga aacaagaact tcaacatcca   2700
cggcaccaac aagcactggc tgatcagaca ggccaagacc cccatgacca acagctctat   2760
cagattcctg gacgacgcct tcaggcggag atggcagacc ctgctgtccg tggacgacct   2820
ggtggaaaag ctggtgaaaa gactggacag caccggcgag ctggacaaca cctacatctt   2880
ctacaccagc gacaacggct accacaccgg ccagttcagc ctgcccatcg acaagagaca   2940
gctgtacgag ttcgacatca aggtgcccct gctcgtgcgc ggacccggca tcaagcccaa   3000
ccagaccagc aagatgctgg tgtccaacat cgacctgggc cccaccatcc tggacctggc   3060
cggctacgac ctgaacaaga cccagatgga cggcatgagc ctgctgccta tcctgaaggg   3120
cgacagaaac ctgacctggc gctctgacgt gctggtggaa taccagggcg agggcagaaa   3180
cgtgaccgac cctacctgcc ccagcctgtc tcctggcgtg tcccagtgct tccccgactg   3240
tgtgtgcgag gacgcctaca acaacacata cgcctgcgtg cggaccctga gcagcctgtg   3300
gaacctgcag tactgcgagt tcgatgacca agaagtgttc gtcgaagtct acaacatcac   3360
cgccgacccc gaccagatca ccaatatcgc caagagcatc gaccccgagc tgctgggcaa   3420
gatgaactac agactgatga tgctgcagag ctgcagcggc cctacctgca gaacccctgg   3480
cgtgttcgac cccggctaca gattcgacct gagactgatg ttcaactccc acggcagcgt   3540
gcgcaccaga agattcagca agcacccccct gtgatgagcg gccgcgaatt cgagctcggt  3600
acccgggaat caattcactc ctcaggtgca ggctgcctat cagaaggtgg tggctggtgt   3660
ggccaatgcc ctggctcaca aataccactg agatcttttt ccctctgcca aaaattatgg   3720
ggacatcatg aagccccttg agcatctgac ttctggctaa taaaggaaat ttattttcat   3780
```

```
tgcaatagtg tgttggaatt ttttgtgtct ctcactcgga aggacatatg ggagggcaaa   3840

tcatttaaaa catcagaatg agtatttggt ttagagtttg gcaacatatg cccatatgct   3900

ggctgccatg aacaaaggtt ggctataaag aggtcatcag tatatgaaac agccccctgc   3960

tgtccattcc ttattccata gaaaagcctt gacttgaggt tagatttttt ttatattttg   4020

ttttgtgtta ttttttcttt taacatccct aaaattttcc ttacatgttt tactagccag   4080

atttttcctc ctctcctgac tactcccagt catagctgtc cctcttctct tatggagatc   4140

cctcgacctg cagcccaagc tgtagataag tagcatggcg ggttaatcat taactacaag   4200

gaacccctag tgatggagtt ggccactccc tctctgcgcg ctcgctcgct cactgaggcc   4260

gcccgggctt tgcccgggcg gcctcagtga gcgagcgagc gcgcag                  4306


<210> SEQ ID NO 19
<211> LENGTH: 20
<212> TYPE: DNA
<213> ORGANISM: Artificial Sequence
<220> FEATURE:
<223> OTHER INFORMATION: hGNS sense primer

<400> SEQUENCE: 19

aaactggtca agaggctgga                                                 20


<210> SEQ ID NO 20
<211> LENGTH: 20
<212> TYPE: DNA
<213> ORGANISM: Artificial Sequence
<220> FEATURE:
<223> OTHER INFORMATION: hGNS antisense primer

<400> SEQUENCE: 20

tggtttgatc ccaggtcctc                                                 20


<210> SEQ ID NO 21
<211> LENGTH: 20
<212> TYPE: DNA
<213> ORGANISM: Artificial Sequence
<220> FEATURE:
<223> OTHER INFORMATION: ohGNS-v1 sense primer

<400> SEQUENCE: 21

ccaacagcag catccagttt                                                 20


<210> SEQ ID NO 22
<211> LENGTH: 20
<212> TYPE: DNA
<213> ORGANISM: Artificial Sequence
<220> FEATURE:
<223> OTHER INFORMATION: ohGNS-v1 antisense primer

<400> SEQUENCE: 22

cgttgtcgct ggtgtagaag                                                 20


<210> SEQ ID NO 23
<211> LENGTH: 20
<212> TYPE: DNA
<213> ORGANISM: Artificial Sequence
<220> FEATURE:
<223> OTHER INFORMATION: ohGNS-v2  sense primer

<400> SEQUENCE: 23

ctgaagaaaa ccaaggcgct                                                 20
```

-continued

```
<210> SEQ ID NO 24
<211> LENGTH: 20
<212> TYPE: DNA
<213> ORGANISM: Artificial Sequence
<220> FEATURE:
<223> OTHER INFORMATION: ohGNS-v2 antisense primer

<400> SEQUENCE: 24

agttcccctc gagagtgttg                                          20


<210> SEQ ID NO 25
<211> LENGTH: 20
<212> TYPE: DNA
<213> ORGANISM: Artificial Sequence
<220> FEATURE:
<223> OTHER INFORMATION: ohGNS-v3 sense primer

<400> SEQUENCE: 25

aacttcaaca tccacggcac                                          20


<210> SEQ ID NO 26
<211> LENGTH: 20
<212> TYPE: DNA
<213> ORGANISM: Artificial Sequence
<220> FEATURE:
<223> OTHER INFORMATION: ohGNS-v3 antisense primer

<400> SEQUENCE: 26

actccagtct cttcaccagc                                          20


<210> SEQ ID NO 27
<211> LENGTH: 20
<212> TYPE: DNA
<213> ORGANISM: Artificial Sequence
<220> FEATURE:
<223> OTHER INFORMATION: human RPLPP0 sense primer

<400> SEQUENCE: 27

ctctggagaa actgctgcct                                          20


<210> SEQ ID NO 28
<211> LENGTH: 23
<212> TYPE: DNA
<213> ORGANISM: Artificial Sequence
<220> FEATURE:
<223> OTHER INFORMATION: human RPLPP0 antisense primer

<400> SEQUENCE: 28

ctgcacatca ctcaggattt caa                                      23
```

ADENOASSOCIATED VIRUS VECTORS FOR THE TREATMENT OF MUCOPOLYSACCHARIDOSES

FIELD OF THE INVENTION

The present invention relates to polynucleotides and vectors useful for the expression of proteins of interest and their utilization in gene therapy. The present invention also relates to vectors and nucleic acid sequences helpful for the treatment of mucopolysaccharidoses (MPS), and in particular, for the treatment of mucopolysaccharidoses type IIID or Sanfilippo D syndrome.

BACKGROUND OF THE INVENTION

The lysosome is an organelle found in the cytoplasm of animal cells that contains more than 50 hydrolases that break down biomolecules during the recycling of worn-out cellular components or after the engulfment of viruses and bacteria. This organelle contains several types of hydrolytic enzymes, including proteases, nucleases, glycosidases, lipases, phospholipases, phosphatases and sulfatases. All enzymes are acid hydrolases.

Lysosomal storage diseases (LSDs) are caused by genetic defects that affect one or more lysosomal enzymes. These genetic diseases result generally from a deficiency in a particular enzyme activity present in the lysosome. To a lesser extent, these diseases may be due to deficiencies in proteins involved in lysosomal biogenesis.

LSDs are individually rare, although as a group these disorders are relatively common in the general population. The combined prevalence of LSDs is approximately 1 per 5,000 live births. However, some groups within the general population are particularly afflicted by a high occurrence of LSDs. For instance, the prevalence of Gaucher and Tay-Sachs diseases in descendants from Jewish Central and Eastern European (Ashkenazi) individuals is 1 per 600 and 1 per 3,900 births, respectively.

The mucopolysaccharidoses (MPS) are a group of seven (I-VII) LSD diseases characterized by the absence or deficiency of a specific lysosomal enzyme involved in the metabolism of Glucosaminoglycans (GAGs). All MPS have an autosomal recessive pattern of inheritance, with the exception for MPSII (Hunter disease) that has a Xchromosomal linked inheritance.

Of the seven MPS, mucopolysaccharidosis type III (MPSIII or Sanfilippo syndrome) is the most common with a reported birth prevalence ranging from 0.28 and 4.1 per 100.000 births. This syndrome is caused by the deficiency of one of the enzymes involved in the degradation of the GAG heparan sulfate (HS). Four subtypes of Sanfilippo have been defined, each one caused by a deficiency in a different enzyme: type A (MPSIIIA), B (MPSIIIB), C (MPSIIIC) and D (MPSIIID). The genes coding these enzymes have been identified and various mutations have been reported.

MPSIIID is caused by the deficiency in the activity of the enzyme N-acetylglucosamine 6-sulfatase (GNS, EC 3.1.6.14). GNS catalyzes the hydrolysis of the 6-sulfate groups of the N-acetyl-D-glucosamine 6-sulfate units of HS. As a consequence of the sustained accumulation of non-degraded HS progressive cellular damage occurs, resulting in multisystemic disease. MPSIIID is the rarest form of the known MPSs, with only 31 patients described in the literature so far. Twenty-two different mutations have been identified in the human GNS gene leading to the deficiency of the activity of the GNS enzyme.

MPSIIID patients seem to follow the general pattern of clinical presentation of the Sanfilippo Syndrome, characterized by progressive central nervous system (CNS) degeneration and relatively mild somatic disease. After an early period of normal development the first signs of the disease usually manifest in the form of speech and developmental delay. This is followed by the appearance of other symptoms during infancy that may include progressive loss of psychomotor skills, speech loss, restless behavior, hyperactivity, sleep disorders, loss of contact with the environment and mental retardation. In addition to neurological symptoms, other non-neurological comorbidities such as upper respiratory tract infections, hirsutism, macrocephaly, hepatomegaly, reduced joint mobility and coarse facial features are also common among MPSIIID patients. In the end, MPSIIID evolves to a bedridden stage. The rate of disease progression and the phenotypic features present are highly variable between patients, with reported life expectancies ranging from as low as 14 years to the fourth decade. This variability may be related to multiple factors, such as the nature of the mutation, ethnicity or differences in the health care the patient receives.

To date there are no specific therapies for MPSIIID and control of the disease is symptomatic and aimed at improving the quality of life of patients and their families. As for other MPSs, two main therapeutic options have become available in the last few years: Enzyme Replacement Therapy (ERT) and hematopoietic stem cell transplantation (HSCT). The design of both therapeutic strategies relies on the possibility of cross-correction, based on the fact that normal cells secrete significant amounts of mannose-6-phosphate (M6P)-tagged soluble lysosomal enzymes, such as GNS, which can be subsequently taken up from the extracellular compartment by other cells via M6P receptors on the plasma membrane and targeted to the lysosomes. In addition, there is a threshold of residual enzymatic activity, generally very low, above which the cell is capable of coping with substrate influx and subjects are not affected by the disease, suggesting that restoration of normal activity is not a requisite to modify the clinical course.

For MPSIIID, ERT has been tested in a caprine model of the disease See Thompson, et al., J Inherit Metab Dis. 1992; 15(5):760-8. In this study a dose of 1 mg/Kg of recombinant caprine GNS (rcGNS) was administered intravenously to an MPSIIID goat at 2, 3 and 4 weeks of age. Five days after the last dose, a marked reduction in the lysosomal storage vacuoles and in the quantities of uronic acid (a constituent of the GAG HS) was observed in the liver, evidencing somatic correction by the infusion of rcGNS. Morphologic studies and the quantification of uronic acid showed no improvement in the CNS. Apart from this study, no other studies on the efficacy of ERT for MPSIIID have been conducted to date.

ERT with human recombinant enzyme is commercially available for MPS I, II and VI. Reported benefits of ERT include improvements in joint mobility, walking ability, pulmonary and respiratory functions along with reductions in urinary GAG excretion, and liver and spleen volumes when the enzyme is infused intravenously. However, due to hypersensitivity to the infused proteins, medical support has to be available during intravenous product administration. These anaphylactic reactions, that can compromise the patient's life, include respiratory distress, hypoxia, hypotension, urticaria and/or angioedema of throat or tongue and may require interventions such as resuscitation or emergency tracheotomy, and treatment with inhaled beta-adrenergic agonists, epinephrine or intravenous corticosteroids.

Other disadvantages of ERT include: 1) the difficulty of performing 1-3 hour-long intravenous infusions in paediatric patients, many of whom suffer from mental illness, 2) the fact that patients can become positive for antibodies to the enzyme of yet unknown clinical significance, but which might limit product efficacy in the long-term, and 3) the high cost of the therapy, which includes also the costs of home-care. Regardless of the safety concerns or the cost, at the recommended doses intravenous ERT is not capable of ameliorating MPS neurologic disease as the enzyme does not efficiently transit the blood brain-barrier (BBB).

An alternative to the intravenous delivery of ERT is the provision of the exogenous enzyme to the cerebrospinal fluid (CSF) in order to directly reach the CNS. Experiments in animal models of MPSIIIA, showed that the administration of the recombinant enzyme to the intrathecal space can penetrate the brain tissue and promote clearance of lysosomal storage material and ameliorate behaviour. Clinical trials to test intrathecal enzyme delivery have been conducted for MPSIIIA (NCT01155778) and MPSII (NCT00920647). Despite the potential benefits of intratechal ERT, the implantation of the permanent intrathecal drug delivery device that the therapy requires is associated with substantial risks and shortcomings and the therapy itself has a very high economic cost per patient/year.

Hematopoietic stem cell transplantation (HSCT) using bone marrow-derived stem cells (Bone marrow transplantation, BMT) has proven efficient in the treatment of both somatic and neurological pathology in patients with other MPSs. The principle underlying the correction by HSCT is that donor monocytes are able to cross the capillary wall, even at the BBB, after which they differentiate into tissue macrophages, microglia in the case of the CNS, and secrete the deficient enzyme for delivery to the various cells. However, bone marrow transplantation has proven unsuccessful in MPSIII patients, even if treated at pre-symptomatic stages, and it is not considered a therapeutic option for this disease. Regarding umbilical cord blood-derived stem cells transplantation it is yet unclear whether this approach results in protection of the CNS from degeneration in MPSIII patients.

Substrate deprivation therapy (SDT) aims at reducing the rate of GAG synthesis, so that, if any residual activity remains, this might be sufficient to prevent the excessive accumulation of GAGs or at least slow down the rate of accumulation. Genistein, a soybean isoflavone, has been suggested to act as an inhibitor of HS production by decreasing the kinase activity of the Epidermal Growth Factor receptor (EGFR). See Piotrowska E, et al., Eur J Hum Genet. 2006; 14(7):846-52. Recent studies indicate that genistein inhibits synthesis of GAGs in fibroblasts of patients suffering from various mucopolysaccharidoses (types I, II, IIIA and IIIB). See Piotrowska E, et al., supra. When administered intravenously, genistein is expected to be able to cross the BBB, permitting the treatment of the CNS pathology. Supporting this notion, an open label pilot study in which a genistein-enriched soybean extract was administered to 5 MPSIIIA and 5 MPSIIIB patients for 12 months resulted in a significant amelioration of both somatic and neurological parameters. However, subsequent studies neither showed improvement in disability scales nor in behaviour scores after administration of genistein to MPSIIIA, MPSIIIB and MPSIIIC patients for 12 months.

Given the limitations of current therapeutic options for MPSIIID, alternative approaches are needed. In vivo gene therapy offers the possibility of a one-time treatment for MPSIIID and other inherited diseases, with the prospect of lifelong beneficial effects.

Adenoassociated virus (AAV) vector-mediated gene transfer, in particular, is rapidly emerging as the approach of choice for many in vivo gene therapy applications, due to the high transduction efficiency and the lack of pathogenicity of these vectors. AAV vectors can transduce post-mitotic cells and several pre-clinical and clinical studies have demonstrated the potential of AAV vector-mediated gene transfer to efficiently drive sustained expression of therapeutic transgenes for a variety of diseases.

Several gene therapy approaches based on the use of AAVs have proved efficacious at ameliorating disease in mice models of MPSIII. Given the strong neurodegenerative component of these syndromes, the most relevant studies have focused on delivering therapeutic vectors to the CNS. Following pre-treatment with mannitol to permeate the BBB, a single intravenous infusion of AAV2 vectors coding for N-acetylglucosaminidase alpha (NAGLU) to a mouse model for MPSIIIB led to significantly extended survival, improved behavioural performance, and reduction of brain lysosomal pathology, although only partial correction of somatic pathology was achieved. See McCarty, et al., Gene Ther. 2009; 16(11):1340-52. Intravenously administered AAV9 vectors, capable of crossing the BBB, have recently proven efficacious at increasing enzymatic activity and promoting correction of lysosomal storage pathology in CNS and somatic organs, leading to improved behavioural performance and extension of lifespan in MPSIIIA and MPSIIIB mice models. Despite the doses required to achieve CNS correction are generally very high, a phase I/II clinical trial for MPSIIIA using AAV9 administered into a peripheral limb vein is currently ongoing (NCT02716246).

An alternative to reach the CNS is the administration of AAVs directly to the brain parenchyma. The stereotactic administration of AAV vectors into the brain has been tested in mouse and dog models of MPSIII. Due to the limited diffusion of AAVs from the site of injection, the approach requires multiple injections to improve vector biodistribution. Despite enzyme activity was detected throughout the brain of MPSIIIB dogs treated with 4 injections of AAV5 vectors encoding for NAGLU, lysosomal pathology was improved but not fully corrected, indicating that the levels of enzymatic activity achieved with this approach were insufficient to cope with GAG storage. MPSIIIA mice treated with AAVrh10 vectors encoding for sulfamidase and sulfatase-modifying Factor 1 (SUMF1) showed improved heparan sulfate catabolism and signs of decreased inflammation but only in areas restricted or close to the injection point. See Tardieu M, et al., Hum Gene Ther. 2014; 25(6): 506-16. Despite these limitations, two clinical trials are being conducted for MPSIIIA (NCT02053064) and MPSIIIB (ISRCTN19853672) using AAVrh10 and AAV5 vectors, respectively. The larger the brain the more difficult it becomes to cover the whole volume of the organ with intraparenchymal injections, and delivery to humans needs vector administration at several sites, making delivery technically challenging and requiring the development of specific surgical procedures.

Despite several therapeutic strategies have been developed for other forms of MPSIII, none of the aforementioned approaches has been applied to MPSIIID. Thus, there is a need for novel approaches for the treatment of MPSIIID.

SUMMARY OF THE INVENTION

The present invention provides new polynucleotides and vectors for the treatment of mucopolysaccharidoses, in particular mucopolysaccharidoses type III D (MPSIID), or Sanfilippo D syndrome.

In a first aspect, the present invention relates to a polynucleotide comprising an expression cassette wherein said expression cassette comprises a transcriptional regulatory region operatively linked to a nucleotide sequence encoding GNS protein or a functionally equivalent variant thereof.

In a second aspect, the present invention provides new vectors containing a polynucleotide according to the invention. In a particular embodiment, said vectors are new recombinant vectors for the treatment of mucopolysaccharidoses type IIID. Said recombinant vectors are in particular Adeno-associated Virus Vectors (AAV).

A further aspect of the present invention relates to a pharmaceutical composition comprising a therapeutically effective amount of the polynucleotide or the vector described herein.

Still, a further aspect of the invention relates to the polynucleotide of the invention or a vector described herein, or a pharmaceutical composition described herein for use as a medicament, in particular for the treatment of mucopolysaccharidoses type IIID.

The present invention also provides a method for the production of the adeno-associated viral vector according to the invention.

DEPOSIT OF MICROORGANISMS

Figure 1:
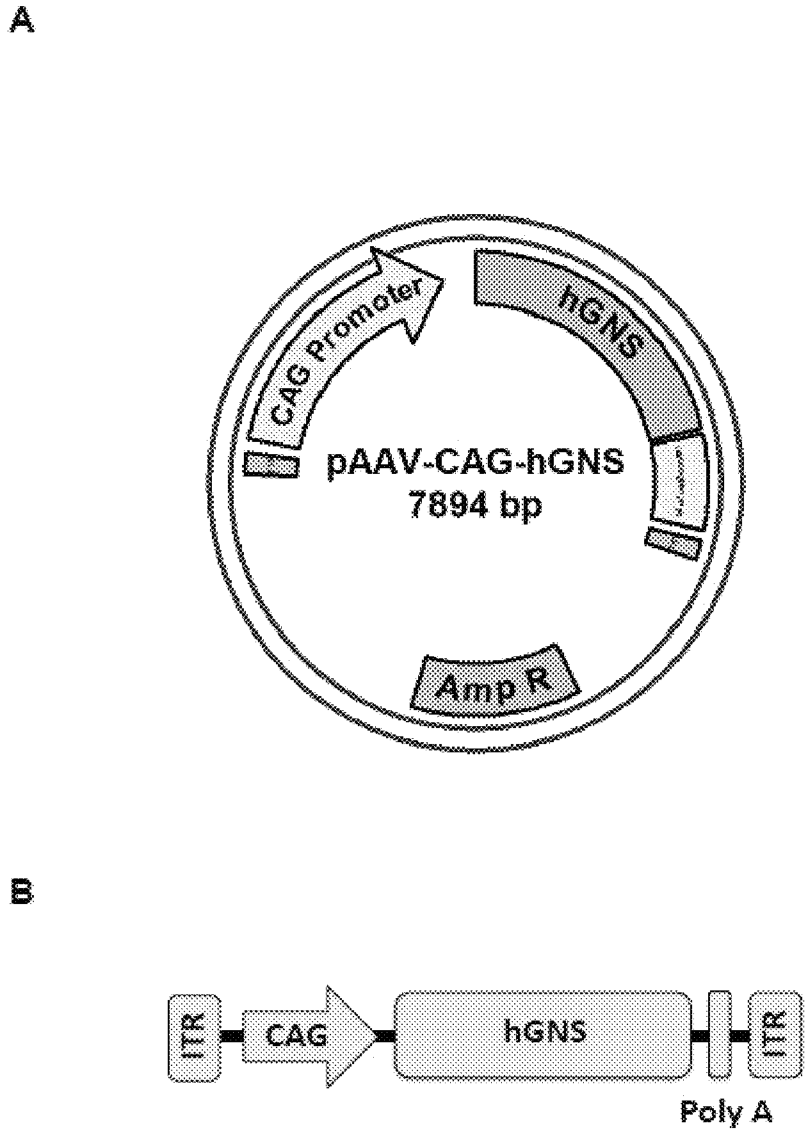
FIG. 1. Generation of pAAV-CAG-hGNS and AAV9-CAG-hGNS. (A) Schematic representation of the plasmid pAAV-CAG-hGNS and its components. (B) Schematic representation of the genome of an Adeno-associated vector containing the hGNS coding sequence.

The plasmids pAAV-CAG-hGNS (SEQ ID NO: 5), pAAV-CAG-ohGNS-version1 (SEQ ID NO: 6), pAAV-CAG-ohGNS-version2 (SEQ ID NO: 7) and pAAV-CAG-ohGNS-version3 (SEQ ID NO: 8) were deposited on Jul. 21, 2016 under access numbers DSM 32342, DSM 32343, DSM 32344 and DSM 32345 respectively at the DSMZ—Deutsche Sammlung von Mikroorganismen and Zellkulturen, Inhoffenstraße 7 B, D-38124 Braunschweig, Federal Republic of Germany.

Definitions

The terms "nucleotide sequence" or "isolated nucleotide sequence" or "polynucleotide sequence" or "polynucleotide" are interchangeably used herein and refer to a nucleic acid molecule, either DNA or RNA, containing deoxyribonucleotides or ribonucleotides respectively. The nucleic acid may be double stranded, single stranded, or contain portions of both double stranded or single stranded sequence.

The terms "% sequence identity", "% identity" or "% sequence homology" refer to the percentage of nucleotides or amino acids of a candidate sequence that are identical to the nucleotides or amino acids in the sequence of reference, after aligning the sequences to achieve the maximum % sequence identity. In a preferred embodiment, sequence identity is calculated based on the full length of two given SEQ ID NO or on part thereof. The % sequence identity can be determined by any methods or algorithms established in the art, such as the ALIGN, BLAST and BLAST 2.0 algorithms. See Altschul S, et al., Nuc Acids Res. 1977; 25:3389-3402 and Altschul S, et al., J Mol Biol. 1990; 215:403-410.

Herein, the "% sequence identity", "% identity" "or "% sequence homology" is calculated dividing the number of nucleotides or amino acids that are identical after aligning the sequence of reference and the candidate sequence, by the total number of nucleotides or amino acids in the sequence of reference and multiplying the result by 100.

Optionally, in determining the degree of amino acid similarity, the skilled person may also take into account the so-called "conservative" amino acid substitutions, as would be clear to the skilled person. Conservative amino acid substitutions are based on the interchangeability of residues having similar side chains. For example, the group of amino acids having aliphatic side chains includes glycine, alanine, valine, leucine, and isoleucine; the group of amino acids having aliphatic-hydroxyl side chains includes serine and threonine; the group of amino acids having amide-containing side chains includes asparagine and glutamine; the group of amino acids having aromatic side chains includes phenylalanine, tyrosine, and tryptophan; the group of amino acids having basic side chains includes lysine, arginine, and histidine; and the group of amino acids having sulphur-containing side chains includes cysteine and methionine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gin or His; Asp to Glu; Cys to Ser or Ala; Gin to Asn; Glu to Asp; Gly to Pro; His to Asn or Gin; He to Leu or Val; Leu to He or Val; Lys to Arg; Gin to Glu; Met to Leu or He; Phe to Met, Leu or Tyr; Ser to Thr; Thr to Ser; Trp to Tyr; Tyr to Trp or Phe; and, Val to He or Leu.

The terms "codify" or "coding" refer to the genetic code that determines how a nucleotide sequence is translated into a polypeptide or a protein. The order of the nucleotides in a sequence determines the order of amino acids along a polypeptide or a protein.

The term "protein" refers to a macromolecule composed of one or more linear chains of amino acids or polypeptides. Proteins can suffer post-translational modifications, like the conversion of a cysteine residue to 3-oxoalanine, glycosylation or metal binding. Glycosilation of a protein is the addition of different carbohydrates that are linked covalently to the amino acid chain.

The term "transcriptional regulatory region", as used herein, refers to a nucleic acid fragment capable of regulating the expression of one or more genes. The regulatory regions of the polynucleotides of the invention may include a promoter, plus response elements, activator and enhancer sequences for binding of transcription factors to aid RNA polymerase binding and promote expression, and operator or silencer sequences to which repressor proteins bind to block RNA polymerase attachment and prevent expression.

The term "promoter" must be understood as a nucleic acid fragment that functions to control the transcription of one or more polynucleotides e.g. coding sequences, which is placed 5' upstream of the polynucleotide sequence(s), and which is structurally identified by the presence of a binding site for DNA dependent RNA polymerase, transcription initiation sites and, but not limited to, binding sites for transcription factors, repressors, and any other nucleotide sequences known in the art to act directly or indirectly to regulate the amount of transcription from the promoter.

A promoter is said to be active or is said to drive the expression of a nucleotide sequence operatively linked to it when it can initiate transcription of said nucleotide sequence in an expression system using a gene construct comprising said promoter operably linked to a nucleotide sequence of interest using a suitable assay such a RT-qPCR or Northern blotting (detection of the transcript). The activity of said promoter may also be assessed at the protein level using a suitable assay for the encoded protein such as Western blotting or an ELISA. A promoter is said to be capable to initiate transcription if a transcript can be detected or if an increase in a transcript or protein level is found of at least 5%, 10%, 15%, 20%, 30%, 40%, 50%, 60%, 70%, 80%, 90%, 100%, 200%, 300%, 500%, 1000%, 1500% or 2000% as compared to transcription using a construct which only differs in that it is free of said promoter.

The term "constitutive" promoter refers to a promoter that is active under most physiological and developmental conditions. An "inducible" promoter is a promoter that is preferably regulated depending on physiological or developmental conditions. An inducible promoter may be active after drug delivery or light exposure. A "constitutive" promoter therefore is not regulated in the sense of an "inducible" promoter. A "tissue-specific" promoter is preferably active in specific types of cells/tissues. As opposed to a "tissue-specific" promoter, the promoter used in the context of the invention is a "ubiquitous" promoter. A ubiquitous promoter may be defined as a promoter that is active in many or in any different tissue(s). Usually, "many" in this context means more than 5 or at least 6, 10, 15, 20 or in 5, 6, 7, 8, 9, 10, 11, 12, 13, 14, 15, 16, 17, 18, 19, 20 different tissues.

The term "CAG" promoter refers to a promoter comprising the chicken β-actin promoter and cytomegalovirus enhancer (Alexopoulou A. et al. BMC Cell Biology 2008; 9(2): 1-11). More precisely, said CAG promoter comprises (i) the cytomegalovirus (CMV) early enhancer element, (ii) the chicken beta-actin promoter, (iii) the first intron of chicken beta-actin gene, and (iv) the intron 2/exon 3 of the rabbit beta-globin gene.

The term "operably linked" refers to the functional relation and the location of the promoter sequence with respect to the gene of interest (e.g. a promoter or enhancer is operably linked to a coding sequence if it affects the transcription of the sequence). Generally, a promoter operably linked is contiguous to the sequence of interest. However, an enhancer does not have to be contiguous to the sequence of interest to control its expression.

The term "post-transcriptional regulatory region", as used herein, refers to any polynucleotide that facilitates the expression, stabilization, or localization of the sequences contained in the cassette or the resulting gene product.

The term "vector", as used herein, refers to a construct capable of delivering, and optionally expressing, one or more polynucleotides of interest into a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. The vectors can be stable and can be self-replicating. There are no limitations regarding the type of vector that can be used. The vector can be a cloning vector, suitable for propagation and for obtaining polynucleotides, gene constructs or expression vectors incorporated to several heterologous organisms. Suitable vectors include prokaryotic expression vectors (e.g. pUC18, pUC19, Bluescript and their derivatives), mpl8, mpl9, pBR322, pMB9, ColEI, pCRI, RP4, phages and shuttle vectors (e.g. pSA3 and pAT28), and eukaryotic expression vectors based on viral vectors (e.g. adenoviruses, adeno-associated viruses as well as retroviruses and lentiviruses), as well as non-viral vectors such as pSilencer 4.1-CMV (Ambion®, Life Technologies Corp., Carslbad, Calif., US), pcDNA3, pcDNA3.1/hyg pHCMV/Zeo, pCR3.1, pEFI/His, pIND/GS, pRc/HCMV2, pSV40/Zeo2, pTRACER-HCMV, pUB6/V5-His, pVAXI, pZeoSV2, pCI, pSVL and pKSV-10, pBPV—I, pML2d and pTDTI.

The term "recombinant plasmid" or "plasmid" refers to a small, circular, double-stranded, self-replicating DNA molecule obtained through genetic engineering techniques capable of transferring genetic material of interest to a cell, which results in production of the product encoded by that said genetic material (e.g. a protein polypeptide, peptide or functional RNA) in the target cell. Furthermore, the term "recombinant plasmid" or "plasmid" also refers to a small, circular, double-stranded, self-replicating DNA molecule obtained through genetic engineering techniques used during the manufacturing of viral vectors as carriers of the recombinant vector genome.

The term "recombinant viral vector" or "viral vector" refers to an agent obtained from a naturally-occurring virus through genetic engineering techniques capable of transferring genetic material (e.g. DNA or RNA) of interest to a cell, which results in production of the product encoded by that said genetic material (e.g. a protein polypeptide, peptide or functional RNA) in the target cell.

The terms "adeno-associated virus", "AAV virus", "AAV virion," "AAV viral particle" and "AAV particle", used as synonyms herein, refer to a viral particle composed of at least one capsid protein of AAV (preferably composed of all capsid proteins of a particular AAV serotype) and an encapsulated polynucleotide corresponding to the AAV genome. The wild-type AAV refers to a virus that belongs to the genus Dependovirus, family Parvoviridae. The wild-type AAV genome is approximately 4.7 Kb in length and consists of a single stranded deoxyribonucleic acid (ssDNA) that can be positive or negative-sensed. The wild-type genome includes inverted terminal repeats (ITR) at both ends of the DNA strand, and three open reading frames (ORFs). The ORF rep encodes for four Rep proteins necessary for AAV lifecycle. The ORF cap contains nucleotide sequences encoding capsid proteins: VP1, VP2 and VP3, which interact to form a capsid of icosahedral symmetry. Finally, the AAP ORF, which overlaps with the Cap ORF, encodes for the AAP protein that appears to promote capsid assembly. If the particle comprises a heterologous polynucleotide (i.e. a polynucleotide different from a wild-type AAV genome, such as a transgene to be delivered to a mammalian cell) flanked by AAV ITRs, then it is typically known as "AAV vector particle" or "AAV viral vector" or "AAV vector". The invention also encompasses the use of double stranded AAV also called dsAAV or scAAV.

The term "adeno-associated virus ITRs" or "AAV ITRs", as used herein, refers to the inverted terminal repeats present at both ends of the DNA strand of the genome of an AAV. The ITR sequences are required for efficient multiplication of the AAV genome. Another property of these sequences is their ability to form a hairpin. This characteristic contributes to their self-priming, which allows the primase-independent synthesis of the second DNA strand. The ITRs have also been shown to be required for both integration of the wild-type AAV DNA into the host cell genome (e.g. in the human $19^{th}$ chromosome for serotype 2 AAV) and rescue from it, as well as for efficient encapsidation of the AAV DNA into a fully assembled, deoxyribonuclease-resistant AAV particle. The ITR sequences are about 145 bp in length. Preferably, the entire sequences of the ITRs are used in the genome of the AAV viral vector, although some degree of minor modification of these sequences is permissible. A wild-type ITR sequence may be altered by insertion, deletion or truncation, as long as the ITR mediates the desired functions, e.g. replication, nicking, virus packaging, integration, and/or provirus rescue, and the like. Procedures for modifying these ITR sequences are well known in the art. The ITR may be from any wild-type AAV, including but not limited to serotypes 1, 2, 3, 4, 5, 6, 7, 8, 9, 10, 11 or 12 or any other AAV known or later discovered. The AAV comprises two ITRs, which may be the same or different. Further, the two AAV ITRs can be from the same AAV serotype as the AAV capsid, or can be different. In a preferred embodiment, the 5' and 3' AAV ITRs derive from AAVI, AAV2, AAV4, AAV5, AAV7, AAV8 and/or AAV9 Preferably ITRs are from AAV2, AAV8 and/or AAV9 being AAV2 the most preferred. In one embodiment, the AAV2 ITRs are selected to generate a pseudotyped AAV (i.e. an AAV having capsid and ITRs derived from different serotypes).

The expression "recombinant viral genome", as used herein, refers to an AAV genome in which at least one extraneous polynucleotide is inserted into the naturally occurring AAV genome. The genome of the AAV according to the invention typically comprises the cis-acting 5' and 3' inverted terminal repeat sequences (ITRs) and an expression cassette.

The term "gene therapy" refers to the transfer of genetic material (e.g. DNA or RNA) of interest into a cell to treat or prevent a genetic or acquired disease or condition. The genetic material of interest encodes a product (e.g. a protein polypeptide, peptide or functional RNA) whose production in vivo is desired. For example, the genetic material of interest can encode an enzyme, hormone, receptor, or polypeptide of therapeutic value.

The term "transduce" or "transduction", as used herein, refers to the process whereby a foreign nucleotide sequence is introduced into a cell via a viral vector.

The term "transfection", as used herein, refers to the process of deliberately introducing purified nucleic acids by non-viral methods into eukaryotic cells.

The term "treat" or "treatment", as used herein, refers to the administration of a compound or composition of the invention to control the progression of a disease. Control of disease progression is understood as the achievement of the beneficial or desired clinical results that include, but are not limited to, reduction of the symptoms, reduction of the duration of the disease, stabilization of pathological states (specifically to avoid additional deterioration), delay of the progression of the disease, improvement in the pathological state, and remission (both partial and total). The control of progression of the disease also involves an extension of survival, compared with the expected survival if treatment is not applied.

The term "effective amount" refers to an amount of a substance sufficient to achieve the intended purpose. For example, an effective amount of an AAV9 vector to increase N-acetylglucosamine-6-sulfatase (GNS) activity is an amount sufficient to reduce glycosaminoglycan accumulation. A "therapeutically effective amount" of an expression vector to treat a disease or disorder is an amount of the expression vector sufficient to reduce or eradicate the signs and symptoms of the disease or disorder. The effective amount of a given substance will vary with factors such as the nature of the substance, the route of administration, the size and species of the animal to receive the substance and the purpose of giving the substance. The effective amount in each individual case may be determined empirically by a skilled artisan according to established methods in the art.

The term "individual" refers to a mammal, preferably human or non-human mammal, more preferably mouse, rat, other rodents, rabbit, dog, cat, pig, cow, horse or primate, further more preferably human.

DETAILED DESCRIPTION OF THE INVENTION

The present invention provides new polynucleotides and vectors for the treatment of mucopolysaccharidoses, in particular mucopolysaccharidoses type III (MPSIIID), or Sanfilippo D syndrome.

Thus, in a first aspect, the present invention relates to a polynucleotide (hereinafter referred to the "polynucleotide of the invention") comprising an expression cassette wherein said expression cassette comprises a transcriptional regulatory region operatively linked to a nucleotide sequence encoding the GNS protein or a functionally equivalent variant thereof.

As mentioned before, N-acetylglucosamine-6-sulfatase (GNS) is a lysosomal enzyme found in all cells. It is involved in the catabolism of the glycosaminoglycan (GAG) heparan sulfate (HS). This enzyme catalyzes the hydrolysis of the 6-sulfate groups of the N-acetyl-D-glucosamine 6-sulfate units of heparan sulfate. Deficiency of this enzyme results in the accumulation of undergraded substrate and the lysosomal storage disorder mucopolysaccharidosis type IIID (Sanfilippo D syndrome).

The invention also contemplates polynucleotide sequences encoding GNS variants and fragments known in the art. Thus, the invention should be construed to include DNA encoding functionally equivalent variants of GNS.

The term "functionally equivalent variant", as used herein, relates to any polypeptide substantially homologous to the sequence of GNS defined above and that preserves the biological activity of GNS. The sequence of such functional equivalent variants can be obtained from the sequence of GNS as defined above by means of insertion, substitution or deletion of one or more amino acids and which substantially preserves the biological activity of GNS. Methods for determining whether a variant preserves the biological activity of the native GNS are widely known to the skilled person and include any of the assays used in the experimental part of said application. Particularly, functionally equivalent variants of GNS encompassed by the present invention have at least one of the functions of GNS such as, for example, normalize or reduce glycosaminoglycan (GAG) levels, in particular, HS levels.

As shown in the Examples accompanying the present invention, optimized or non-optimized coding sequences of GNS have been used to treat MPSIIID animals. The results show a restoration of GNS activity after vector administration, which led to an almost complete normalization of the substrate accumulation (GAGs) characteristic of the disease in all central nervous system regions analysed in the animal models.

A method suitable for determining the ability to reduce or normalize GAG levels is detailed in the Examples section of the present invention.

In a preferred embodiment, a polypeptide is considered a functionally equivalent variant of GNS if it shows ability in the functions as mentioned above, particularly, if it is capable of hydrolyzing the 6-sulfate groups of the N-acetyl-D-glucosamine 6-sulfate units of heparan sulfate, with at least 10%, 20%, 30%, 40%, 50%, 60%, 70%, 80%, 90% or 100% of the ability of the GNS wild type polypeptide.

The functionally equivalent variants of GNS are polypeptides substantially homologous to the native GNS. The expression "substantially homologous", relates to a protein sequence when said protein sequence has a degree of identity with respect to the GNS wild type sequence of at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% o or at least 99%. The degree of identity between two polypeptides is determined using computer algorithms and methods that are widely known to the persons skilled in the art. The identity between two amino acid sequences is preferably determined by using the BLASTP algorithm [BLAST Manual, Altschul, S., et al, NCBI NLM NIH Bethesda, Md. 20894, Altschul, S., et al, J. Mol. Biol. 215: 403-410 (1990)], though other similar algorithms can also be used.

Functionally equivalent variants of GNS may be obtained by replacing nucleotides within its coding polynucleotide, accounting for codon preference in the host cell that is to be used to produce the GNS.

Functionally equivalent variants of GNS may be generated by making conservative amino acid changes and testing the resulting variant in one of the functional assays described above or other functional assays known in the art. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

In a particular embodiment of the invention, the nucleotide sequence encoding the GNS protein or a functionally equivalent variant thereof contained in the polynucleotide of the invention, has 70% to 85% identity with SEQ ID NO: 1. In a more particular embodiment, said nucleotide sequence has between 75% to 85% identity with SEQ ID NO: 1. In an even more preferred embodiment, said sequence has between 75% to 80% identity with SEQ ID NO: 1. In a preferred embodiment, said GNS nucleotide sequence is selected from the group consisting of SEQ ID NO: 2, SEQ ID NO: 3, and SEQ ID NO: 4.

In another embodiment of the invention the GNS protein encoded by the polynucleotide of the invention is selected from the group consisting of human GNS and mouse GNS.

The expression cassette which forms part of the polynucleotide of the invention may further comprises expression control sequences including, but not limited to, appropriate transcription regulatory sequences (i.e. initiation, termination, promoter, and enhancer), efficient RNA processing signals (e.g. splicing and polyadenylation (polyA) signals), sequences that stabilize cytoplasmic mRNA, sequences that enhance translation efficiency (i.e. Kozak consensus sequence), sequences that enhance protein stability, and when desired, sequences that enhance secretion of the encoded product. A great number of expression control sequences are known in the art and may be utilized according to the present invention.

According to the invention, the polynucleotide of the invention comprises an expression cassette wherein said expression cassette comprises a transcriptional regulatory region operatively linked to a nucleotide sequence encoding GNS. In a particular embodiment of the invention, said transcriptional regulatory region comprises a promoter. In another particular embodiment of the invention, the transcriptional regulatory region of the polynucleotide of the invention further comprises an enhancer operatively linked to the promoter. In a more particular embodiment, said promoter is a constitutive promoter. In a preferred embodiment, said promoter is the CAG promoter as set forth in SEQ ID NO:15.

In another embodiment, the expression cassette is flanked by AAV ITRs. In a more particular embodiment, said AAV ITRs are AAV2 ITRs.

The expression cassette of the polynucleotide of the invention comprises a nucleotide sequence encoding GNS or a functionally equivalent variant thereof. In an embodiment, said nucleotide sequence is the nucleotide sequence encoding human GNS, which corresponds to the sequence of the NCBI database with accession number NM_002076.3, more particularly it is SEQ ID NO: 1. In a preferred embodiment, the nucleotide sequence is a variant of the nucleotide sequence encoding human GNS, preferably is a sequence selected from the group consisting of SEQ ID NO: 2, SEQ ID NO: 3, and SEQ ID NO: 4.

In another embodiment, the expression cassette which forms part of the polynucleotide of the invention further comprises a post-transcriptional regulatory region. The term "post-transcriptional regulatory region", as used herein, refers to any polynucleotide that facilitates the expression, stabilization, or localization of the sequences contained in the cassette or the resulting gene product. The post-transcriptional regulatory region may be, without limitation, the Woodchuck Hepatitis Virus post-transcriptional region (WPRE). The term "woodchuck hepatitis B virus post-regulatory element" or "WPRE", as used herein, refers to a DNA sequence that, when transcribed, creates a tertiary structure capable of enhancing the expression of a gene.

In another embodiment, the expression cassette further comprises a polyadenylation signal.

The term "polyadenylation signal", as used herein, relates to a nucleic acid sequence that mediates the attachment of a polyadenine tail to the 3' terminus of the mRNA. Suitable polyadenylation signals include, without limitation, the SV40 early polyadenylation signal, the SV40 late polyadenylation signal, the HSV thymidine kinase polyadenylation signal, the protamine gene polyadenylation signal, the adenovirus 5 EIb polyadenylation signal, the bovine growth hormone polyadenylation signal, the human variant growth hormone polyadenylation signal, the rabbit beta-globin poly A signal and the like. In a particular embodiment, the polyadenylation signal is the rabbit beta-globin poly A signal or functional variants and fragments thereof.

The polynucleotide of the invention could be incorporated into a vector. Thus, in another aspect, the invention relates to a vector, herein referred to as "vector of the invention", containing the polynucleotide of the invention. In a particular embodiment, said vector is a plasmid. In another particular embodiment said vector is an AAV vector, said AAV vector containing a recombinant viral genome comprising a polynucleotide according to the invention.

All the embodiments disclosed in the context of the polynucleotide of the invention are also applicable to the vector of the invention.

In a more particular embodiment, said vector is selected from the group consisting of plasmid pAAV-CAG-hGNS, with accession number DSM 32342, as set forth in SEQ ID NO: 5, plasmid pAAV-CAG-ohGNS-version1, with accession number DSM 32343, as set forth in SEQ ID NO: 6, plasmid pAAV-CAG-ohGNS-version2 with accession number DSM 32344, as set forth in SEQ ID NO: 7, pAAV-CAG-ohGNS-version3 with accession number DSM 32345, as set forth in SEQ ID NO: 8.

In another particular embodiment, the invention refers to an adeno-associated viral vector, AAV vector, said AAV vector containing a recombinant viral genome wherein said recombinant viral genome comprises a polynucleotide comprising an expression cassette comprising a transcriptional regulatory region operatively linked to a nucleotide sequence encoding GNS or a functional equivalent variant thereof.

AAV according to the present invention include any serotype of the AAV known serotypes. In general, the different serotypes of AAV have genomic sequences with a significant homology, providing an identical series of genetic functions, produce virions that are essentially equivalent in physical and functional terms, and replicate and assemble through practically identical mechanisms. In particular, the AAV of the present invention may belong to the serotype 1 of AAV (AAV1), AAV2, AAV3 (including types 3A and 3B), AAV4, AAV5, AAV6, AAV7, AAV8, AAV9, AAV10, AAV11, avian AAV, bovine AAV, canine AAV, equine AAV, ovine AAV, and any other AAV. Examples of the sequences of the genome of the different AAV serotypes may be found in the literature or in public databases such as GenBank. See GenBank accession numbers AF028704.1 (AAV6), NC006260 (AAV7), NC006261 (AAV8), and AX753250.1 (AAV9). In a preferred embodiment, the AAV vector of the invention is of a serotype selected from the group consisting of the AAV2, AAV5, AAV7, AAV8, AAV9, AAV10 and AAVrh10 serotypes. In a preferred embodiment, said AAV vector of the invention is of serotype 9, AAV9.

In a particular embodiment said AAV vector contains a human or murine GNS sequence. In a more particular embodiment, the AAV vector according to the invention comprises a GNS encoding nucleotide sequence having 70% to 85% identity with SEQ ID NO: 1. In a more particular embodiment, said GNS encoding nucleotide sequence is selected from the group consisting of SEQ ID NO: 2, SEQ ID NO: 3, and SEQ ID NO: 4.

In a particular embodiment, the transcriptional regulatory region in the expression cassette comprises a promoter. In a more particular embodiment, said promoter is a constitutive promoter. In a more particular embodiment, said promoter is the CAG promoter as set forth in SEQ ID NO:15.

In another particular embodiment of the invention, the AAV vector is the AAV9-CAG-hGNS, SEQ ID NO:9, containing the nucleotide sequence SEQ ID NO: 1 linked to the CAG promoter. In another embodiment, the AAV vector is the AAV9-CAG-ohGNS-version1, SEQ ID NO:10 containing the nucleotide sequence SEQ ID NO: 2 linked to the CAG promoter. In another embodiment, the AAV is the AAV9-CAG-ohGNS-version2, SEQ ID NO:11 containing the nucleotide sequence SEQ ID NO: 3 linked to the CAG promoter. In another embodiment, the AAV vector is the AAV9-CAG-ohGNS-version3, SEQ ID NO:12 containing the nucleotide sequence SEQ ID NO: 4 linked to the CAG promoter.

In a preferred embodiment, the AAV of the invention contains a recombinant viral genome comprising a nucleotide sequence containing an expression cassette comprising in the 5' to 3' direction, (i) a 5' AAV2 ITR, (ii) a CMV immediate-early enhancer, (iii) a chicken B-actin promoter, (iv) the first intron of chicken beta-actin gene, (v) the intron 2/exon 3 from the rabbit beta-globin gene, (vi) the GNS cDNA or a functionally equivalent variant thereof, (vii) a poly A signal, such as the rabbit beta-globin poly A signal, and (viii) a 3' AAV2 ITR. Those skilled in the art will appreciate that the vector genome can comprise other sequences (e.g. intervening sequences between the sequences specifically described above). Components (i) to (v) have the meaning typically understood by the person skilled in the art.

In a preferred embodiment, the recombinant viral genome comprises the nucleotide sequence SEQ ID NO:9. Specifically, the 5' AAV ITR comprises nucleotides 1-120, the CMV enhancer comprises nucleotides 194-557, the B-actin promoter comprises nucleotides 558-839, the first intron of chicken beta-actin gene comprises nucleotides 840-1804, the intron 2/exon 3 from the rabbit beta-globin gene comprises nucleotides 1805-1906, the human GNS cDNA comprises nucleotides 1934-3592, the rabbit beta-globin poly A signal comprises nucleotides 3619-4147, and the 3' AAV2 ITR comprises nucleotides 4206-4313 of SEQ ID NO: 5.

In a preferred embodiment, the recombinant viral genome comprises the nucleotide sequence SEQ ID NO:10. Specifically, the 5' AAV ITR comprises nucleotides 1-120, the CMV enhancer comprises nucleotides 194-557, the B-actin promoter comprises nucleotides 558-839, the first intron of chicken beta-actin gene comprises nucleotides 840-1804, the intron 2/exon 3 from the rabbit beta-globin gene comprises nucleotides 1805-1906, the human GNS cDNA comprises nucleotides 1934-3592, the rabbit beta-globin poly A signal comprises nucleotides 3619-4147, and the 3' AAV2 ITR comprises nucleotides 4206-4313 of SEQ ID NO: 6.

In a preferred embodiment, the recombinant viral genome comprises the nucleotide sequence SEQ ID NO:11. Specifically, the 5' AAV ITR comprises nucleotides 1-120, the CMV enhancer comprises nucleotides 194-557, the B-actin promoter comprises nucleotides 558-839, the first intron of chicken beta-actin gene comprises nucleotides 840-1804, the intron 2/exon 3 from the rabbit beta-globin gene comprises nucleotides 1805-1906, the human GNS cDNA comprises nucleotides 1934-3592, the rabbit beta-globin poly A signal comprises nucleotides 3619-4147, and the 3' AAV2 ITR comprises nucleotides 4206-4313 of SEQ ID NO: 7.

In a preferred embodiment, the recombinant viral genome comprises the nucleotide sequence SEQ ID NO:12. Specifically, the 5' AAV ITR comprises nucleotides 1-120, the CMV enhancer comprises nucleotides 194-557, the B-actin promoter comprises nucleotides 558-839, the first intron of chicken beta-actin gene comprises nucleotides 840-1804, the intron 2/exon 3 from the rabbit beta-globin gene comprises nucleotides 1805-1906, the human GNS cDNA comprises nucleotides 1934-3592, the rabbit beta-globin poly A signal comprises nucleotides 3619-4147, and the 3' AAV2 ITR comprises nucleotides 4206-4313 of SEQ ID NO: 8.

Modified AAV sequences also can be used in the context of the present invention. Such modified sequences e.g. include sequences having at least about 70%, at least about 75%, at least about 80%, at least about 85%, at least about 90%, at least about 95% or more nucleotide and/or amino acid sequence identity (e.g. a sequence having about 75-99% nucleotide or amino acid sequence identity) to an AAV ITR or VP of any of the serotypes known and that maintain the function of said components. Assays for determining the function of AAV ITR or VP are known in the art. Said modified sequences can be used in place of wild-type AAV ITR or VP sequences.

The AAV vector of the invention comprises a capsid from any serotype. In general, the different AAV serotypes have genomic sequences of significant homology at the amino acid and the nucleic acid levels, providing an identical set of genetic functions, produce virions that are essentially equivalent in physical and functional terms, and replicate and assemble through practically identical mechanisms. In particular, the AAV of the present invention may belong to the serotype 1 of AAV (AAV1), AAV2, AAV3 (including types 3 A and 3B), AAV4, AAV5, AAV6, AAV7, AAV8, AAV9, AAV10, AAV11, avian AAV, bovine AAV, canine AAV, equine AAV, ovine AAV, and any other AAV. Examples of the sequences of the genome of the different AAV serotypes may be found in the literature or in public databases such as Gen Bank. See GenBank accession numbers AF028704.1 (AAV6), NC006260 (AAV7), NC006261 (AAV8), and AX753250.1 (AAV9). In a preferred embodiment, the adeno-associated viral vector of the invention is of a serotype selected from the group consisting of the of AAV2, AAV5, AAV7, AAV8, AAV9, AAV10 and AAVrh10 serotypes. In a more preferred embodiment, said AAV is AAV serotype 9, AAV9.

The genome of the AAV vector of the invention lacks the rep and cap open reading frames. Such AAV vectors can only be replicated and packaged into infectious viral particles in host cells that have been transfected with a vector encoding and expressing the rep and cap gene products (i.e. AAV Rep and Cap proteins), and wherein the host cells have been transfected with a vector which encodes and expresses a proteins from the adenovirus.

Pharmaceutical Compositions of the Invention

The polynucleotide, vector or AAV vector of the invention can be administered to the human or animal body by conventional methods, which require its formulation in a pharmaceutical composition. Thus, in a second aspect, the invention relates to a pharmaceutical composition (hereinafter referred to as "pharmaceutical composition of the invention") comprising a therapeutically effective amount of the polynucleotide of the invention, or the vector of the invention or the adeno-associated viral (AAV) vector of the invention. The pharmaceutical composition may further include a pharmaceutically acceptable carrier.

All the embodiments disclosed in the context of the polynucleotide of the invention or the vector of the invention or the AAV vector of the invention are also applicable to the pharmaceutical compositions of the invention.

The term "therapeutically effective amount" refers to the quantity of the polynucleotide, vector or AAV vector of the invention calculated to produce the desired effect and will generally be determined, among other reasons, by the own features of the polynucleotide, vector or AAV vector of the invention and the therapeutic effect to be obtained. Thus, said quantity that will be effective in the treatment of a disease can be determined by standard clinical techniques described herein or otherwise known in the art. The precise dose used in the formulation will depend on the administration route. The initial doses can be estimated from in vivo data (e.g. animal models) using techniques well known in the state of the art. Someone with normal experience in the state of the art can easily optimize administration to humans based on the data in animals.

In a particular embodiment, the dosage of the formulation can be measured or calculated as viral particles or as genome copies ("GC")/viral genomes ("vg").

Any method known in the art can be used to determine the genome copy (GC) number per milliliter of the viral compositions of the invention. One method for performing AAV GC number titration is as follows: purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting a specific region of the viral genome.

The terms "pharmaceutically acceptable carrier," "pharmaceutically acceptable diluent," "pharmaceutically acceptable excipient", or "pharmaceutically acceptable vehicle", used interchangeably herein, refer to a non-toxic solid, semisolid, or liquid filler, diluent, encapsulating material, or formulation auxiliary of any conventional type. A pharmaceutically acceptable carrier is essentially non-toxic to recipients at the employed dosages and concentrations and is compatible with other ingredients of the formulation. The number and the nature of the pharmaceutically acceptable carriers depend on the desired administration form. The pharmaceutically acceptable carriers are known and may be prepared by methods well known in the art.

The pharmaceutical composition can be formulated in accordance with routine procedures as a pharmaceutical composition adapted for intravenous, subcutaneous, intramuscular, intra-cerebrospinal fluid (CSF) e.g. intracisternal or intra-cerebroventricular, administration to human beings. In a preferred embodiment, the pharmaceutical composition is for intravenous or intra-cerebrospinal fluid (CSF) administration.

The AAV vector may be formulated for parenteral administration by injection (e.g. by bolus injection or continuous infusion). Formulations for injection may be presented in unit dosage form (e.g. in ampoules or in mono or multi-dose containers) with an added preservative. The viral compositions may take such forms as suspensions, solutions, or emulsions in oily or aqueous vehicles, and may contain formulatory agents such as suspending, stabilizing, or dispersing agents. Liquid preparations of the AAV formulations may be prepared by conventional means with pharmaceutically acceptable additives such as suspending agents (e.g. sorbitol syrup, cellulose derivatives or hydrogenated edible fats), emulsifying agents (e.g. lecithin or acacia), non-aqueous vehicles (e.g. almond oil, oily esters, ethyl alcohol or fractionated vegetable oils), and preservatives (e.g. methyl or propyl-p-hydroxybenzoates or sorbic acid). The preparations may also contain buffer salts. Alternatively, the compositions may be in powder form for constitution with a suitable vehicle (e.g. sterile pyrogen-free water) before use. When necessary, the composition may also include a local anaesthetic such as lidocaine to relieve pain at the injection site. When the composition is going to be administered by infiltration, it can be dispensed with an infiltration bottle which contains water or saline solution of pharmaceutical quality. When the composition is administered by injection, a water vial can be provided for injection or sterile saline solution, so that the ingredients can be mixed before administration. Preferably, the pharmaceutically acceptable carrier is saline solution and a detergent such as polyethylene-polyoxypropylene block copolymer, Pluronic F68®.

Compositions of the invention may be formulated for delivery to animals for veterinary purposes (e.g. livestock (cattle, pigs, others)), and other non-human mammalian subjects, as well as to human subjects. The pharmaceutical composition of the invention can be formulated with a physiologically acceptable carrier for use in gene transfer and gene therapy applications.

Also encompassed is the use of adjuvants in combination with or in admixture with the polynucleotide, vector or AAV vector of the invention. Adjuvants contemplated include, but are not limited to, mineral salt adjuvants or mineral salt gel adjuvants, particulate adjuvants, microparticulate adjuvants, mucosal adjuvants.

Adjuvants can be administered to a subject as a mixture with the polynucleotide, vector or AAV vector of the invention, or used in combination.

The pharmaceutical composition of the invention may be administered locally or systemically. In an embodiment, the pharmaceutical composition is administered near the tissue or organ whose cells are to be transduced. In a particular embodiment, the pharmaceutical composition of the invention is administered locally in the lateral ventricle. In another preferred embodiment, the pharmaceutical composition of the invention is administered systemically.

The term "systemically administered" and "systemic administration", as used herein, means that the polynucleotide, vectors, AAV vectors or compositions of the invention may be administered to a subject in a non-localized manner. The systemic administration may reach several organs or tissues throughout the body of the subject or may reach specific organs or tissues of the subject. For example, the intravenous administration may result in the transduction of more than one tissue or organ in a subject. The pharmaceutical compositions of the invention may be administered in a single dose or, in particular embodiments of the invention, multiple doses (e.g. two, three, four, or more administrations) may be employed to achieve a therapeutic effect.

Thus, in another aspect, the invention relates to a polynucleotide, a vector or an AAV vector according to the invention or a pharmaceutical composition according to the invention for use in medicine.

In a further aspect, the invention relates to a polynucleotide, a vector or an AAV vector according to the invention or a pharmaceutical composition according to the second aspect of the invention for use in the treatment of mucopolysaccharidosis type IIID.

Thus, in another aspect, the invention relates to a polynucleotide, a vector or an AAV vector according to the invention or a pharmaceutical composition according to the invention for increasing N-acetylglucosamine-6-sulfatase activity.

In another aspect, the invention provides a method for the treatment and/or prevention of a mucopolysaccharidosis type IIID in a subject in need thereof which comprises the administration to said subject of a polynucleotide according to the invention, or the vector according the invention, or the recombinant vector according to the invention or a pharmaceutical composition according to the invention.

The terms "prevent," "preventing," and "prevention", as used herein, refer to inhibiting the inception or decreasing the occurrence of a disease in a subject. Prevention may be complete (e.g. the total absence of pathological cells in a subject) or partial. Prevention also refers to a reduced susceptibility to a clinical condition. The term "treat" or "treatment", as used herein, refers to the administration of a polynucleotide, or vector or AAV vector or a pharmaceutical composition of the invention to control the progression of a disease after its clinical signs have appeared. Control of the disease progression is understood to mean the achievement of the beneficial or desired clinical results that include, but are not limited to, reduction of the symptoms, reduction of the duration of the disease, stabilization of pathological states (specifically to avoid additional deterioration), delay of the progression of the disease, improvement of the pathological state, and remission (both partial and total). The control of progression of the disease also involves an extension of survival, compared with the expected survival if treatment is not applied.

The term "subject", as used herein, refers to an individual or animal, such as a human being, a non-human primate (e.g. chimpanzees and other apes and monkey species), a farm animal (e.g. birds, fish, cattle, sheep, pigs, goats, and horses), a domestic mammal (e.g. dogs and cats), or a laboratory animal (e.g. rodents, such as mice, rats and guinea pigs). The term includes a subject of any age or sex. In a preferred embodiment the subject is a mammal, preferably a human being.

Methods for Obtaining the AAVs of the Invention

The invention also relates to a method for obtaining the AAV vectors of the invention. Said AAV vectors can be obtained by introducing the polynucleotides of the invention into cells that express the Rep and Cap proteins constitutively or wherein the Rep and Cap coding sequences are provided in plasmids or vectors.

Thus, in another aspect, the invention relates to a method for obtaining an AAV vector comprising the steps of:

(i) providing a cell comprising a polynucleotide of the invention, AAV cap proteins, AAV rep proteins and, optionally, viral proteins upon which AAV is dependent for replication, (ii) maintaining the cell under conditions adequate for assembly of the AAV and (iii) purifying the adeno-associated viral vector produced by the cell.

Any cell capable of producing AAV vectors can be used in the present invention.

The polynucleotide of the invention used in this method has been described previously. Any of the embodiments disclosed in the context of the polynucleotides of the invention is applicable in the context of the methods for obtaining AAV of the invention.

The term "cap protein", as used herein, refers to a polypeptide having at least one functional activity of a native AAV cap protein (e.g. VPI, VP2, VP3). Examples of functional activities of cap proteins include the ability to induce formation of a capsid, facilitate accumulation of single-stranded DNA, facilitate AAV DNA packaging into capsids (i.e. encapsidation), bind to cellular receptors, and facilitate entry of the virion into host cells. In principle, any cap protein can be used in the context of the present invention.

In a preferred embodiment, the cap proteins are derived from AAV9.

The term "capsid", as used herein, refers to the structure in which the viral genome is packaged. A capsid consists of several oligomeric structural subunits made of proteins. For instance, AAV have an icosahedral capsid formed by the interaction of three capsid proteins: VP1, VP2 and VP3.

The term "rep protein", as used herein, refers to a polypeptide having at least one functional activity of a native AAV rep protein. A "functional activity" of a rep protein is any activity associated with the physiological function of the protein, including facilitation of replication of DNA through recognition, binding and nicking of the AAV origin of DNA replication as well as DNA helicase activity. Additional functions include modulation of transcription from AAV (or other heterologous) promoters and site-specific integration of AAV DNA into a host chromosome. In a particular embodiment, AAV rep genes derive from the serotype AAV2.

The expression "viral proteins upon which AAV is dependent for replication", as used herein, refers to polypeptides which perform functions upon which AAV is dependent for replication (i.e. "helper functions"). The helper functions include, without limitation, those functions required for activation of AAV gene transcription, stage specific AAV mRNA splicing, AAV DNA replication, synthesis of cap proteins, and AAV capsid assembly. Viral-based accessory functions can be derived from any of the known helper viruses such as adenovirus, herpesvirus (other than herpes simplex virus type-1), and vaccinia virus. Helper functions include, without limitation, adenovirus EI, E2a, VA, and E4 or herpesvirus UL5, UL8, UL52, and UL29, and herpesvirus polymerase.

The polynucleotide of the invention, or the genes AAV rep, AAV cap and genes providing helper functions can be introduced into the cell by incorporating said genes into a vector such as, for example, a plasmid, and introducing said vector into the cell. The genes can be incorporated into the same plasmid or into different plasmids. In a preferred embodiment, the polynucleotide of the invention is incorporated in one plasmid, the AAV rep and cap genes are incorporated into another plasmid and the genes providing helper functions are incorporated into a their plasmid.

The plasmids containing the polynucleotide of the invention and or the AAV rep and cap genes or genes providing helper functions can be introduced into the cell by using any suitable method well known in the art. Examples of transfection methods include, but are not limited to, co-precipitation with calcium phosphate, DEAE-dextran, polybrene, electroporation, microinjection, liposome-mediated fusion, lipofection, retrovirus infection and biolistic transfection. In a particular embodiment, the transfection is carried out by means of co-precipitation with calcium phosphate. When the cell lacks the expression of any of the AAV rep and cap genes and genes providing adenoviral helper functions, said genes can be introduced into the cell simultaneously with the polynucleotide of the invention. Alternatively, said genes can be introduced in the cell before or after the introduction of the polynucleotide of the invention.

In a particular embodiment, the cells are transfected simultaneously with three plasmids, i) a plasmid comprising the polynucleotide of the invention, ii) a plasmid comprising the AAV rep and cap genes and iii) a plasmid comprising the genes providing the helper functions.

Step (ii) of the method of the invention involves maintaining the cell under conditions adequate for assembly of the AAV.

Methods of culturing cells and exemplary conditions which promote the release of AAV vector particles, such as the lysing of the cells, may be carried out as described in examples herein. Producer cells are grown for a suitable period of time in order to promote the assembly of the AAV and the release of viral vectors into the media. Generally, time of culture is measured from the point of viral production. For example, in the case of AAV, viral production generally begins upon supplying helper virus function in an appropriate producer cell as described herein.

Step (iii) of the method of the invention involves purifying the AAV vector produced by the cell.

Any method for the purification of the AAV from said cells or said culture medium can be used for obtaining the AAV of the invention. In a particular embodiment, the AAV of the invention are purified following an optimized method based on a polyethylene glycol precipitation step and two consecutive cesium chloride (CsCl) gradients.

Various naturally occurring and engineered AAV, their encoding nucleic acids, AAV cap and rep proteins, as well as methods for isolating or generating, propagating, and purifying such AAV, and in particular, their capsids, suitable for use in production of AAV are known in the art.

The present invention further provides an isolated cell comprising the polynucleotide sequence of the invention encoding the GNS protein or a functionally equivalent variant thereof.

All the embodiments disclosed in the context of the polynucleotides, vectors or AAV vectors of the invention and the pharmaceutical compositions of the invention are applicable to the therapeutic methods of the invention.

General Procedures

1. Recombinant AAV Vectors

The AAV vectors described herein were obtained by triple transfection. The materials required for making the vectors were: HEK293 cells (expressing adenoviral E1 genes), helper plasmid providing adenovirus functions, plasmid providing AAV rep genes from serotype 2 and cap genes from serotype 9 (AAV9) and, finally, the backbone plasmid with AAV2 ITRs and the construct of interest.

To generate glucosamine (N-acetyl)-6-sulfatase-expressing AAV vectors, the optimized or non-optimized coding sequences of human or murine glucosamine (N-acetyl)-6-sulfatase were cloned into an AAV backbone plasmid under the control of the ubiquitous hybrid CAG promoter. Large-scale production of plasmids was done using an EndoFree Plasmid Megaprep Kit (Qiagen).

Vectors were generated by helper virus-free transfection of HEK293 cells using three plasmids with modifications. See Matsushita T, et al., Gene Ther. 1998; 5:938-945 and Wright J, et al., Mol. Ther. 2005; 12:171-178. Cells were cultured to 70% confluence in roller bottles (RB) (Corning, Corning, N.Y., US) in DMEM supplemented with 10% FBS and then co-transfected with: 1) a plasmid carrying the expression cassette flanked by the viral ITRs of serotype 2 AAV (described above); 2) a plasmid carrying the AAV rep2 and the cap9 genes; and 3) a plasmid carrying the adenovirus helper functions. Vectors were purified by two consecutives cesium chloride gradients using an optimized protocol as previously described. See Ayuso E, et al., Gene Ther. 2010; 17:503-510. Vectors were dialyzed against PBS+0.001% Pluronic® F68, filtered, titred by qPCR and stored at −80° C. until use.

The vectors of the present invention were constructed according to molecular biology techniques well known in the art.

2. In Vitro Transfection Studies

HEK293 cells were transfected with 4 μg of pAAV-CAG-hGNS, pAAV-CAG-ohGNS-v1, pAAV-CAG-ohGNS-v2 or pAAV-CAG-ohGNS-v3 using Lipofectamine® 2000 (Invitrogen, Thermo Fisher Scientific, Calif., USA) following the manufacturer's instructions. After 48 hours, cells and culture media were harvested and processed for RNA and protein extraction.

Total RNA was obtained using the RNeasy Mini Kit (Quiagen, Hilden, Germany), following the manufacturer's instructions, and retrotranscribed with the Transcriptor First Strand cDNA Synthesis Kit (Roche). Expression of the different versions of the human GNS gene was assessed through quantitative real-time PCR using primers specific for hGNS (SEQ ID NO: 19: Fw: 5' AAA CTG GTC AAG AGG CTG GA 3', SEQ ID NO: 20: Rv: 5' TGG TTT GAT CCC AGG TCC TC 3'), ohGNS-v1 (SEQ ID NO: 21: Fw: 5' CCA ACA GCA GCA TCC AGT TT 3', SEQ ID NO: 22: Rv: 5' CGT TGT CGC TGG TGT AGA AG 3'), ohGNS-v2 (SEQ ID NO: 23: Fw: 5' CTG AAG AAA ACC AAG GCG CT 3', SEQ ID NO: 24: Rv: 5' AGT TCC CCT CGA GAG TGT TG 3') and ohGNS-v3 (SEQ ID NO: 25: Fw: 5' AAC TTC AAC ATC CAC GGC AC 3', SEQ ID NO: 26: Rv: ACT CCA GTC TCT TCA CCA GC 3'). Values were normalized to the expression of human RPLPP0 (SEQ ID NO: 27: Fw: 5' CTC TGG AGA AAC TGC TGC CT 3', SEQ ID NO: 28: Rv: 5' CTG CAC ATC ACT CAG GAT TTC AA 3'). Real-time PCR was performed in a Light Cycler® 480 (Roche, Manheim, Germany) using the Light Cycler® 480 SYBRgreen I Master (Roche, Mannheim, Germany).

Protein extracts were obtained by sonication of cells in 250 μl of Mili-Q water and protein content was quantified using Bradford protein assay (Bio-Rad, Hercules, Calif., US). N-acetylglucosamine 6-sulfatase activity was determined in 5 μg of cell protein extracts and 5 μl of culture media and normalized by total amount of protein and volume, respectively, with a 4-methylumbelliferone-derived fluorogenic substrate (Moscerdam Substrates, Oegstgeest, NL), as described previously. See Wang He et al., J Inher Metab Diss 1993; 16:935-941.

3. Animals

C57BL/6N-A/a embryonic stem cells carrying a reporter (LacZ) gene tagged insertion in the Gns gene available through the International Mouse Phenotyping Consortium (IMPC, www.mousephenotype.org) were obtained. Clones were microinjected in C57BL/6J blastocytes in the Transgenic Animal Unit of the Center of Animal Biotechnology and Gene Therapy (CBATEG) at Universitat Autònoma de Barcelona (UAB), and the resulting male chimeras were bred with C57Bl/6N females to generate Gns knock-out offspring. Genotype was determined on genomic DNA from tail-clipped samples with a PCR analysis that amplifies a sequence encompassing the targeted mutation. The sequences of the respective sense and antisense primers were: Sense primer: 5'-CCACACAGGGCAGTTCTCTT-3' (SEQ ID NO: 13). Antisense primer: 5'-GTGGGACCCAAGTCGATGTT-3' (SEQ ID NO: 14). Mice were fed ad libitum with a standard diet (Harlan, Tekland) and maintained under a light-dark cycle of 12 h (lights on at 9:00 A.M.).

Due to the lack of GNS activity these animals show as early as two-months of age several pathological features characteristic of MPSIIID disease, including accumulation of GAGs and enlargement of the lysosomal compartment in different regions of the brain and peripheral organs such as liver, heart, spleen, lung and kidney. Neuroinflammation is detected in different areas of the brain as revealed by the presence of microgliosis and astrogliosis. Furthermore, many of these pathological findings are exacerbated when animals are 6 months old, suggesting worsening of the pathology as animals age. Accordingly, $Gns^{-/-}$ mice behave normally at 2 months of age but show hypoactive behaviour at 6 months. Finally, MPSIIID mice have shortened lifespan.

4. Vector Administration to Mice

For intravenous vector delivery, $1\times10^{10}$ vector genomes of AAV9 vectors baring different versions of the human glucosamine (N-acetyl)-6-sulfatase coding sequence were delivered to mice in a total volume of 200 μl through tail vein injection. WT and non-treated $Gns^{-/-}$ animals were used as controls. For intra-CSF delivery of AAV9-CAG-omGNS vectors to mice, a total dose of $5\times10^{10}$ vg were injected to the cisterna magna of 2-month-old $Gns^{-/-}$ animals. A similar cohort of animals was injected with $5\times10^{10}$ vg control non-coding (AAV9-null) vector. At 6, 12 and 22 months of age, i.e. 4, 10 and 20 months post vector administration, mice were sacrificed and tissues were harvested.

5. Sample Collection

At sacrifice, animals were deeply anesthetized and then transcardially perfused with 12 ml of PBS to completely clear blood from tissues. The entire brain and multiple somatic tissues (including liver, spleen, kidney, lung, heart and adipose tissue) were collected and either frozen in liquid nitrogen and stored at −80° C. or immersed in formalin for subsequent histological analyses.

6. N-acetylglucosamine 6-sulfatase Activity and Glycosaminoglycan Quantification Liver and brain samples were sonicated in Mili-Q water. N-acetylglucosamine 6-sulfatase activity was determined with a 4-methylumbelliferone-derived fluorogenic substrate (Moscerdam Substrates, Oegstgeest, NL), as described previously. See Wang He et al., J Inher Metab Diss 1993; 16:935-941. Brain and liver activity levels were normalized against the total amount of protein, quantified using Bradford protein assay (Bio-Rad, Hercules, Calif., US).

For glycosaminoglycan (GAG) quantification, tissue samples were weighted and then digested with proteinase K and extracts were clarified by centrifugation and filtration. GAG levels were determined in tissue extracts with the Blyscan sulfated glycosaminoglycan kit (Biocolor, Carrickfergus, County Antrim, GB), using chondroitin 4-sulfate as standard. The levels of GAG were normalized to wet tissue weight.

7. Activity of Other Lysosomal Enzymes

Brain and liver samples were sonicated in 500 μl of Mili-Q water and enzyme activities were determined in supernatants using 4-methylumbelliferone-derived fluorogenic substrates. IDUA activity was assayed in 15 μg of protein incubated for 1 h at 37° C. with 4-methylumbelliferyl α-L-iduronide (Glycosynth). See Bacter et al., Blood 2002; 99(5)1857-9. SGSH activity was measured as previously described. See Karpova et al., J Inherit Metab Dis. 1996; 19(3):278-285, Haurigot V, et al., J Clin Invest. 2013; 1; pii:66778. Briefly, 30 μg of protein were first incubated with 4-MU-αGlcNS for 17 hours at 47° C. The second incubation was carried out in the presence of 10 U/ml of α-glucosidase (Sigma-Aldrich) in 0.2% BSA for 24 hours at 37° C. For NAGLU activity, 30 μg of tissue protein extract were incubated with 4-methylumbelliferyl-α-N-acetyl-D-glucosaminide (Moscerdam Substrates) for 3 h at 37° C., as previously described. See Marsh et al., Clin Genet. 1985; 27(3):258-62, Ribera A, et al., Hum Mol Genet. 2015; 24(7):2078-95.

HGSNAT activity was determined from 30 μg of protein extract incubated with Acetylcoenzyme A and 4-methylumbelliferyl-β-D-glucosamine (MU-$\beta GlcNH_2$) Moscerdam Substrates) for 17 h at 37° C. See Voznyi et al., J Inh Metab Dis 1993; 16:465-72. GALNS activity was assayed by a 2-step protocol using 10 μg of protein extract and 4-Methylumbelliferyl β-D-Galactopyranoside-6-sulfate Sodium Salt (MU-βGal-6S) during the first incubation for 17 h at 37° C. The second step was carried out adding $P_i$-buffer (0.9M $Na_2HPO_4$/0.9M $NaH_2PO_4$ buffer, pH4.3+0.02% (w/v) Na-azide) and β-Galactosidase (β-Gal-Ao, Sigma) and incubating the mix for 2 h at 37° C. See van Diggelen et al., Clin Chim Acta 1990; 187:131-40. The activity of GUSB enzyme was determined from 10 μg of protein extract incubated with 4-methylumbelliferyl-β-D-glucuronide (Sigma) at 37° C. for 1 h. HEXB activity was assayed by incubation of 0.1 μg of protein extract with 4-methylumbelliferyl N-acetyl-β-D-glucosaminide (Sigma) for 1 h at 37° C. After stopping reactions by increasing the pH, released fluorescence was measured with FLx800 fluorimeter (BioTek Instruments). All brain and liver activities levels were normalized against the total amount of protein, quantified using Bradford protein assay (Bio-Rad, Hercules, Calif., US).

8. Histological Analysis

Tissues were fixed for 12-24 h in formalin, embedded in paraffin and sectioned. For immunohistochemical detection of LAMP2 in brain, paraffin sections were subjected to heat-induced epitope retrieval in citrate buffer, pH 6, and then incubated overnight at 4° C. with rat anti-LAMP2 antibody (Ab13524; Abcam, Cambridge, UK) diluted at 1:500 and subsequently incubated with biotinylated rabbit anti-rat antibody (Dako, Glostrup, DK) at 1:300. For GFAP immunostaining in brain samples, paraffin sections were incubated overnight at 4° C. with rabbit anti-GFAP antibody (Ab6673; Abcam, Cambridge, UK) diluted at 1:1000 and subsequently incubated with biotinylated goat anti-rabbit antibody (31820; Vector Laboratories, Burlingame, Calif., USA) at 1:300. LAMP2, and GFAP signals were amplified by incubating sections with ABC-Peroxidase staining kit (Thermo Scientific, Waltham, Mass., US) at 1:100 dilution and visualized using 3,3-diaminobenzidine (Sigma-Aldrich, St. Louis, Mo., US) as a chromogen.

To stain microglial cells in brain samples, paraffin sections were incubated overnight at 4° C. with BSI-B4 lectin (L5391; Sigma-Aldrich, St. Louis, Mo., USA) diluted at 1:100. BSI-B4 signal was visualized using 3,3-diaminobenzidine (Sigma-Aldrich, St. Louis, Mo., US) as a chromogen. Brightfield images were obtained with an optical microscope (Eclipse 90i; Nikon, Tokyo, JP).

The NIS Elements Advanced Research 2.20 software was used to quantify LAMP2, GFAP, and BSI-B4 signals in 3-5 images of each brain region (original magnification, ×20) per animal, using the same signal threshold settings for all animals. Then, the percentage of positive area was calculated, i.e., the area, in pixels, with a positive signal over the total tissue area in the image.

9. Transmission Electron Microscopy Analysis

Mice were sacrificed by an overdose of isofluorane (Isofluo, Labs. Esteve, Barcelona, ES) and perfused via inferior vena cava with 1 ml of 2.5% glutaraldehyde and 2% paraformaldehyde. A small portion (approximately 1 $mm^3$) of the cerebral cortex, the left lateral lobe of the liver or the lung were sectioned and incubated for 2 hours at 4° C. in the same fixative. After washing in cold cacodylate buffer, the specimens were postfixed in 1% osmium tetroxide, stained in aqueous uranyl acetate, and then dehydrated through a graded ethanol series and embedded in epoxy resin. Ultrathin sections (600-800 Å) from the resin blocks were stained using lead citrate and examined in a transmission electron microscope (H-7000; Hitachi, Tokyo, JP).

10. Open Field Test

The behavior of 6 and 22-month-old mice was analyzed by the open field test performed between 9:00 am and 1:00 pm. Animals were placed in the lower left corner of a brightly lit chamber (41×41×30 cm) crossed by 2 bundles of photobeams (SedaCom32; Panlab) that detected horizontal and vertical movements of the mice. The area surface was divided into three squared concentric regions: center (14×14 cm), periphery (27×27 cm) and border (41×41 cm). Exploratory and motor activities were recorded during the first 3 minutes of the test using a video-tracking system (SmartJunior, Panlab).

11. Statistical Analysis

All results are expressed as mean±SEM. Statistical comparisons were made using one-way ANOVA. Multiple comparisons between control and treatment groups were made using Dunnett's post test, and between all groups using Tukey's post test. Statistical significance was considered if $P<0.05$.

EXAMPLES

Example 1: Construction of pAAV-CAG-hGNS

The CDS for human glucosamine (N-acetyl)-6-sulfatase (NCBI Reference Sequence: NM_002076.3) was used as starting material and was chemically synthetized for this purpose (GeneArt; Life Technologies). The CDS was received cloned inside the plasmid pMA-RQ (AmpR) flanked by MluI and EcoRI restriction sites at 5' and 3', respectively.

The MluI/EcoRI human glucosamine (N-acetyl)-6-sulfatase CDS fragment was excised from the pMA-RQ plasmid and subsequently cloned between the MluI and EcoRI restrictions sites of the AAV backbone plasmid pAAV-CAG. The resulting plasmid was named pAAV-CAG-hGNS (accession number DSM 32342). See FIG. 1A and SEQ ID NO: 5.

The AAV backbone plasmid pAAV-CAG used herein had been previously generated and contained the ITRs from the AAV2 genome, the CAG promoter, and the polyA signal from rabbit β-globin, as well as a multicloning site for cloning of CDSs of interest. The CAG promoter is a hybrid promoter composed of the CMV early/intermediate enhancer and the chicken β-actin promoter. This promoter is able to drive a potent expression ubiquitously.

Example 2: Construction of pAAV-CAG-ohGNS-Version1

Expression cassettes including an optimized version of glucosamine (N-acetyl)-6-sulfatase cDNA sequence (ohGNS) were designed and obtained. The sequence optimization was performed to maximize the efficiency of N-acetylglucosamine 6-sulfatase protein production in human beings through elimination of cryptic splice sites and RNA destabilizing sequence elements for increased RNA stability, addition of RNA stabilizing sequence elements, codon optimization and G/C content adaptation, avoidance of stable RNA secondary structures amongst others changes. The CDS for human glucosamine (N-acetyl)-6-sulfatase (NCBI Reference Sequence: NM_002076.3) was used as starting point for sequence optimization.

The first optimized CDS (GeneArt; Life Technologies) was received cloned inside the plasmid pMA-T (AmpR) flanked by MluI and EcoRI restriction sites at 5' and 3', respectively.

Figure 2:
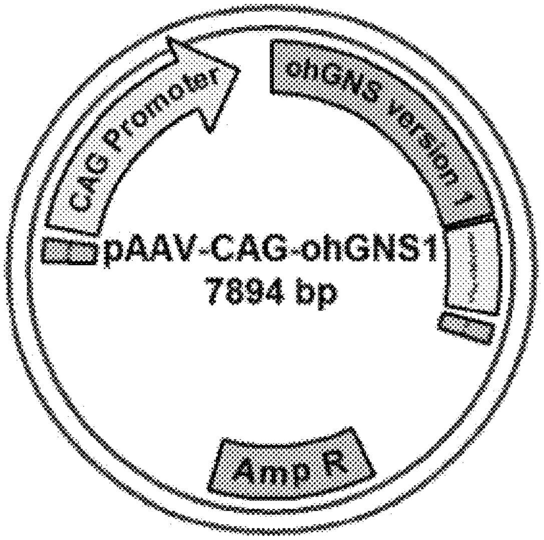
FIG. 2. Generation of pAAV-CAG-ohGNS-version1 and AAV9-CAG-ohGNS-version1. (A) Schematic representation of the plasmid pAAV-CAG-ohGNS-version1 and its components. (B) Schematic representation of the genome of an Adeno-associated vector containing the ohGNS-version1 coding sequence.
Figure 2:
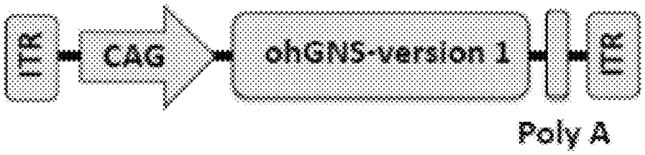

The MluI/EcoRI optimized human glucosamine (N-acetyl)-6-sulfatase CDS fragment was excised from the pMA-T plasmid and subsequently cloned between the MluI and EcoRI restrictions sites of the AAV backbone plasmid pAAV-CAG. The resulting plasmid was named pAAV-CAG-ohGNS-version1 (accession number DSM 32343). See FIG. 2A and SEQ ID NO: 6.

Example 3: Construction of pAAV-CAG-ohGNS-Version2

The CDS for human glucosamine (N-acetyl)-6-sulfatase (NCBI Reference Sequence: NM_002076.3) was subjected to sequence optimization (DNA2.0 Inc). The optimized CDS was received cloned inside the plasmid pJ204 (AmpR) flanked by MluI and EcoRI restriction sites at 5' and 3', respectively.

Figure 3:
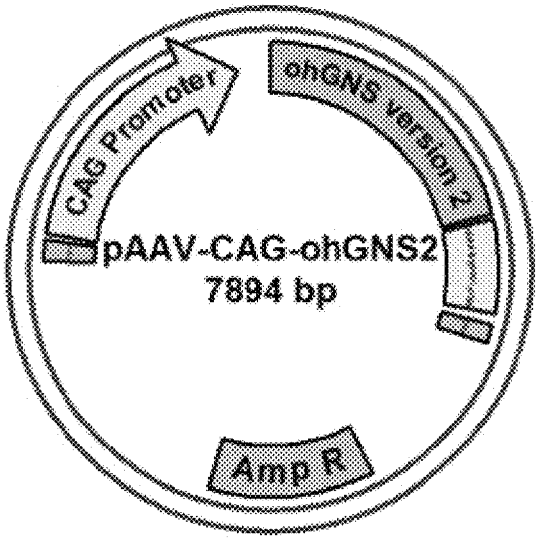
FIG. 3. Generation of pAAV-CAG-ohGNS-version2 and AAV9-CAG-ohGNS-version2. (A) Schematic representation of the plasmid pAAV-CAG-ohGNS-version2 and its components. (B) Schematic representation of the genome of an Adeno-associated vector containing the ohGNS-version2 coding sequence.
Figure 3:
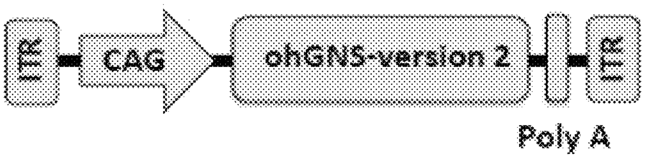

The MluI/EcoRI optimized human glucosamine (N-acetyl)-6-sulfatase CDS fragment was excised from the pJ204 plasmid and subsequently cloned between the MluI and EcoRI restrictions sites of the AAV backbone plasmid pAAV-CAG. The resulting plasmid was named pAAV-CAG-ohGNS-version2 (accession number DSM 32344). See FIG. 3A and SEQ ID NO: 7.

Example 4: Construction of pAAV-CAG-ohGNS-Version3

The CDS for human glucosamine (N-acetyl)-6-sulfatase (NCBI Reference Sequence: NM_002076.3) was subjected to sequence optimization (Genescript Inc). The optimized CDS was received cloned inside the plasmid pUC57 (AmpR) flanked by MluI and EcoRI restriction sites at 5' and 3', respectively.

Figure 4:
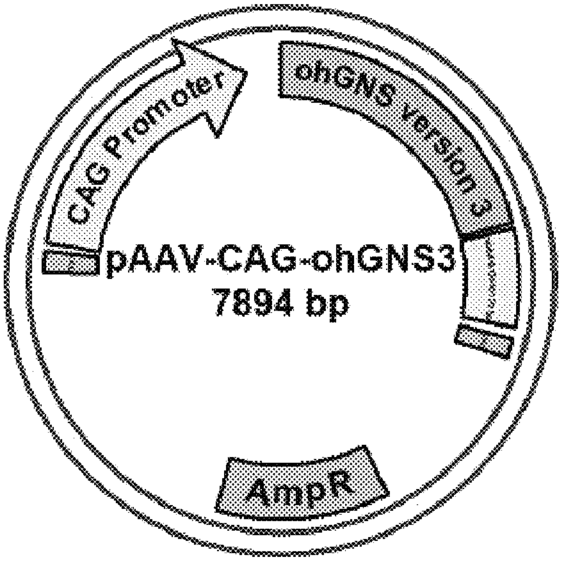
FIG. 4. Generation of pAAV-CAG-ohGNS-version3 and AAV9-CAG-ohGNS-version3. (A) Schematic representation of the plasmid pAAV-CAG-ohGNS-version3 and its components. (B) Schematic representation of the genome of an Adeno-associated vector containing the ohGNS-version3 coding sequence.
Figure 4:
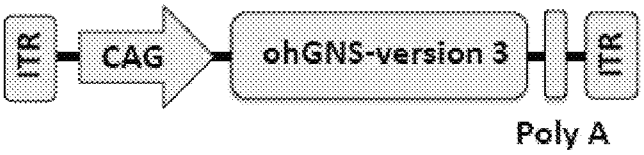

The MluI/EcoRI optimized human glucosamine (N-acetyl)-6-sulfatase CDS fragment was excised from the pUC57 plasmid and subsequently cloned between the MluI and EcoRI restrictions sites of the AAV backbone plasmid pAAV-CAG. The resulting plasmid was named pAAV-CAG-ohGNS-version3 (accession number DSM 32345). See FIG. 4A and SEQ ID NO: 8.

Example 5: Construction of pAAV-CAG-omGNS

The CDS for murine glucosamine (N-acetyl)-6-sulfatase (NCBI Reference Sequence: NM_029364.3) was subjected to sequence optimization (GeneArt; Life Technologies). The optimized CDS; SEQ ID NO: 16, was received cloned inside the plasmid pMA-RQ (AmpR) flanked by MluI and EcoRI restriction sites at 5' and 3', respectively.

Figure 5:
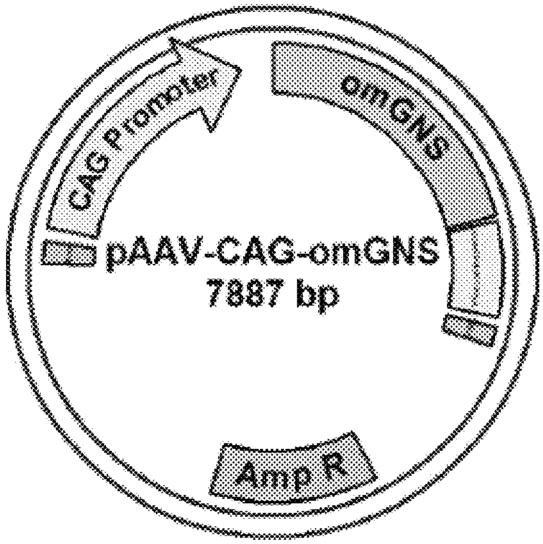
FIG. 5. Generation of pAAV-CAG-omGNS and AAV9-CAG-omGNS. (A) Schematic representation of the plasmid pAAV-CAG-omGNS and its components. (B) Schematic representation of the genome of an Adeno-associated vector containing the omGNS coding sequence.
Figure 5:

The MluI/EcoRI optimized murine glucosamine (N-acetyl)-6-sulfatase CDS fragment was excised from the pMA-RQ plasmid and subsequently cloned between the MluI and EcoRI restrictions sites of the AAV backbone plasmid pAAV-CAG. The resulting plasmid was named pAAV-CAG-omGNS. See FIG. 5A and SEQ ID NO:17.

Example 6: Production of AAV9-CAG-hGNS

Vectors AAV9-CAG-hGNS (SEQ ID NO:9) were generated by helper virus-free transfection of HEK293 cells using three plasmids with modifications. See Matsushita et al., Gene Ther. 1998; 5(7):938-45, Wright et al., Mol Ther. 2005; 12(1)171-8. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-hGNS; SEQ ID NO: 5); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., Gene Ther. 2010; 17(4):503-10. Vectors were dialyzed against PBS+0.001% Pluronic® F68, filtered, titred by qPCR and stored at −80° C. until use. See FIG. 1B.

Example 7: Production of AAV9-CAG-ohGNS-Version1

Vectors AAV9-CAG-ohGNS-version1 (SEQ ID NO:10) were generated by helper virus-free transfection of HEK293 cells using three plasmids with modifications. See Matsushita et al., and Wright et al., supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-ohGNS-version1; SEQ ID NO: 6); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., supra. Vectors were dialyzed against PBS+0.001% Pluronic® F68, filtered, titred by qPCR and stored at −80° C. until use. See FIG. 2B.

Example 8: Production of AAV9-CAG-ohGNS-Version2

Vectors AAV9-CAG-ohGNS-version2 (SEQ ID NO:11) were generated by helper virus-free transfection of HEK293 cells using three plasmids with modifications. See Matsushita et al., and Wright et al., supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-ohGNS-version2; SEQ ID NO: 7); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., supra. Vectors were dialyzed against PBS+0.001% Pluronic® F68, filtered, titred by qPCR and stored at −80° C. until use. See FIG. 3B.

Example 9: Production of AAV9-CAG-ohGNS-Version3

Vectors AAV9-CAG-ohGNS-version3 (SEQ ID NO:12) were generated by helper virus-free transfection of HEK293 cells using three plasmids with modifications. See Matsushita et al., and Wright et al., supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-ohGNS-version3; SEQ ID NO: 8); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., supra. Vectors were dialyzed against PBS+0.001% Pluronic® F68, filtered, titred by qPCR and stored at −80° C. until use. See FIG. 4B.

Example 10: Production of AAV9-CAG-omGNS

Vectors AAV9-CAG-omGNS (SEQ ID NO: 18) were generated by helper virus-free transfection of HEK293 cells using three plasmids with modifications. See Matsushita et al., and Wright et al., supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-omGNS; SEQ ID NO: 17); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., supra. Vectors were dialyzed against PBS+0.001% Pluronic® F68, filtered, titred by qPCR and stored at −80° C. until use. See FIG. 5B and SEQ ID NO:18.

Example 11: In Vitro Testing of pAAV-CAG-hGNS, pAAV-CAG-ohGNS-Version1, pAAV-CAG-ohGNS-Version2 and pAAV-CAG-ohGNS-Version3

HEK293 cells were transfected with 4 μg of plasmids pAAV-CAG-hGNS, pAAV-CAG-ohGNS-version1, pAAV-CAG-ohGNS-version2 and pAAV-CAG-ohGNS-version3 containing different versions of human glucosamine (N-acetyl)-6-sulfatase.

Figure 6:
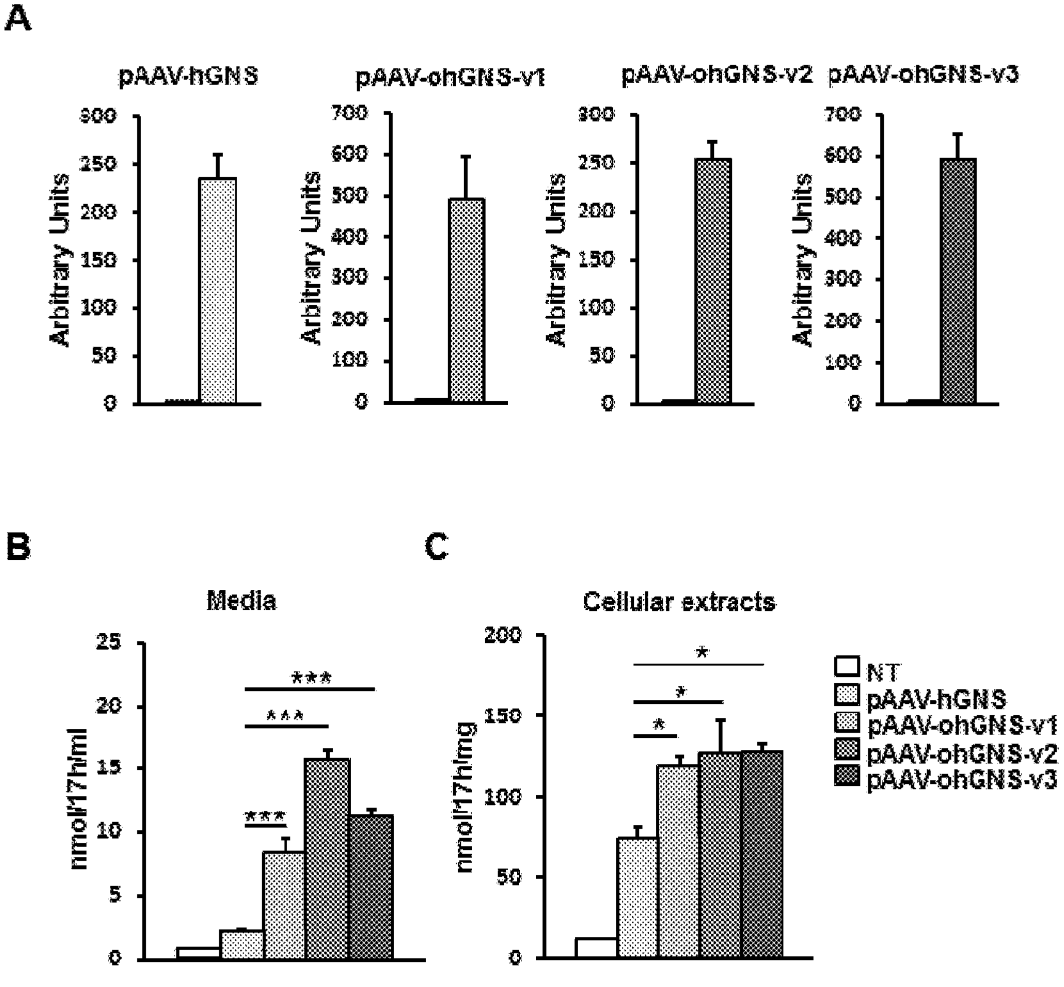
FIG. 6. In vitro testing of pAAV-CAG-hGNS, pAAV-CAG-ohGNS-version1, pAAV-CAG-ohGNS-version2 and pAAV-CAG-ohGNS-version3. Transient transfection of HEK293 cells with 4 μg of pAAV-CAG-hGNS, pAAV-CAG-ohGNS-v1, pAAV-CAG-ohGNS-v2 or pAAV-CAG-ohGNS-v3. (A) Quantitative RT-PCR quantification of the expression of GNS from the different constructs. (B) and (C) Comparison of the levels of GNS activity in the media or cell extracts mediated by the different expression cassettes. Values are means±SEM of 3 wells per condition. *$P<0.05$, ***$P<0.001$ vs. cells transfected with pAAV-CAG-hGNS. "NT" non-transfected.

Forty-eight hours after transfection, cells were collected, total RNA extracted and expression of glucosamine (N-acetyl)-6-sulfatase was measured by quantitative RT-PCR using primers specific for each sequence. Transfection with all four glucosamine (N-acetyl)-6-sulfatase-containing plasmids resulted in detection of glucosamine (N-acetyl)-6-sulfatase mRNA. See FIG. 6A. Furthermore, glucosamine (N-acetyl)-6-sulfatase activity was increased in both the media and the cellular extracts of wells transfected with the therapeutic constructs. See FIGS. 6B and 6C. In both cases, the plasmids encoding for codon-optimized versions of the protein (pAAV-ohGNS versions 1 to 3) led to statistically significant higher levels of production of glucosamine (N-acetyl)-6-sulfatase than the plasmid containing the wild-type sequence. See FIGS. 6B and 6C.

Example 12: Intravenous Injection of AAV-CAG-hGNS, AAV-CAG-ohGNS-Version1, AAV-CAG-ohGNS-Version2 or AAV-CAG-ohGNS-Version3 to MPSIIID Mice A total dose of $1\times10^{10}$ vector genomes of AAV-CAG-hGNS, AAV-CAG-ohGNS-version1, AAV-CAG-ohGNS-version2 or AAV-CAG-ohGNS-version3 containing different versions of the human glucosamine (N-acetyl)-6-sulfatase expressing cassette were delivered intravenously to 2-month-old MPSIIID-affected mice via tail vein injection.

Figure 7:
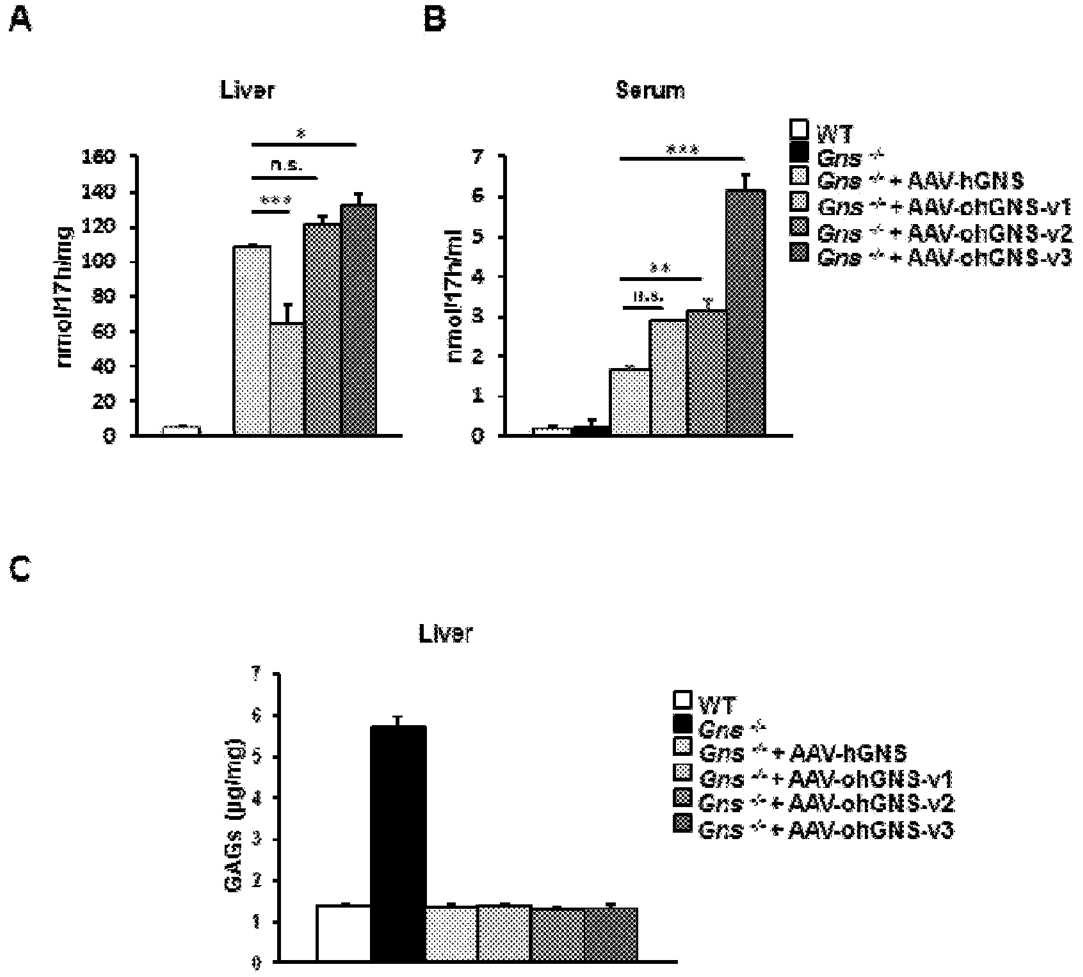
FIG. 7. Intravenous injection of AAV-CAG-hGNS, AAV-CAG-ohGNS-version1, AAV-CAG-ohGNS-version2 or AAV-CAG-ohGNS-version3 to MPSIIID mice. (A) and (B) GNS activity in the liver and serum of wild-type (healthy) mice (WT), untreated $Gns^{-/-}$ mice and $Gns^{-/-}$ mice that received via tail vein injection $1\times10^{10}$ vectors genomes of AAV9-CAG-hGNS, AAV-CAG-ohGNS-version1, AAV-CAG-ohGNS-version2 or AAV-CAG-ohGNS-version3 vectors. (C) Quantification of glycosaminoglycans (GAGs) in the liver of the same cohorts as in (A). Values are means±SEM of 2-5 animals per group. For serum, the n=1 for AAV-CAG-ohGNS-version1. *$P<0.05$, $P<0.01$, *$P<0.001$ vs. $Gns^{-/-}$ mice treated with AAV-CAG-hGNS.

The analysis was performed 2 weeks after vector delivery. Transduction with all four glucosamine (N-acetyl)-6-sulfatase-containing vectors resulted in a substantial increase in glucosamine (N-acetyl)-6-sulfatase activity over the levels measured in MPSIIID animals. Glucosamine (N-acetyl)-6-sulfatase activity levels ranged from 1300% to 2700% of WT levels in liver and 900% to 3300% of WT in serum. See FIGS. 7A and 7B. In the liver, the levels of activity reached with the expression cassette containing version3 of optimized human glucosamine (N-acetyl)-6-sulfatase were statistically higher than those mediated by the vector containing the wild-type sequence. See FIG. 7A. In serum, both version2 and version3 of optimized human glucosamine (N-acetyl)-6-sulfatase led to statistically significant increases in enzymatic activity. See FIG. 7B.

Consistent with the high levels of glucosamine (N-acetyl)-6-sulfatase activity documented in liver and serum, GAG content was completely normalized in the livers of animals injected with all vector constructs. See FIG. 7C.

Example 13: Intracisternal Delivery of AAV9-CAG-omGNS-Short-Term Study

Figure 8:
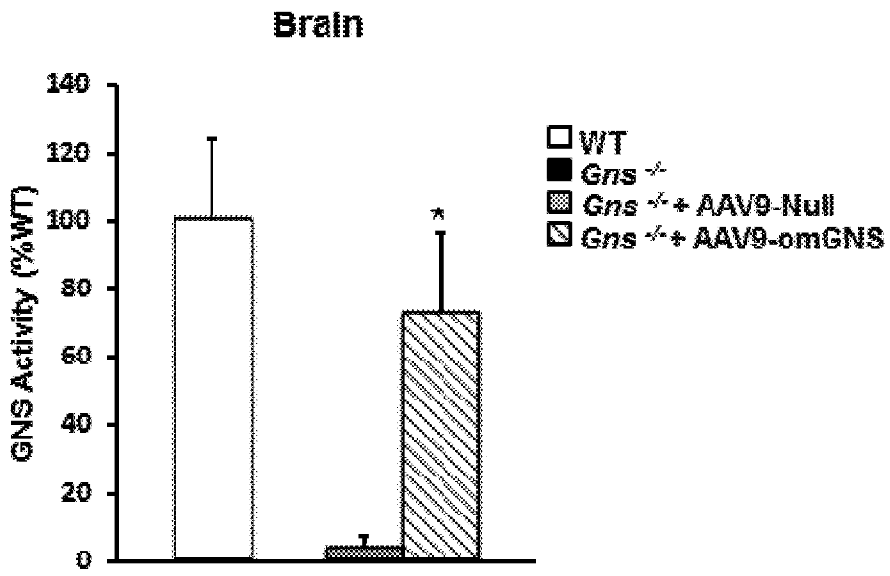
FIG. 8. Intra-CSF delivery of AAV9 vectors coding for optimized murine GNS (AAV9-CAG-omGNS). Short-term study. GNS activity in the brain of wild-type (healthy) mice (WT), untreated $Gns^{-/-}$ mice and $Gns^{-/-}$ mice administered in the CSF, via intracisternal (IC) injection, with $5\times10^{10}$ vg of control vector (AAV9-Null) or AAV9-CAG-omGNS. WT GNS activity was set to 100%. Values are means±SEM of 4-5 mice per group. *$P<0.05$ vs. $Gns^{-/-}$ mice treated with AAV9-Null.
Figure 9:
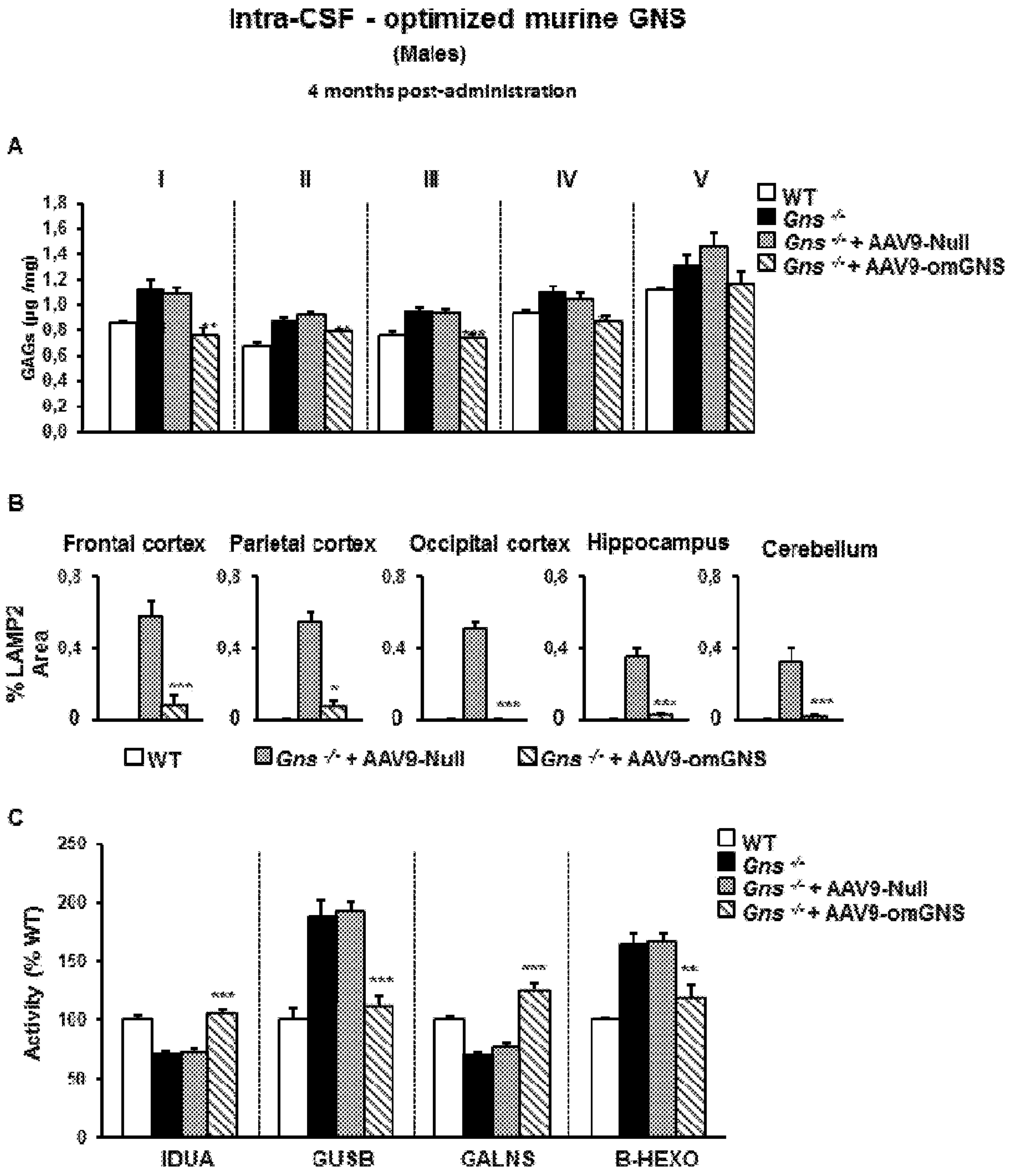
FIG. 9. Intra-CSF delivery of AAV9 vectors coding for optimized murine GNS (AAV9-CAG-omGNS) to male mice. (A) Quantification of glycosaminoglycans (GAGs) in different parts of the brain (sections I-V) in wild-type (healthy) mice (WT) and untreated $Gns^{-/-}$ male mice and $Gns^{-/-}$ male mice administered in the cisterna magna with either $5\times10^{10}$ vg of control vector (AAV9-null) or $5\times10^{10}$ vg of AAV9-CAG-omGNS. (B) Quantification of the signal intensity obtained in different areas of the brain following staining for the lysosomal marker LAMP-2 in the same cohort of animals as in (A). (C) Activity of other lysosomal enzymes in brain extracts obtained from the same cohorts of animals as in (A). IDUA, iduronidase, alpha-L-, GALNS galactosamine (N-acetyl)-6-sulfatase, GUSB, glucuronidase, beta, B-HEXO, hexosaminidase B. Values are means±SEM of 4-5 mice per group. $P<0.01$, *$P<0.001$ vs. $Gns^{-/-}$ male mice treated with AAV9-Null.

A total dose of $5\times10^{10}$ vector genomes of AAV9-CAG-omGNS vector was injected into the cisterna magna of 2-month-old MPSIIID animals in a total volume of 5 μl. Four months after vector administration, the enzymatic activity of GNS in the brain of MPSIIID treated animals was normalized, reaching similar values to those observed in healthy animals. See FIG. 8. The restoration of GNS activity led to a complete normalization of the substrate accumulation characteristic of the disease in all CNS regions analysed, as indicated by the similar level of GAG build-up in wild-type controls and treated $Gns^{-/-}$ mice. See FIG. 9A. Likewise, the quantification of the signal intensity of brain sections stained with an antibody reactive to the lysosomal marker Lysosomal Associated Membrane Protein 2 (LAMP2), used as indicator of the size of the lysosomal compartment, revealed a reduction in LAMP2+ area of approximately 90% in male $Gns^{-/-}$ treated mice over values documented in GNS-deficient mice administered with a control "Null" vector. See FIG. 9B.

The disruption of normal lysosomal homeostasis due to undegraded substrate accumulation can alter the activity of other lysosomal enzymes different from the one directly affected by the mutation. See Ribera et al., Hum Mol Genet. 2014; doi: 10.1093/hmg/ddu727. The activities of IDUA (iduronidase, alpha-L-), GALNS (galactosamine (N-acetyl)-6-sulfatase), GUSB (glucuronidase, beta), and HEXB (hexosaminidase B) were altered in the brains of untreated $Gns^{-/-}$ male mice or $Gns^{-/-}$ male mice treated with control "Null" vector, but treatment with AAV9-CAG-omGNS returned these activities to the levels observed in healthy wild-type mice, evidencing that lysosomal homeostasis was restored by vector-derived expression of Gns. See FIG. 9C.

Figure 10:
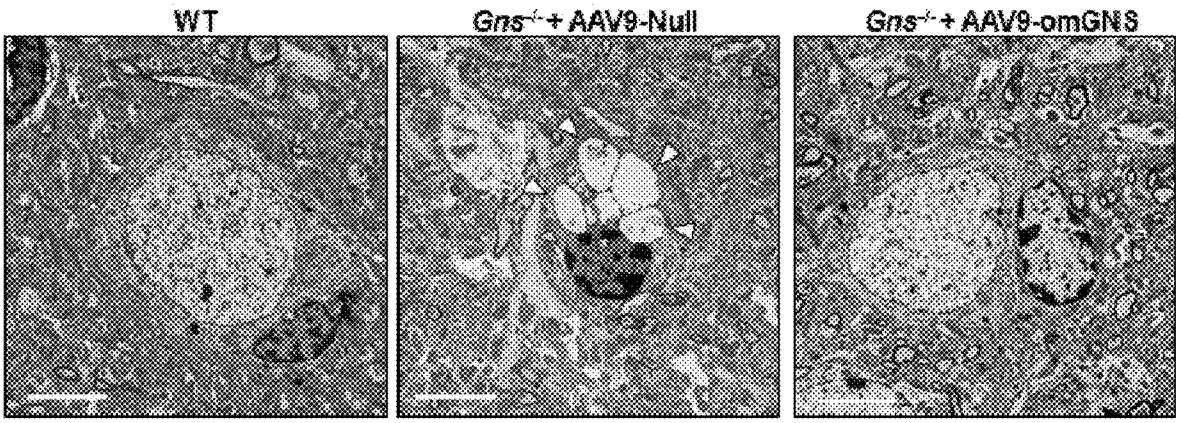
FIG. 10. Intra-CSF delivery of AAV9 vectors coding for optimized murine GNS (AAV9-CAG-omGNS) to males. Short-term study. Ultrastructural analysis of the cerebral cortex of 6-month-old healthy wild-type (WT) male mice and $Gns^{-/-}$ littermates injected at the age of 2 months with $5\times10^{10}$ vg of either AAV9-Null or AAV9-Gns vectors. The delivery of therapeutic vector completely cleared perineuronal glial cells (indicated by asterisks) of enlarged lysosomes (indicated by white arrowheads). Scale bar: 10 μm.

The ultrastructural analysis by transmission electron microscopy of the cerebral cortex of 6-month-old male mice revealed the presence in Null-injected GNS-deficient mice of large vacuoles containing electrolucent substance in the cytoplasm of cells identified as perineuronal glial cells. These vesicles, which appeared to be lysosomes filled with storage material, were completely absent in samples from healthy wild-type or AAV9-Gns-treated $Gns^{-/-}$ animals, confirming the restoration of the normal size of the lysosomal compartment following gene transfer. See FIG. 10.

Figure 11:
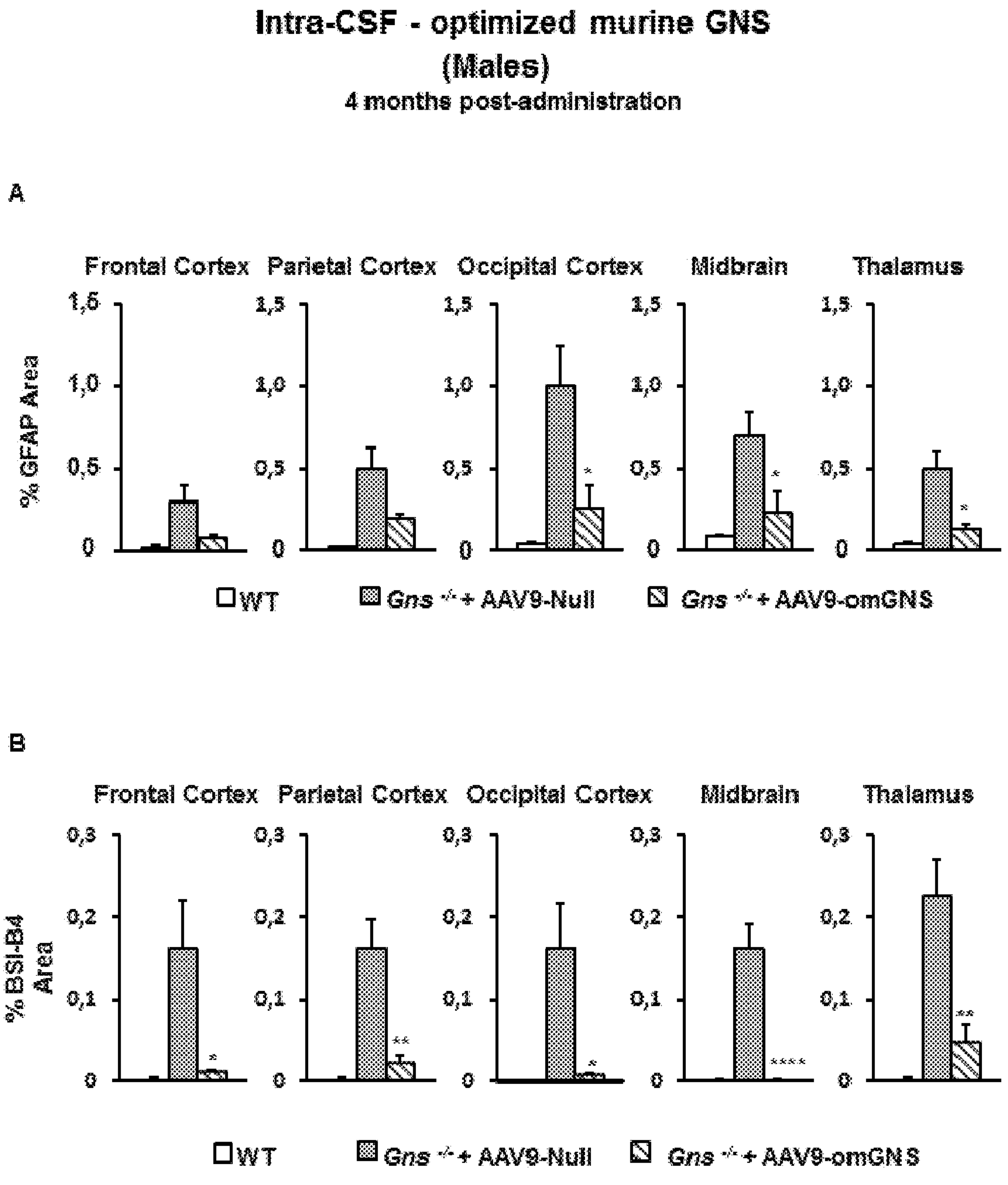
FIG. 11. Intra-CSF delivery of AAV9 vectors coding for optimized murine GNS (AAV9-CAG-omGNS) to males. Short-term study. (A, B) Histograms represent the signal intensity measured following immunostaining for the astrocyte marker GFAP (A) and for the microglial marker BSI-B4 (B) in sections of frontal, parietal, and occipital cortex, superior colliculus, and thalamus from wild-type (healthy), and $Gns^{-/-}$ male mice administered in the cisterna magna with either $5\times10^{10}$ vg of control vector (AAV-null) or $5\times10^{10}$ vg of AAV9-CAG-omGNS. Results are shown as means±SEM of 5 mice per group. $P<0.01$, **$P<0.0001$ vs. $Gns^{-/-}$ male mice treated with AAV9-Null.

Neuroinflamation, characterized the activation of glial cells of the central nervous system, is a hallmark of the Sanfilippo syndrome. The signal intensity for the staining used to detect astrocytosis (GFAP) and microgliosis (BSIB4) was increased in $Gns^{-/-}$ mice treated with Null vectors in comparison to healthy controls. The treatment of $Gns^{-/-}$ mice with AAV9-CAG-omGNS decreased the % of positive area of both markers of inflammation in all brain regions studied. See FIGS. 11A and 11B.

Figure 12:
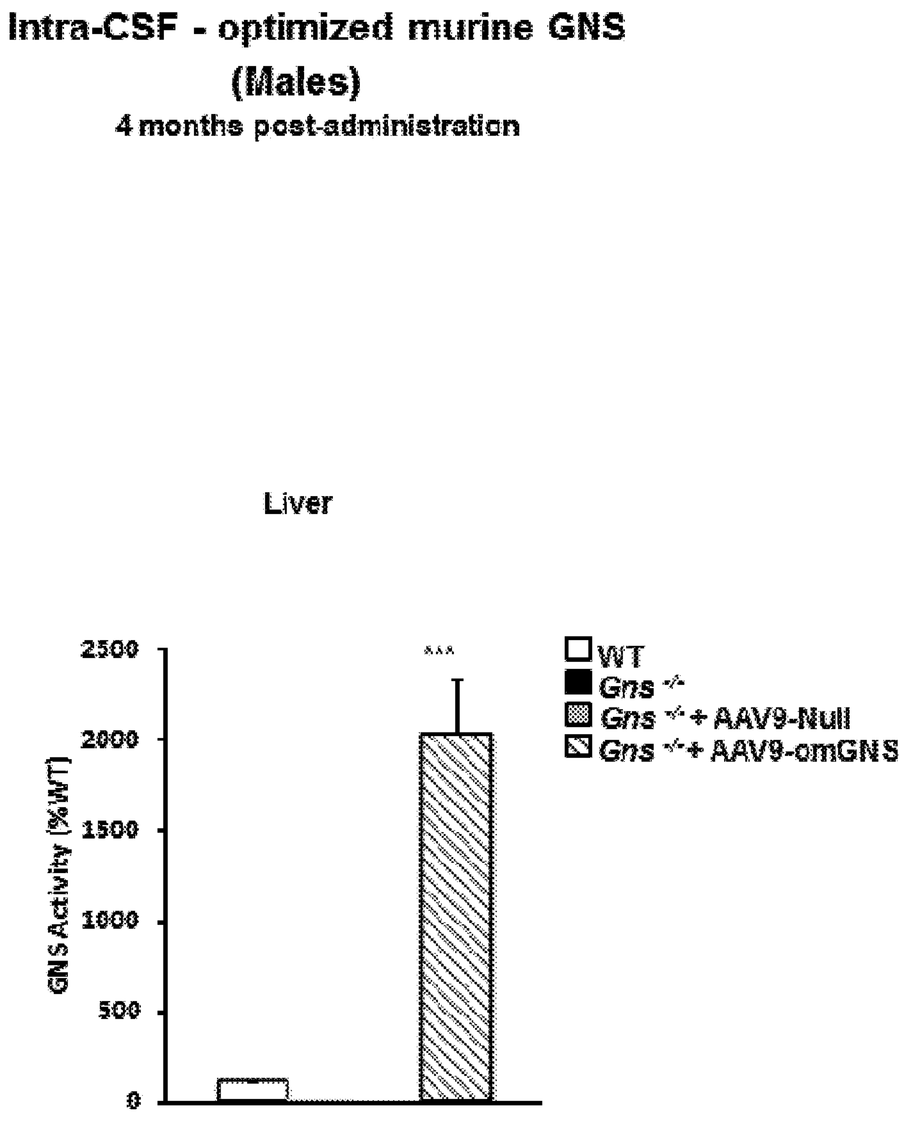
FIG. 12. Intra-CSF delivery of AAV9 vectors coding for optimized murine GNS (AAV9-CAG-omGNS). Short-term study. GNS activity in the liver of wild-type (healthy) mice, untreated $Gns^{-/-}$ male mice and $Gns^{-/-}$ male mice administered in the CSF, via intracisternal (IC) injection, with $5\times10^{10}$ vg of control vector (AAV9-Null) or AAV9-CAG-omGNS. WT GNS activity was set to 100%. Values are means±SEM of 4-5 mice per group. ***P<0.001 vs. $Gns^{-/-}$ male mice treated with AAV9-Null.
Figure 13:
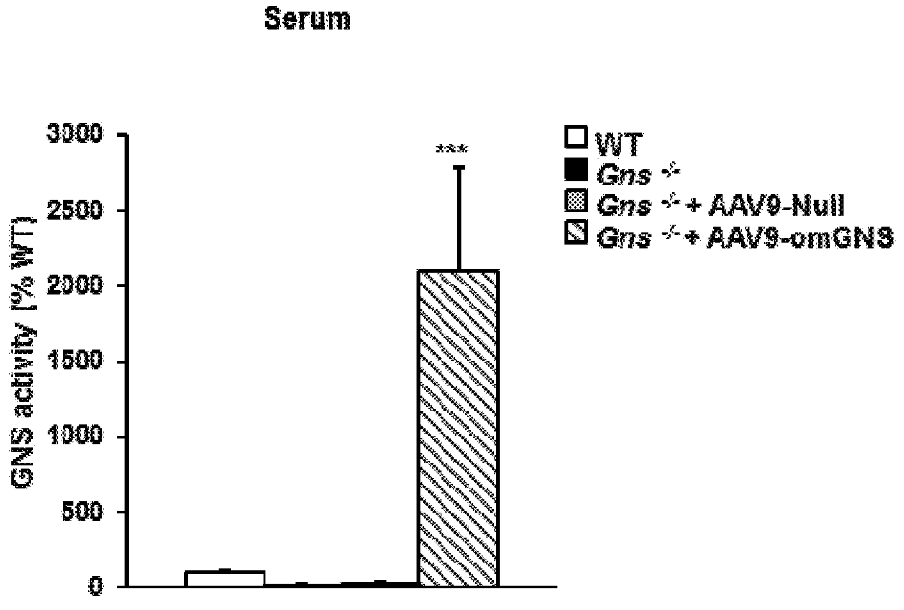
FIG. 13. Intra-CSF delivery of AAV9 vectors coding for optimized murine GNS (AAV9-CAG-omGNS). Short-term study. GNS activity in the circulation-expressed as % of WT activity-in 6-month-old male mice, i.e. 4 months after delivery of $5\times10^{10}$ vg of either AAV9-CAG-omGNS or AAV9-Null to the CSF of GNS-deficient animals. Age-matched untreated $Gns^{-/-}$ mice also served as controls. WT GNS activity was set to 100%. Values are means±SEM of 5 mice per group. ***P<0.001 vs. $Gns^{-/-}$ male mice treated with AAV9-Null.
Figure 14:
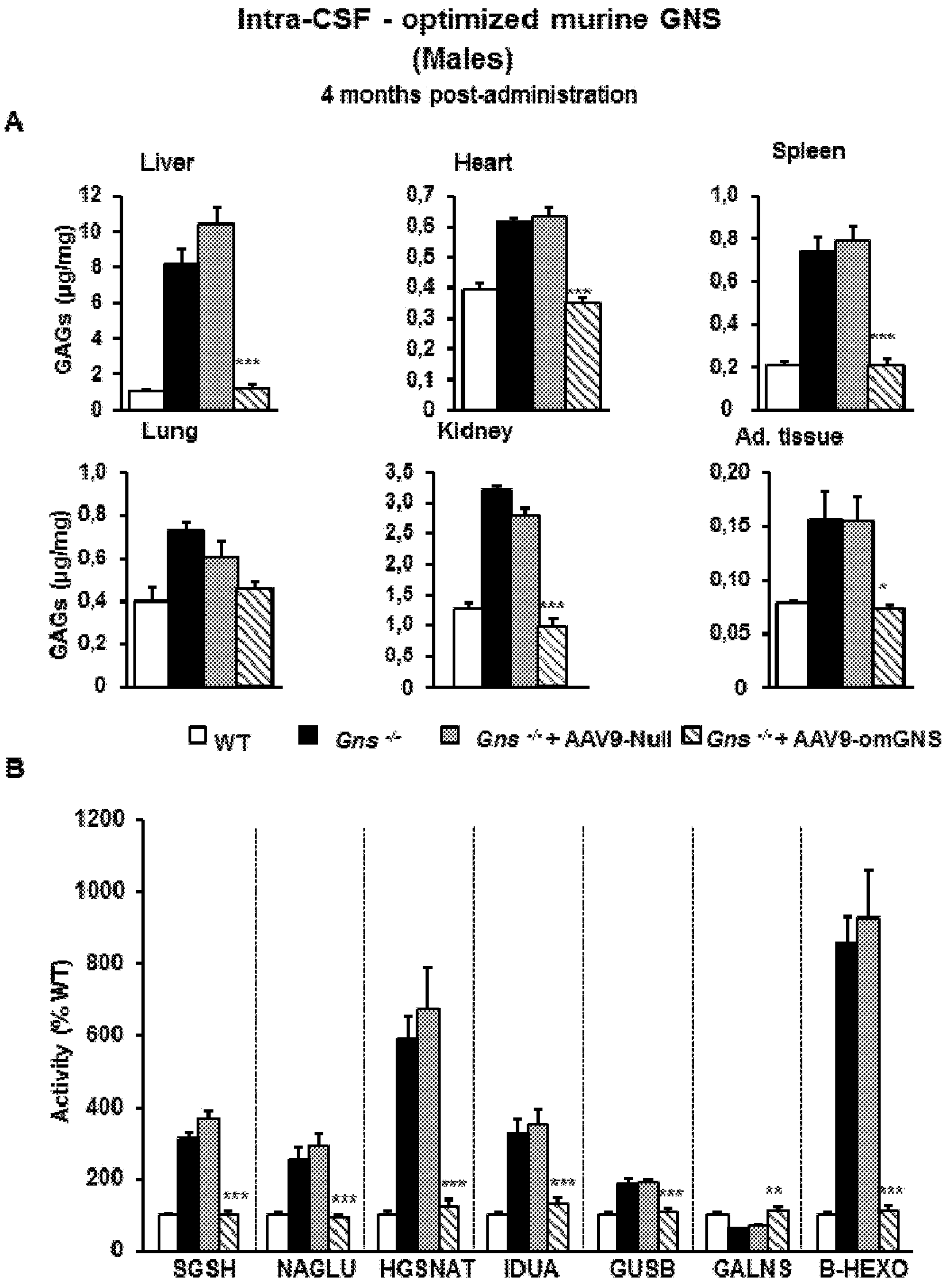
FIG. 14. Intra-CSF delivery of AAV9 vectors coding for optimized murine GNS (AAV9-CAG-omGNS). Short-term study. (A) Quantification of glycosaminoglycans (GAGs) in somatic organs from wild-type (healthy), and untreated $Gns^{-/-}$ male mice or $Gns^{-/-}$ male mice administered in the cisterna magna with either $5\times10^{10}$ vg of control vector (AAV-null) or $5\times10^{10}$ vg of AAV9-CAG-omGNS. (B) Activity of other lysosomal enzymes in liver extracts obtained from the same cohorts of animals as in (A). IDUA, iduronidase, alpha-L-, SGSH, N-sulfoglucosamine sulfohydrolase, NAGLU, N-acetylglucosaminidase, alpha, HGSNAT, heparan-alpha-glucosaminide N-acetyltransferase, GALNS galactosamine (N-acetyl)-6-sulfatase, GUSB, glucuronidase, beta, B-HEXO, hexosaminidase B. WT enzyme activities were set to 100%. Values are means±SEM of 4-5 mice per group. *P<0.05, P<0.01, *P<0.001, ****P<0.0001 vs. $Gns^{-/-}$ male mice treated with AAV9-Null.

AAV9 vectors administered to the CSF leak to the periphery and transduce the liver. See Haurigot et al., Clin Invest. 2013; 123(8):3254-3271. Accordingly, the activity of GNS in the liver of $Gns^{-/-}$ male mice treated with AAV9-CAG-omGNS was approximately 20-fold higher than that observed in healthy animals. See FIG. 12. When overexpressed in the liver, soluble lysosomal proteins are efficiently secreted to the bloodstream, turning this organ into a source of circulating enzyme See Ruzo et al., Mol Ther 2012; 20(2):254-66. In the serum of GNS-deficient mice treated with AAV9-CAG-omGNS vectors, GNS activity was 20-fold higher than in wild-type littermates. See FIG. 13. When the somatic efficacy of the therapy was evaluated through quantification of the GAG content in different organs, a full normalization was observed in most tissues, including liver, heart, spleen, lung, kidney and adipose tissue. See FIG. 14A.

Figure 15:
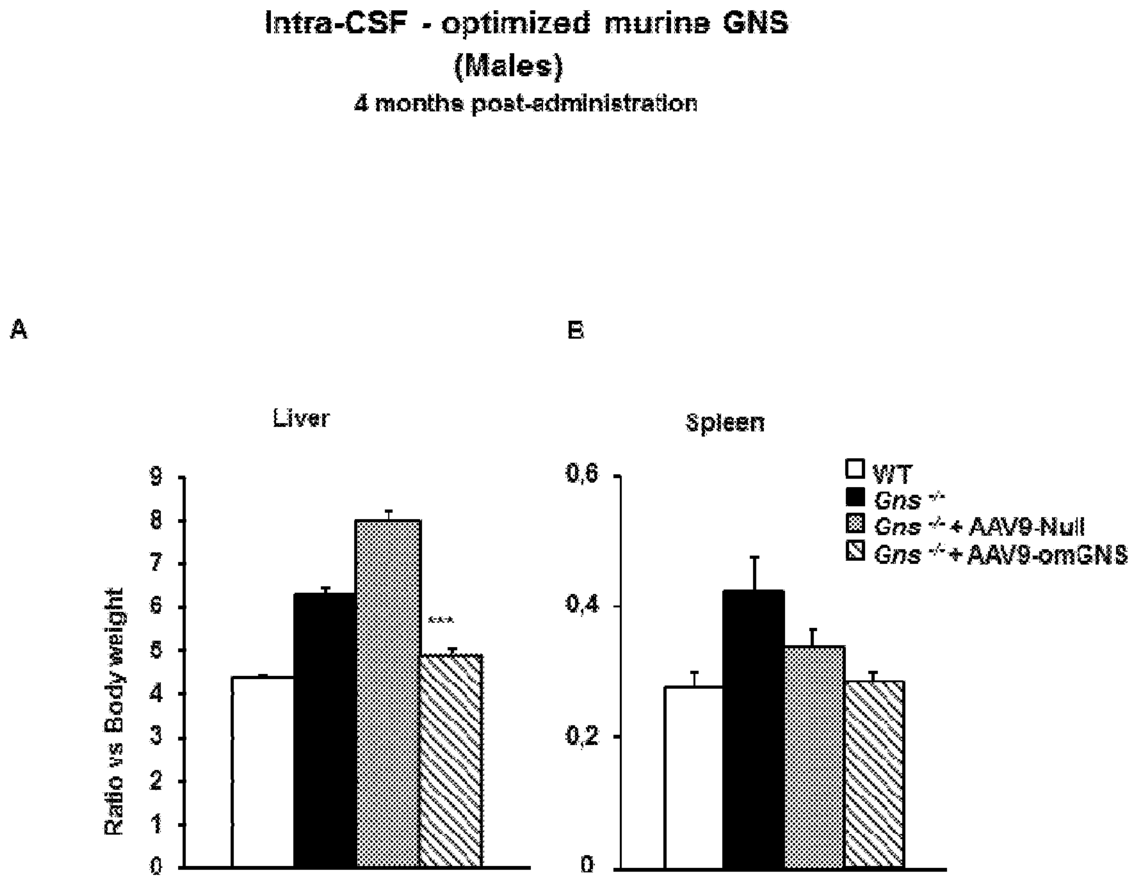
FIG. 15. Intra-CSF delivery of AAV9 vectors coding for optimized murine GNS (AAV9-CAG-omGNS). Short-term study. Wet weight of the liver (A) and spleen (B) relative to whole body weight in wild-type (healthy), untreated $Gns^{-/-}$ male mice and Gns/male mice administered in the CSF with $5\times10^{10}$ vg of control vector (AAV9-Null) or $5\times10^{10}$ vg of AAV9-CAG-omGNS vector at two months of age and analysed 4 months later. Values are means±SEM of n=8-13 animals/group. ***P<0.001 versus $Gns^{-/-}$ male mice treated with AAV9-Null.
Figure 16:
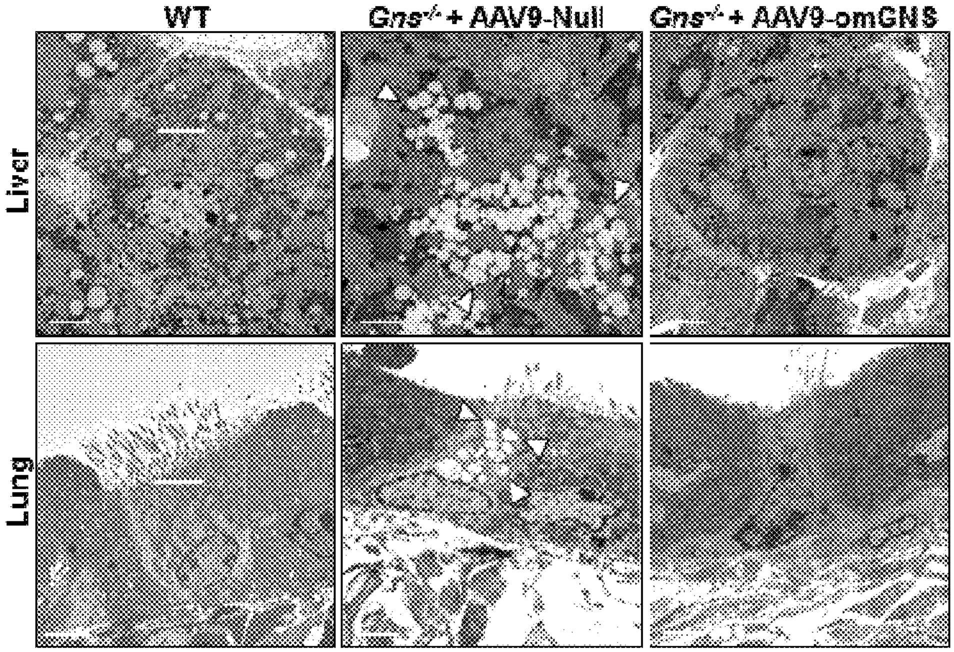
FIG. 16. Intra-CSF delivery of AAV9 vectors coding for optimized murine GNS (AAV9-CAG-omGNS). Short-term study. Analysis by transmission electron microscopy of the ultrastructure of hepatocytes (liver) and ciliated bronchial cells (lung) of organs harvested from 6-month-old healthy WT and $Gns^{-/-}$ males administered in the CSF with $5\times10^{10}$ vg of either null control vector (AAV9-Null) or an equivalent dose of vectors coding for optimized murine GNS (AAV9-CAG-omGNS). Enlarged lysosomes are indicated by arrowheads. Scale bar: liver, 10 µm; lung, 5 µm.

Further demonstration of the potential of intra-CSF AAV9-CAG-omGNS treatment to counteract lysosomal pathology in $Gns^{-/-}$ mice was provided by the measurement of activity of other lysosomal enzymes in liver extracts. SGSH (sulfamidase), NAGLU (N-Acetylglucosaminidase alpha), HGSNAT (heparan-alpha-glucosaminide N-acetyltransferase), IDUA, GUSB, GALNS, HEXB were considerably altered with respect to WT levels in untreated $Gns^{-/-}$ mice or in $Gns^{-/-}$ mice treated with control "Null" vector. Treatment with AAV9-CAG-omGNS completely normalized the activities of all these enzymes. See FIG. 14B. In agreement with the GAG content data, the weight of the liver was normalized in $Gns^{-/-}$ mice treated with AAV9-CAG-omGNS. See FIG. 15A. The weight of the spleen was also normalized in AAV9-CAG-omGNS-treated animals. See FIG. 15B. Finally, transmission electron microscopy analysis revealed that 6-month-old AAV9-Null-injected GNS-deficient mice presented a large number of electrolucent vacuoles within their hepatocytes and bronchial ciliated cells of the lung, whereas healthy WT and AAV9-CAG-omGNS-treated mice did not. See FIG. 16.

Figure 17:
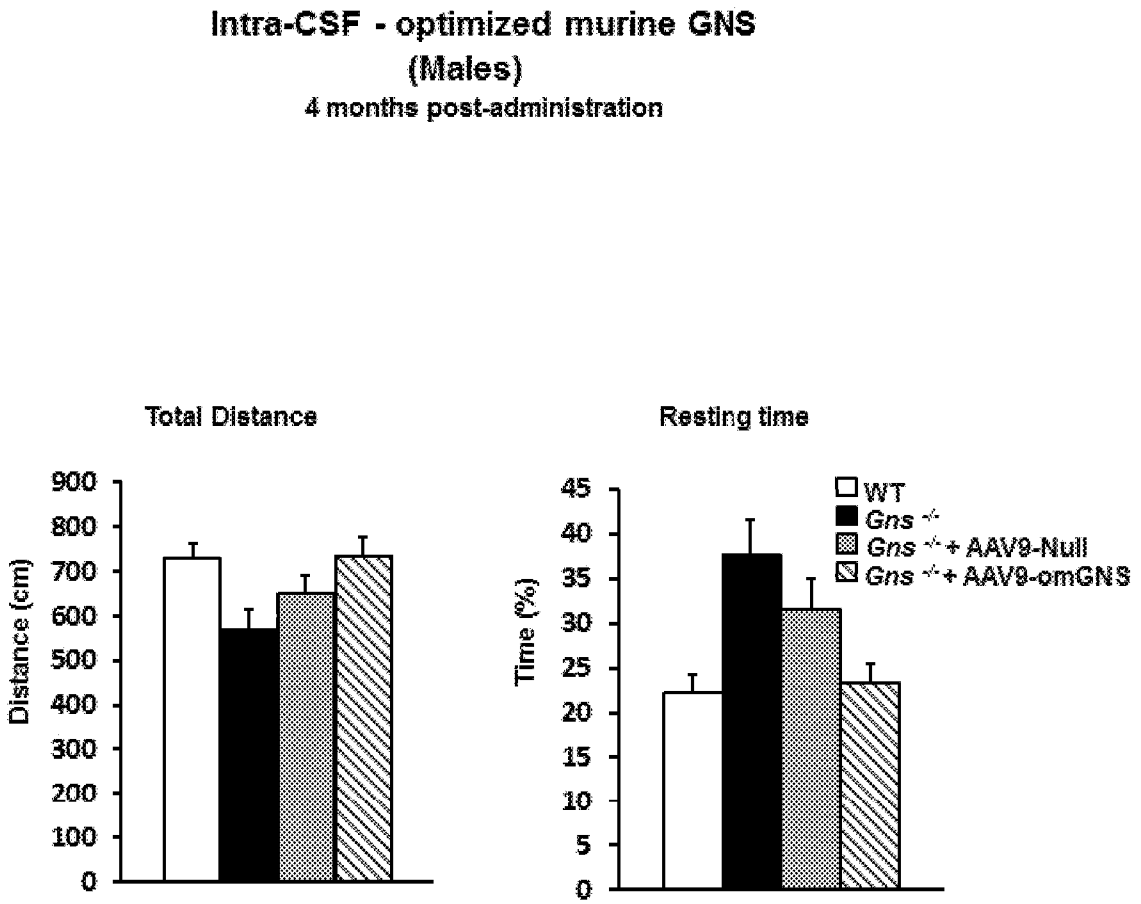
FIG. 17. Intra-CSF delivery of AAV9 vectors coding for optimized murine GNS (AAV9-CAG-omGNS). Short-term study. Evaluation of the locomotor and exploratory activity thorough the Open Field test in naïve wild-type (healthy), untreated $Gns^{-/-}$ male mice and $Gns^{-/-}$ male mice administered in the CSF with $5\times10^{10}$ vg of control vector (AAV9-Null) or $5\times10^{10}$ vg of AAV9-CAG-omGNS vector at two months of age and analysed four months later. Total distance traveled, Resting time. Results are shown as mean±SEM, n=15-18 animals per group.

The impact of the intra-CSF administration of AAV9-CAG-omGNS on behaviour was assessed with the open field test, which evaluates the general locomotor and exploratory activity of mice in unknown surroundings. Untreated and AAV9-null-treated $Gns^{-/-}$ mice displayed reduced locomotor activity compared with healthy mice in terms of the total distance traveled during the test and the amount of time they rested. Intracisternal administration of AAV9-CAG-omGNS completely corrected behavioural deficits in $Gns^{-/-}$ male mice. See FIG. 17.

Example 14: Intracisternal Delivery of AAV9-CAG-omGNS-Long-Term Study

Figure 18:
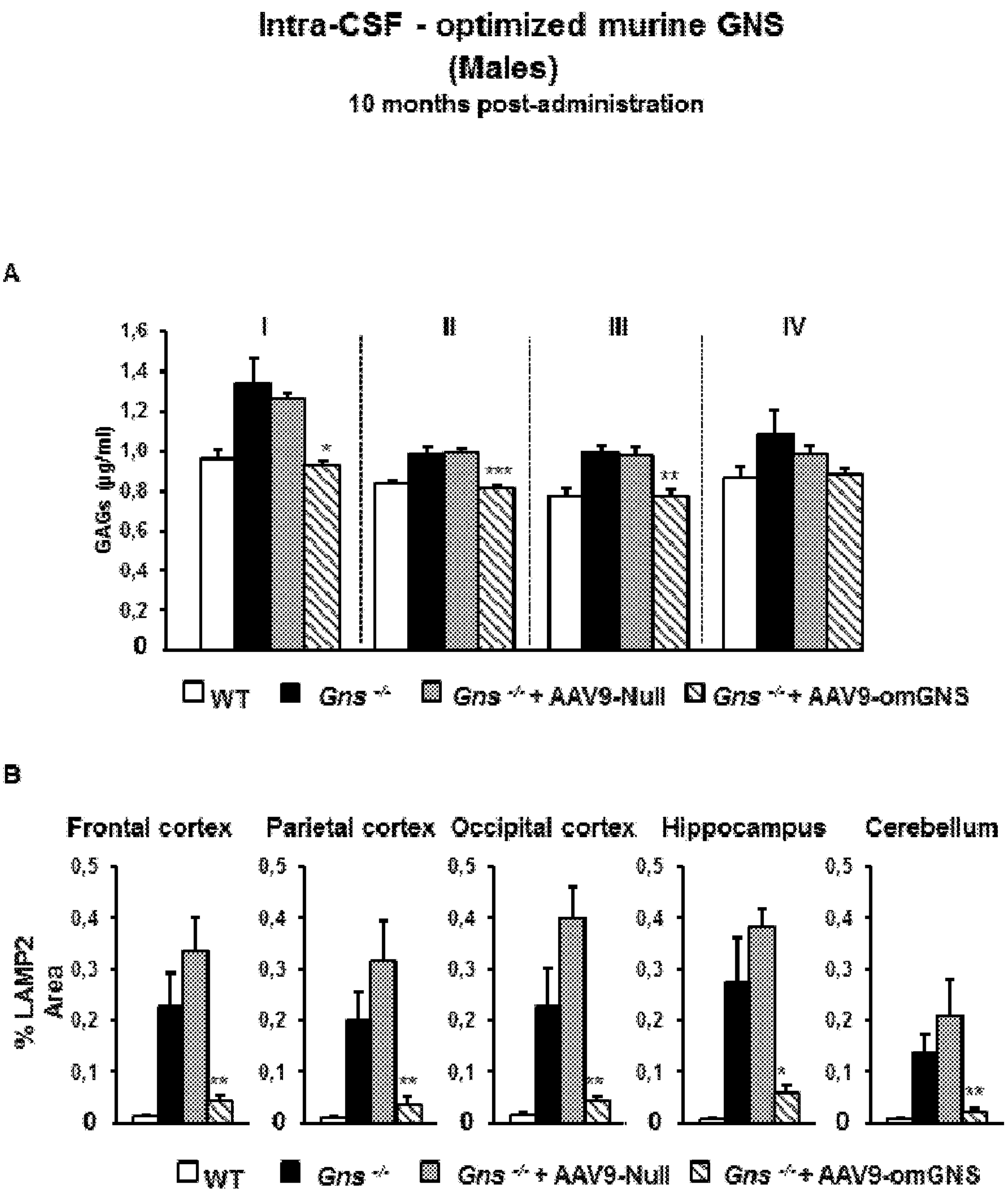
FIG. 18. Intra-CSF delivery of AAV9 vectors coding for optimized murine GNS (AAV9-CAG-omGNS)—Long-term study. (A) Quantification of glycosaminoglycans (GAGs) in different parts of the brain (sections I-IV) in wild-type (healthy) mice (WT) and untreated $Gns^{-/-}$ male mice and $Gns^{-/-}$ male mice administered in the cisterna magna with either $5\times10^{10}$ vg of control vector (AAV9-null) or $5\times10^{10}$ vg of AAV9-CAG-omGNS. Mice were treated at the age of 2 months and analysed 10 months later. Values are means±SEM of 5 mice per group. (B) Histograms represent the signal intensity obtained in different areas of the encephalon following staining of brain sections with an antibody that recognizes the lysosomal marker LAMP-2. Values are means±SEM of 3-5 mice per group. *P<0.05, P<0.01, *P<0.001 vs. $Gns^{-/-}$ male mice treated with AAV9-Null.

To evaluate the therapeutic efficacy of a single administration of AAV9-CAG-omGNS in mediating long-term correction of MPSIIID, a cohort of GNS-deficient animals was injected in the cisterna magna with $5\times10^{10}$ vector genomes of AAV9-CAG-omGNS vector at the age of 2 months and was analysed 10 months after vector administration, i.e when mice were 1-year-old. GNS gene transfer reduced GAG content throughout the encephalon; by 12 months of age AAV9-CAG-omGNS-treated animals showed the same GAG levels than healthy animals, providing proof of long-term therapeutic efficacy. See FIG. 18A.

To further evaluate the ability of the therapy to provide lasting disease correction, immunohistochemical detection of LAMP2 was performed on encephalon sections of 12-month-old animals. Reflecting the pathological storage of lysosomal GAGs, untreated or Null-injected $Gns^{-/-}$ males showed significant increases in the intensity of LAMP2 signal in all regions of the encephalon analysed. See FIG. 18B. In AAV9-CAG-omGNS-treated mice, the reduction in the accumulation of GAGs observed after gene transfer translated into a marked drop in LAMP2 positive signal to almost WT levels the different areas, indicating shrinkage of the lysosomal compartment as GAG levels normalized. See FIG. 18B.

Figure 19:
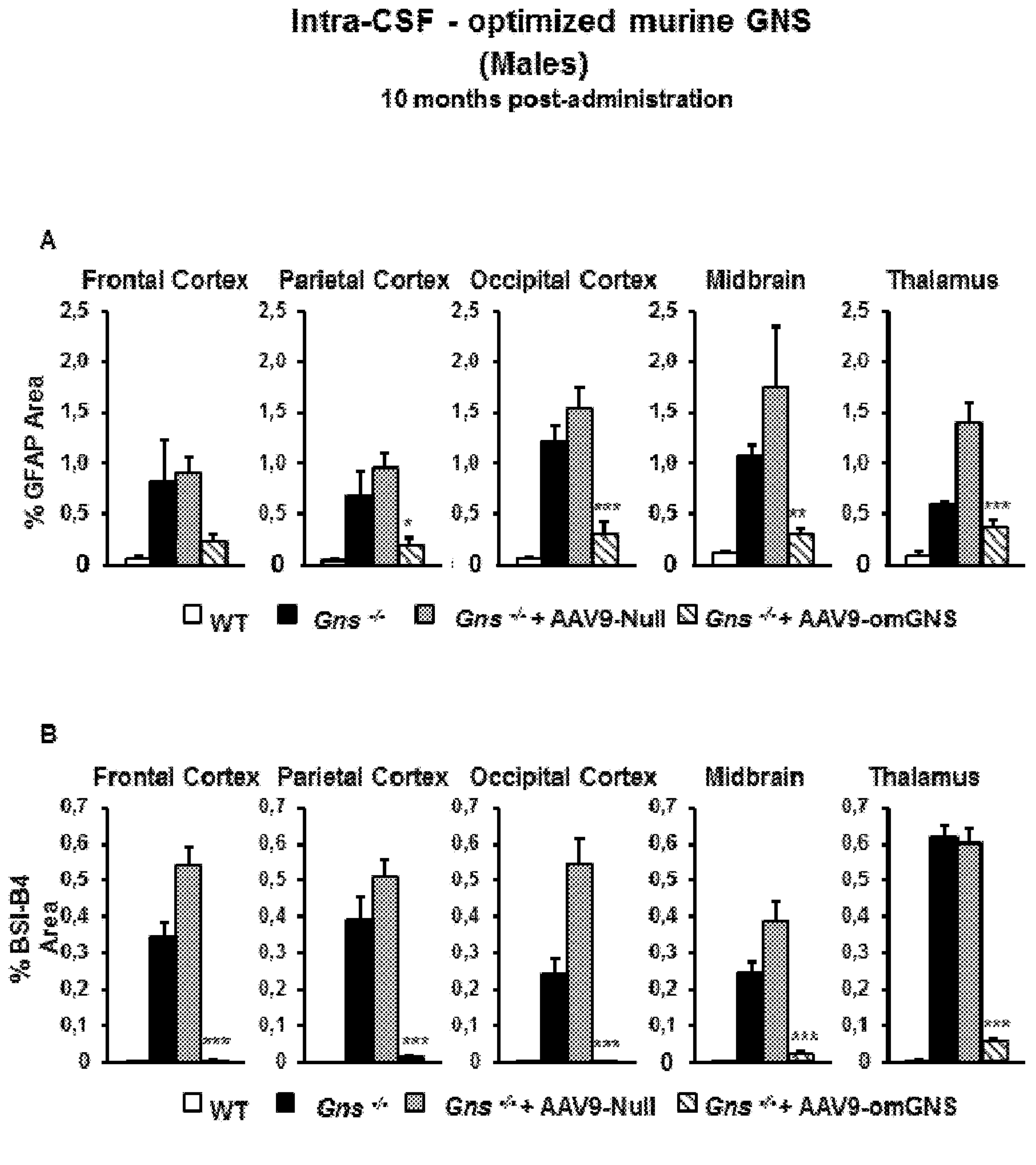
FIG. 19. Intra-CSF delivery of AAV9 vectors coding for optimized murine GNS (AAV9-CAG-omGNS). Long-term study. (A, B) Quantification of the signal intensity measured following immunostaining for the astrocyte marker GFAP (A) and for the microglial marker BSI-B4 (B) in sections of frontal, parietal, and occipital cortex, superior colliculus, and thalamus from wild-type (healthy), and $Gns^{-/-}$ male mice administered in the cisterna magna with either $5\times10^{10}$ vg of control vector (AAV-null) or $5\times10^{10}$ vg of AAV9-CAG-omGNS at the age of 2 months and analysed 10 months later. Results are shown as means±SEM of 3-5 mice per group. *P<0.05, P<0.01, *P<0.001 vs. $Gns^{-/-}$ male mice treated with AAV9-Null.

When astrogliosis and microgliosis were analysed 10 months post a single AAV9-CAG-omGNS vector administration, GNS-deficient male mice that had received AAV9-CAG-omGNS vectors showed a remarkable reduction in GFAP signal intensity in all brain areas studied, as demonstrated by morphometric analysis. See FIG. 19A. Similarly, treatment with GNS-encoding vectors reduced BSI-B4 positive signal to levels almost as low as those quantified in wild-type healthy animals. See FIG. 19B.

Figure 20:
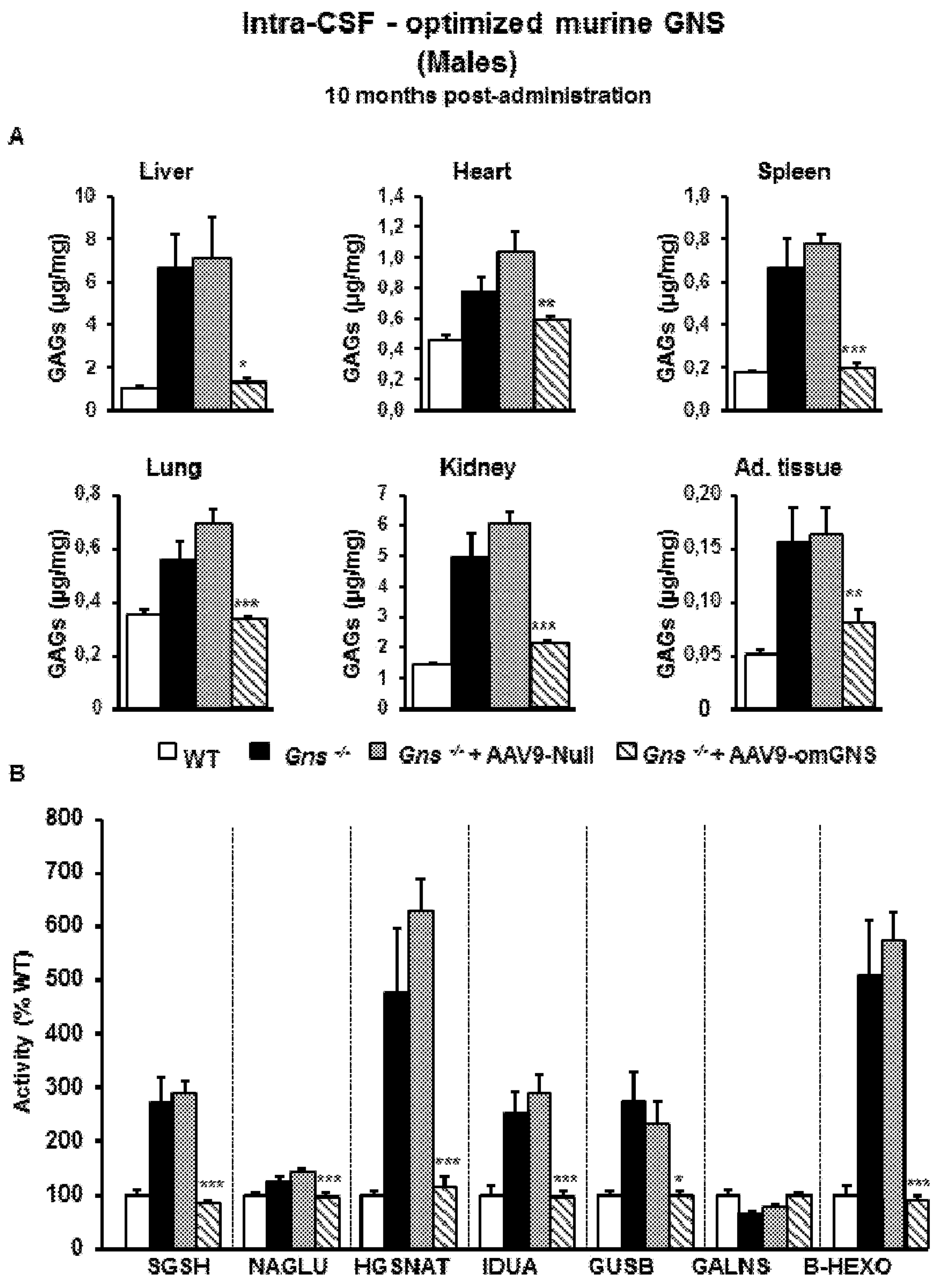
FIG. 20. Intra-CSF delivery of AAV9 vectors coding for optimized murine GNS (AAV9-CAG-omGNS). Long-term study. (A) Quantification of glycosaminoglycans (GAGs) in somatic organs from wild-type (healthy), and untreated $Gns^{-/-}$ male mice or $Gns^{-/-}$ male mice administered in the cisterna magna with either $5\times10^{10}$ vg of control vector (AAV-null) or $5\times10^{10}$ vg of AAV9-CAG-omGNS. Mice were treated at the age of 2 months and analysed 10 months later. (B) Activity of lysosomal enzymes not affected by the mutation in liver extracts obtained from the same cohorts of animals as in (A). IDUA, iduronidase, alpha-L-, SGSH, N-sulfoglucosamine sulfohydrolase, NAGLU, N-acetylglucosaminidase, alpha, HGSNAT, heparan-alpha-glucosaminide N-acetyltransferase, GALNS galactosamine (N-acetyl)-6-sulfatase, GUSB, glucuronidase, beta, B-HEXO, hexosaminidase B. WT enzyme activities were set to 100%. Values are means±SEM of 4-8 mice per group. *P<0.05, P<0.01, *P<0.001 vs. $Gns^{-/-}$ male mice treated with AAV9-Null.

Ten months after AAV9-CAG-omGNS delivery, treated GNS-deficient mice showed normal or almost normal content of GAGs in peripheral organs such as liver, heart, spleen, lung, kidney and adipose tissue. See FIG. 20A.

Consistent with this complete clearance of pathological HS accumulation, the liver of GNS-deficient animals treated with AAV9-CAG-omGNS vector showed normal levels of activity of other lysosomal enzymes not affected by mutation and involved in the catabolism of HS, such as IDUA, SGSH, NAGLU and HGSNAT, or unrelated to the HS pathway, such as GALNS, GUSB, and β-HEXO. See FIG. 20B. The activity of these enzymes is already perturbed at the age of treatment, i.e. in young 2-month-old animals, demonstrating the disruption of lysosomal homeostasis early in the development of the disease. See Roca et al., Hum Mol Genet 2017; 26(8):1535-51. Thus, results suggest the sustained reversal of the alteration of lysosomal physiology with the gene therapy treatment.

Figure 21:
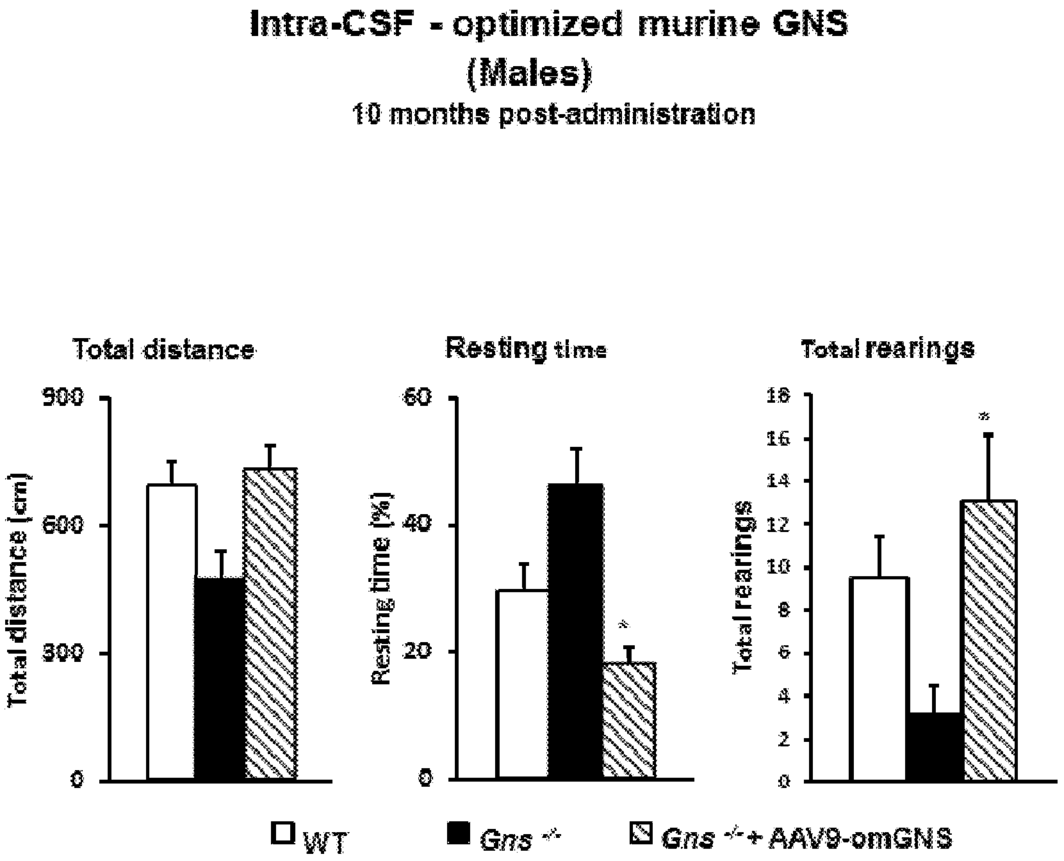
FIG. 21. Intra-CSF delivery of AAV9 vectors coding for optimized murine GNS (AAV9-CAG-omGNS). Long-term study. Open Field assessment of the locomotor and exploratory activity of naïve wild-type (healthy), untreated $Gns^{-/-}$ male mice and $Gns^{-/-}$ male mice administered in the CSF with $5\times10^{10}$ vg of control vector (AAV9-Null) or $5\times10^{10}$ vg of AAV9-CAG-omGNS vector at two months of age and analysed 10 months later. Total distance traveled, Resting time and Total number of rearings. Results are shown as mean±SEM, n=5-15 animals per group, *P<0.05 versus $Gns^{-/-}$ male mice.

Finally, the persistence of the therapeutic effect 10 months after a single administration of AAV9-CAG-omGNS vectors was also evident when animals were subjected to behavioural testing. One-year-old treated $Gns^{-/-}$ male mice had the same behaviour than healthy littermates, as opposed to the reduced locomotor activity observed in age-matched untreated MPSIIID mice. See FIG. 21.

Figure 22:
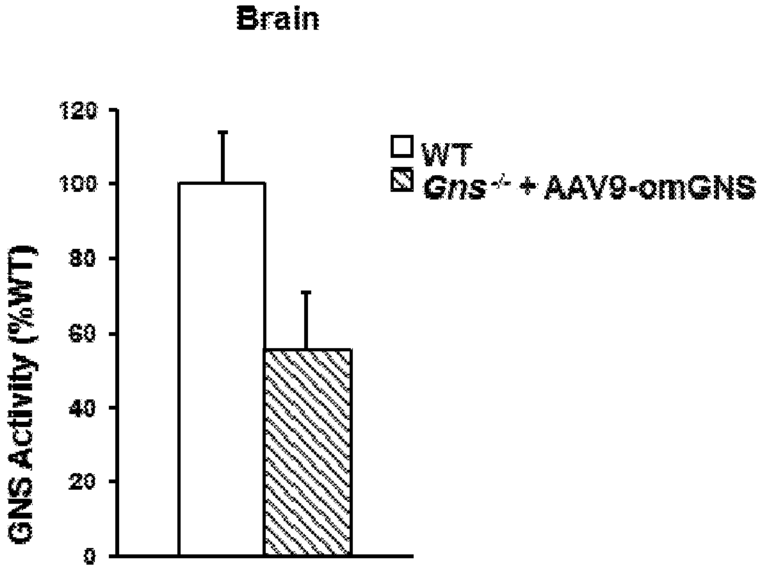
FIG. 22. Intra-CSF delivery of AAV9 vectors coding for optimized murine GNS (AAV9-CAG-omGNS). Long-term study. GNS activity in the brain of wild-type (healthy) mice (WT) and $Gns^{-/-}$ mice administered in the CSF, via intracisternal (IC) injection, with $5\times10^{10}$ vg of AAV9-CAG-omGNS. WT GNS activity was set to 100%. Activity was analysed at 22-months of age, i.e. 20 months after vector administration. Values are means±SEM of 4 mice per group.
Figure 23:
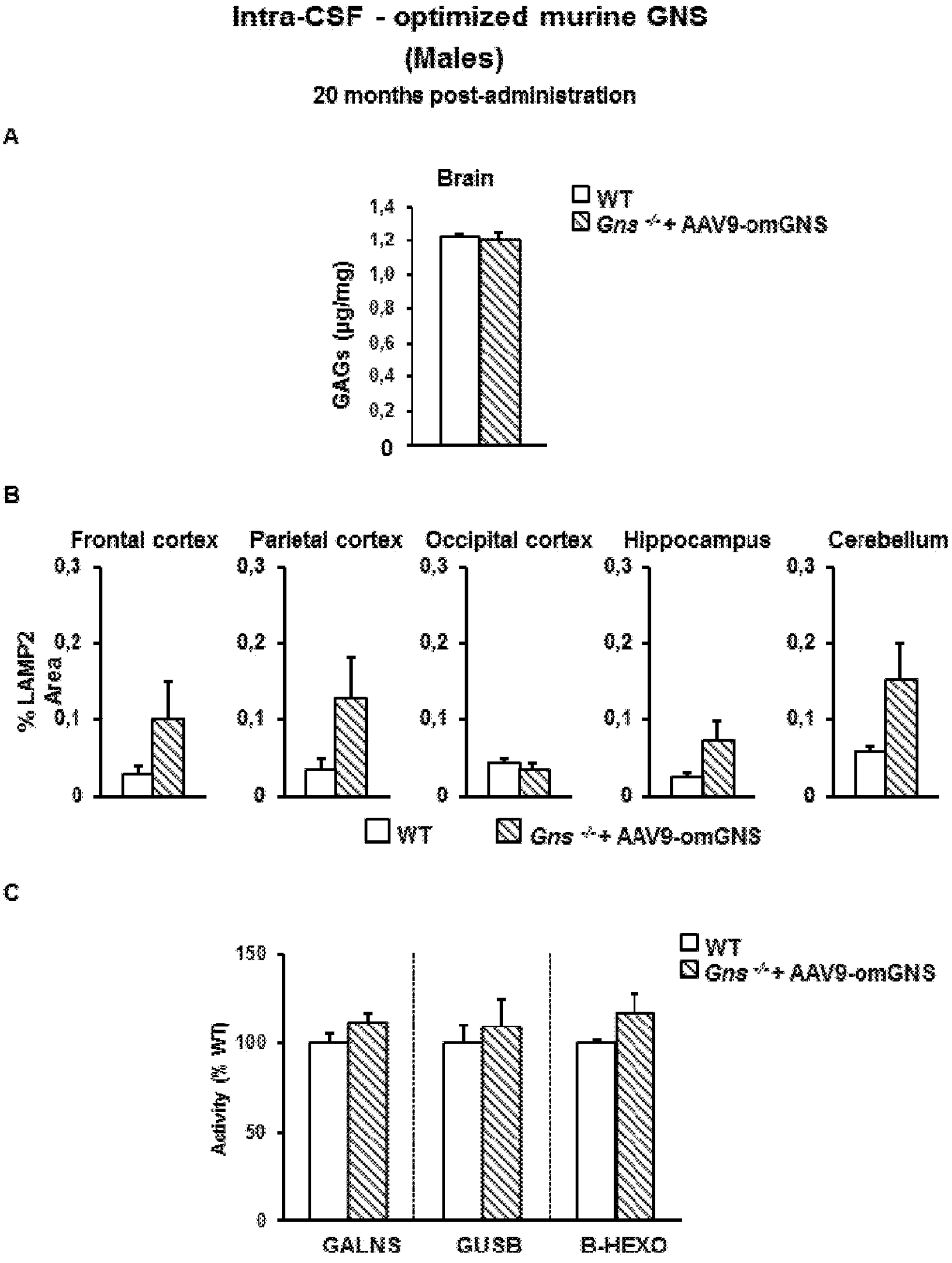
FIG. 23. Intra-CSF delivery of AAV9 vectors coding for optimized murine GNS (AAV9-CAG-omGNS). Long-term study. (A) Glycosaminoglycans (GAGs) content in the brain of wild-type (healthy) mice (WT) and $Gns^{-/-}$ male mice administered in the cisterna magna with $5\times10^{10}$ vector genomes of AAV9-CAG-omGNS vectors. The analysis was performed 20 months post vector delivery. (B) Quantification of the signal intensity in different areas of the brain following staining for the lysosomal marker LAMP-2 in the same cohort of animals as in (A). (C) Activity of other lysosomal enzymes in brain extracts obtained from the same cohorts of animals as in (A). GALNS galactosamine (N-acetyl)-6-sulfatase, GUSB, glucuronidase, beta, B-HEXO, hexosaminidase B. Values are means±SEM of 4 mice per group.
Figure 24:
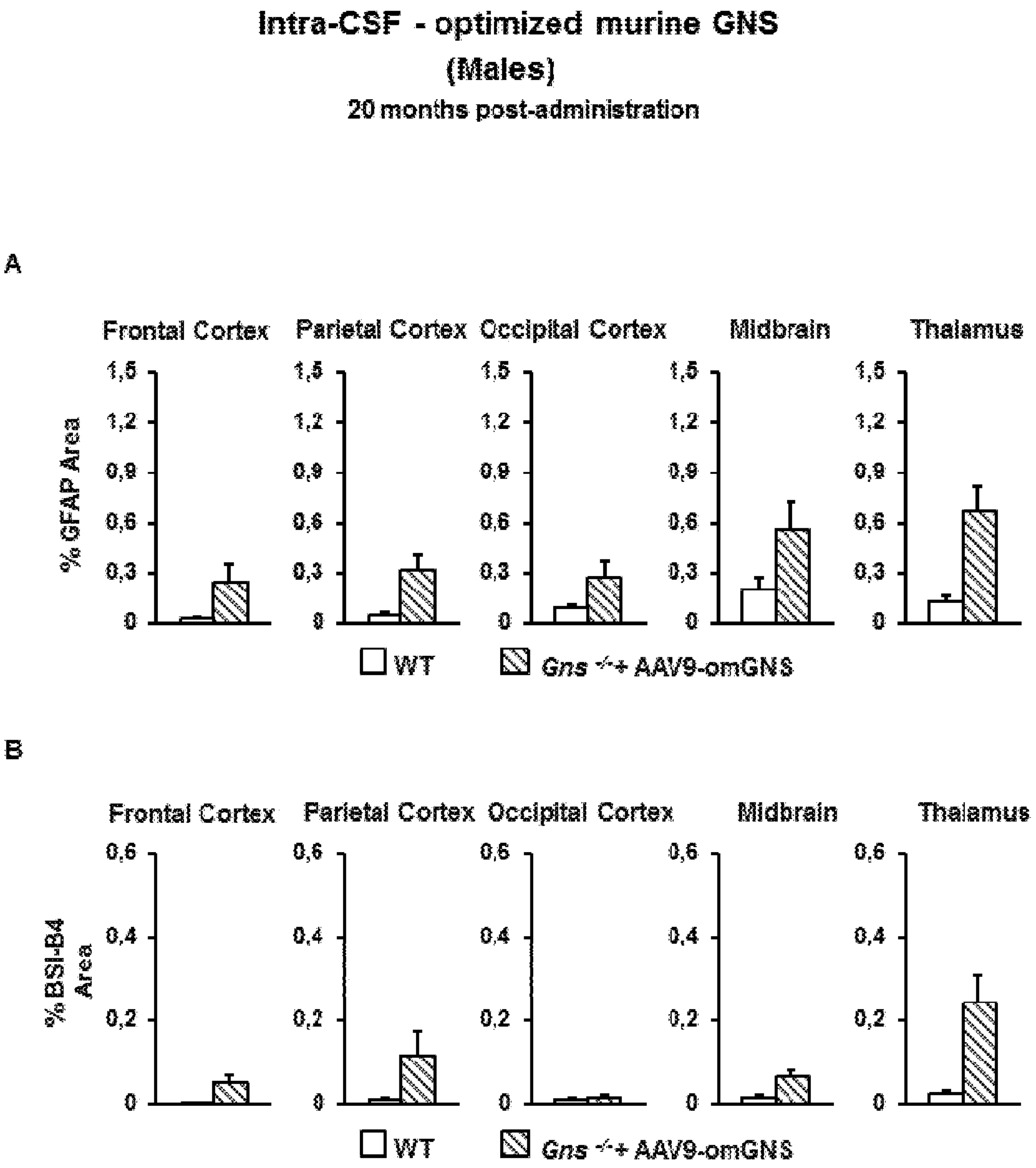
FIG. 24. Intra-CSF delivery of AAV9 vectors coding for optimized murine GNS (AAV9-CAG-omGNS). Long-term study. Evaluation of neuroinflammation in brain sections from wild-type (healthy) and $Gns^{-/-}$ male mice administered in the cisterna magna with $5\times10^{10}$ vector genomes of AAV9-CAG-omGNS vectors and analysed 20 months later. Histograms represent the signal intensity of the astrocyte marker GFAP (A) and the microglial marker BSI-B4 (B) in sections of frontal, parietal, and occipital cortex, superior colliculus, and thalamus. Results are shown as means±SEM of 4 mice per group.
Figure 25:
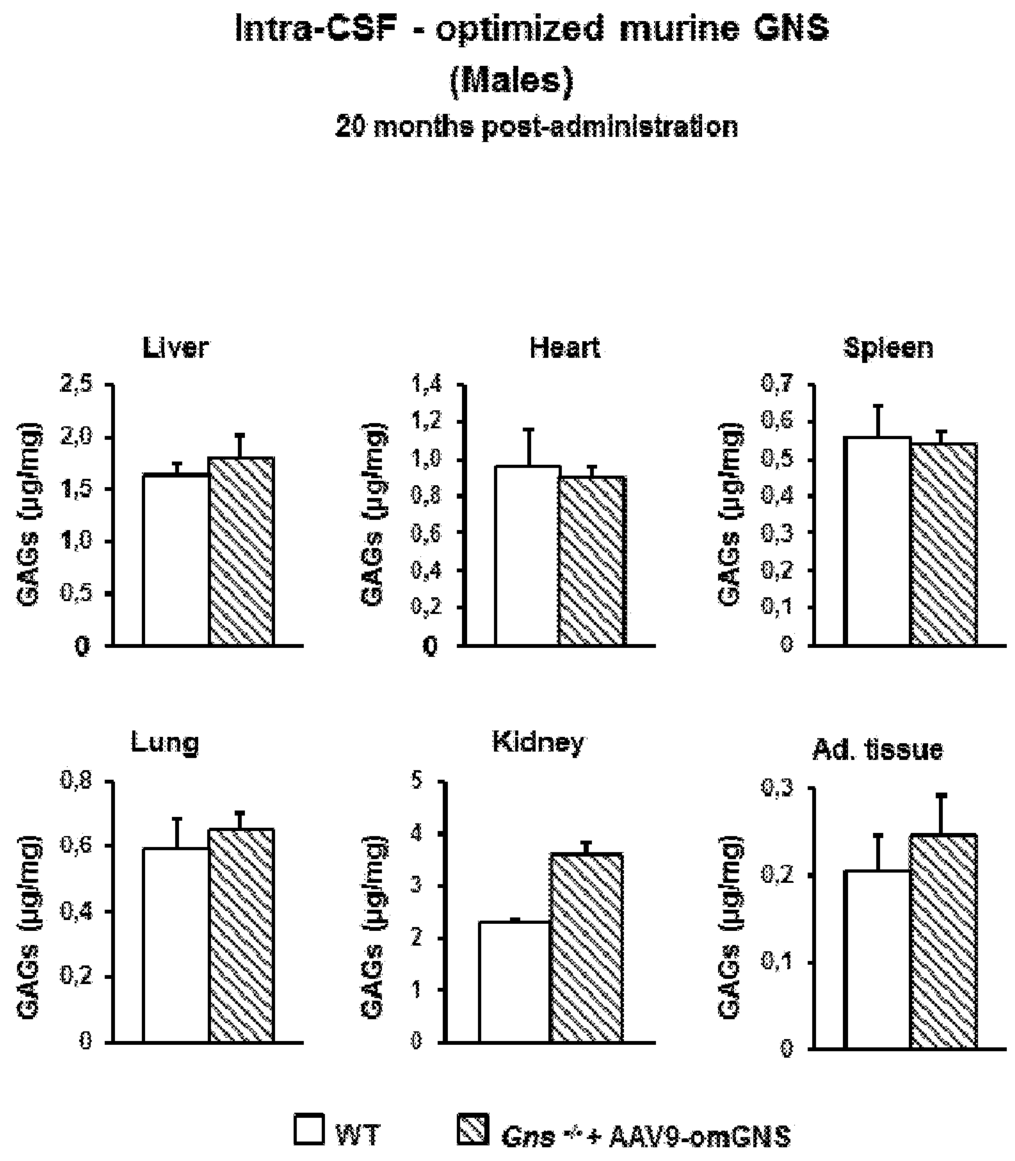
FIG. 25. Intra-CSF delivery of AAV9 vectors coding for optimized murine GNS (AAV9-CAG-omGNS). Long-term study. Quantification of glycosaminoglycans (GAGs) in somatic organs from wild-type (healthy) mice and $Gns^{-/-}$ male mice administered in the cisterna magna with $5\times10^{10}$ vector genomes of AAV9-CAG-omGNS vector at 2 months of age and analysed at 22 months of age. Results are shown as means±SEM of 4 mice per group.

Animal models of Sanfilippo disease have considerably shortened lifespan. See Haurigot V, et al., J Clin Invest. 2013; 1; pii:66778; Ribera A, et al., Hum Mol Genet. 2015; 24(7):2078-95. To evaluate therapeutic efficacy at what should be a very advanced stage of disease, another cohort of animals treated at 2 months of age with $5\times10^{10}$ vector genomes of AAV9-CAG-omGNS was analysed 20 months after vector administration, i.e when mice were almost 2 years old and most untreated MPSIIID animals were no longer alive. In 22-month-old treated MPSIIID animals, brain GNS activity remained at very high levels. See FIG. 22. This maintenance of therapeutic levels of GNS activity explained the normal levels of GAGs in the brain of treated MPSIIID mice, which showed similar GAG content than the brain of healthy wild-type littermates. See FIG. 23A. Accordingly, the size of the lysosomal compartment—evaluated morphometrically through the quantification of the signal intensity of the lysosomal marker LAMP2—was not statistically significantly increased in any of the CNS regions analysed. See FIG. 23B. Likewise, the activity of other lysosomal enzymes not affected by the mutation was similar to that recorded in healthy wild-type littermates, confirming normal lysosomal homeostasis in old treated MPSIIID mice. See FIG. 23C. The brains of 22-month-old treated MPSIIID mice also showed very low GFAP and BSI-B4 signals, indicating that the profound effect of the therapy on neuroinflammation persisted 20 months after a single administration of the therapeutic AAV9-CAG-omGNS vectors. See FIGS. 24 A and B. Finally, sustained production of GNS led to normal levels of GAG content in the peripheral organs of treated MPSIIID mice, in which liver, heart, spleen, lung and adipose tissue had the same GAG content than the peripheral organs of healthy age-matched animals. See FIG. 25.

Example 15: Intracisternal Delivery of AAV9-CAG-omGNS—Survival Study

Figure 26:
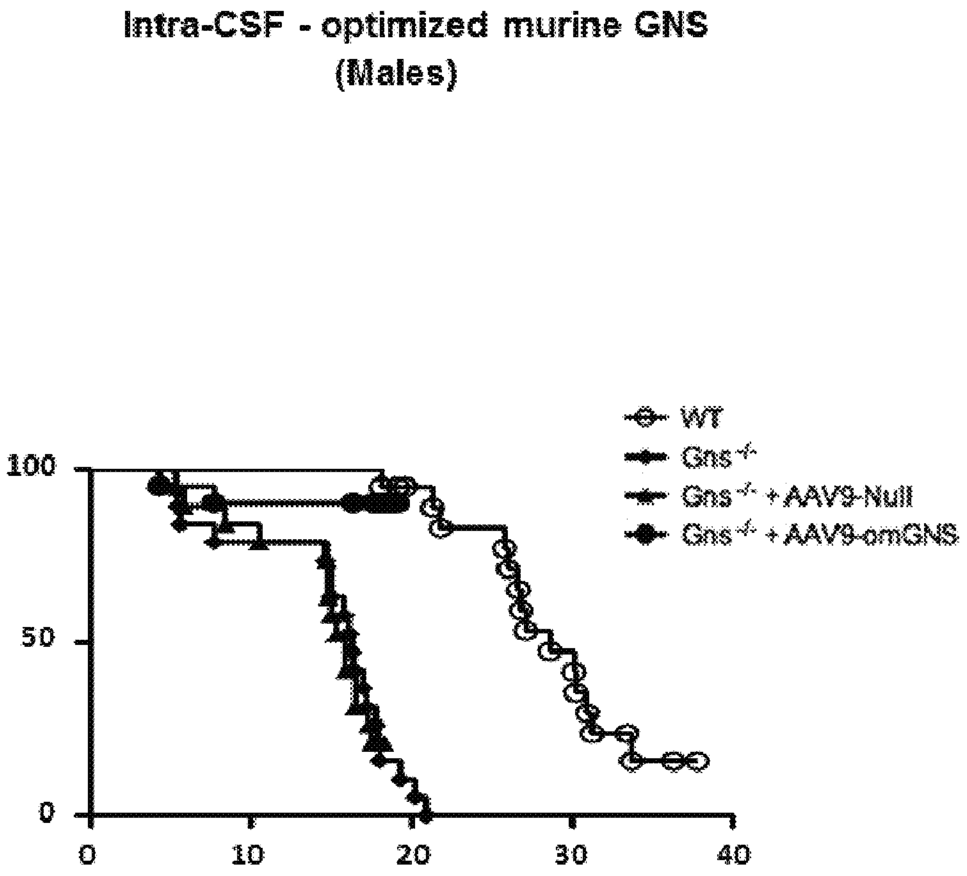
FIG. 26. Intra-CSF delivery of AAV9 vectors coding for optimized murine GNS (AAV9-CAG-omGNS). Kaplan-Meier analysis of survival in wild-type (healthy), untreated $Gns^{-/-}$ and $Gns^{-/-}$ male mice administered in the CSF with $5\times10^{10}$ vg of control vector (AAV9-Null) or $5\times10^{10}$ vg of AAV9-CAG-omGNS vector at two months of age. n=20 for WT, 19 for untreated $Gns^{-/-}$ mice, 19 for AAV9-Null-injected $Gns^{-/-}$ mice, and 20 for AAV9-CAG-omGNS-injected $Gns^{-/-}$ mice.

Finally, the effect of the intra-CSF administration of AAV9-CAG-omGNS vectors on survival was assessed. At 18 months, while all wild-type control mice were alive, 100% of non-treated Gns$^{-/-}$ mice and 80% of AAV9-null-treated Gns$^{-/-}$ mice were dead, demonstrating that GNS deficiency considerably shortens lifespan. Only 2 of a group of 20 Gns$^{-/-}$ mice administered with AAV9-CAG-omGns died over the same period, providing further proof of the efficacy of the therapy. See FIG. 26.

The invention claimed is:

1. A polynucleotide comprising an expression cassette, wherein the expression cassette comprises a transcriptional regulatory region comprising a promoter operatively linked to a nucleotide sequence as set forth in SEQ ID NO: 4 encoding the N-acetylglucosamine 6-sulfatase (GNS) protein.

2. The polynucleotide of claim 1 wherein the promoter is a constitutive promoter.

3. The polynucleotide of claim 2, wherein the promoter is the CAG promoter.

4. The polynucleotide of claim 1, wherein the expression cassette is flanked by adeno-associated virus inverted terminal repeats (ITRs).

5. A vector comprising the polynucleotide of claim 1, wherein the vector is an adeno-associated viral vector.

6. The vector of claim 5, wherein the vector is an Adeno-associated Viral Vector of serotype 9 (AAV9).

7. A pharmaceutical composition comprising a therapeutically effective amount of the vector of claim 5, and a pharmaceutically acceptable carrier and/or adjuvant.

8. A method for the treatment and/or prevention of mucopolysaccharidosis type IIID in a subject in need thereof comprising administering to the subject, the pharmaceutical composition of claim 7.

9. A method for the treatment and/or prevention of mucopolysaccharidosis type IIID in a subject in need thereof comprising administering to the subject, the vector of claim 5.

10. A pharmaceutical composition comprising a therapeutically effective amount of the polynucleotide of claim 1, and a pharmaceutically acceptable carrier and/or adjuvant.

11. A method for the treatment and/or prevention of mucopolysaccharidosis type IIID in a subject in need thereof comprising administering to the subject, the pharmaceutical composition of claim 10.

12. A method for the treatment and/or prevention of mucopolysaccharidosis type IIID in a subject in need thereof comprising administering to the subject, the polynucleotide of claim 1.

13. A method for obtaining a recombinant adeno-associated viral vector (AAV) comprising the polynucleotide of claim 1, comprising the steps of:

(i) providing a cell comprising the polynucleotide of claim 1, AAV cap proteins, AAV rep proteins and, optionally, viral proteins upon which AAV is dependent for replication, (ii) maintaining the cell under conditions adequate for assembly of the AAV; and (iii) purifying the adeno-associated viral vector produced by the cell.

14. A plasmid pAAV-CAG-ohGNS-version3 having accession number DSM 32345, as set forth in SEQ ID NO: 8.

* * * * *